US007034049B1

United States Patent
Pevarello et al.

(10) Patent No.: US 7,034,049 B1
(45) Date of Patent: Apr. 25, 2006

(54) 3(5)-AMINO-PYRAZOLE DERIVATIVES, PROCESS FOR THEIR PREPARATION AND THEIR USE AS ANTITUMOR AGENTS

(75) Inventors: Paolo Pevarello, Pavia (IT); Paolo Orsini, Varese (IT); Gabriella Traquandi, Milan (IT); Mario Varasi, Milan (IT); Edward L. Fritzen, Portage, MI (US); Martha A. Warpehoski, Portage, MI (US); Betsy S. Pierce, Kalamazoo, MI (US); Maria Grabriella Brasca, Milan (IT)

(73) Assignees: Pharmacia Italia S.p.A., Milan (IT); Pharmacia & Upjohn Company LLC, Kalamazoo, MI (US)

( * ) Notice: Subject to any disclaimer, the term of this patent is extended or adjusted under 35 U.S.C. 154(b) by 0 days.

(21) Appl. No.: 10/048,486

(22) PCT Filed: May 5, 2000

(86) PCT No.: PCT/US00/06699

§ 371 (c)(1),
(2), (4) Date: May 1, 2002

(87) PCT Pub. No.: WO01/12189

PCT Pub. Date: Feb. 22, 2001

Related U.S. Application Data

(63) Continuation-in-part of application No. 09/372,831, filed on Aug. 12, 1999, now abandoned.

(51) Int. Cl.
| *A61K 31/415* | (2006.01) |
| *C07D 231/38* | (2006.01) |
| *C07D 401/12* | (2006.01) |
| *C07D 403/12* | (2006.01) |
| *C07D 413/12* | (2006.01) |

(52) U.S. Cl. .......... 514/404; 548/372.5; 548/372.1; 548/248; 548/364.4; 548/364.7; 548/365.7; 548/372.2; 544/355; 544/140; 544/371; 546/275.4; 546/211

(58) Field of Classification Search ............. 548/372.5, 548/372.1, 248, 364.4, 364.7, 365.7; 544/355, 544/140, 371; 514/404; 546/275.4, 211
See application file for complete search history.

(56) References Cited

U.S. PATENT DOCUMENTS

| 5,162,360 A | 11/1992 | Creswell |
| 6,218,418 B1 * | 4/2001 | Pevarello et al. ........... 514/404 |
| 6,455,559 B1 * | 9/2002 | Pevarello et al. ........... 514/376 |

FOREIGN PATENT DOCUMENTS

WO     WO 9932455 A     7/1999

OTHER PUBLICATIONS

Vogel et al. Helvetica Chimica Acta (1975), 58(3), 761-71.*
Brinkmeyer et al. Journal of Heterocyclic Chemistry (1989), 26(6), 1713-17.*
Cancer and Metastasis Reviews (1998), 17(1), 91-106.*
Science (1999), vol. 286, 531-537.*
Brinkmeyer et al.: "Dimerization of Pyrazole-5-hydroxypyr-rolidinones to tetrazocines" Heterocycl. Chem. Chemical Abstracts, vol. 112, No. 23, pp. 1713-1717 Jun. 4, 1990.
Pevarello P. et al., "3-Aminopyrazole Inhibitors of CDK2/Cyclin A as Antitumor Agents.1. Lead Finding", J. Med. Chem. 47:3367-3380 (2004).
Brinkmeyer et al.: "Dimerization of Pyrazole-5-hydroxypyr-rolidinones to tetrazocines" Chemical Abstracts, vol. 112, No. 23, abstract No. 216898c Jun. 4, 1990.

* cited by examiner

*Primary Examiner*—Kamal A. Saeed
*Assistant Examiner*—Rebecca Anderson
(74) *Attorney, Agent, or Firm*—Scully, Scott, Murphy & Presser, P.C.

(57) ABSTRACT

Compounds which are 3-amino-pyrazole derivatives represented by formula (I) wherein R is $C_3$–$C_6$ cycloalkyl group optionally substituted by a straight or branched $C_1$–$C_6$ alkyl or arylalkyl group; $R_1$ is a straight or branched $C_1$–$C_6$ alkyl, $C_2$–$C_4$ alkenyl, cycloalkyl, cycloalkenyl, heterocyclyl, aryl, arylalkyl, arylcarbonyl, aryloxyalkyl or arylalkenyl group, each of which may be optionally further substituted as indicated in the description; or a pharmaceutically acceptable salt thereof. The compounds are useful for the treatment of cancer, cell proliferative disorders, Alzheimer's disease, viral infections, auto-immune diseases or neurodegenerative diseases.

11 Claims, No Drawings

3(5)-AMINO-PYRAZOLE DERIVATIVES, PROCESS FOR THEIR PREPARATION AND THEIR USE AS ANTITUMOR AGENTS

This application is a 371 of PCT/US00/06699 filed May 5, 2000 and is a continuation in part of application Ser. No. 09/372,831 filed Aug. 12, 1999, now abandoned.

BACKGROUND OF THE INVENTION

1. Field of the Invention

The present invention relates to 3(5)-amino-pyrazole derivatives, to a process for their preparation, to pharmaceutical compositions containing them, and to their use as therapeutic agents, particularly in the treatment of cancer and cell proliferative disorders.

2. Discussion of the Background

Several cytotoxic drugs such as, e.g., fluorouracil (5-FU), doxorubicin and camptothecins, damage DNA or affect cellular metabolic pathways and thus cause, in many cases, an indirect block of the cell cycle. Therefore, by producing an irreversible damage to both normal and tumor cells, these agents result in a significant toxicity and side-effects.

In this respect, compounds capable of functioning as highly specific antitumor agents by selectively leading to tumor cell arrest and apoptosis, with comparable efficacy but reduced toxicity than the currently available drugs, are desirable.

It is well known that progression through the cell cycle is governed by a series of checkpoint controls, otherwise referred to as restriction points, which are regulated by a family of enzymes known as the cyclin-dependent kinases (cdk). In turn, the cdks themselves are regulated at many levels such as, for instance, binding to cyclins.

The coordinated activation and inactivation of different cyclin/cdk complexes is necessary for normal progression through the cell cycle. Both the critical G1-S and G2-M transitions are controlled by the activation of different cyclin/cdk activities. In G1, both cyclin D/cdk4 and cyclin E/cdk2 are thought to mediate the onset of S-phase. Progression through S-phase requires the activity of cyclin. A/cdk2 whereas the activation of cyclin A/cdc2 (cdk1) a cyclin B/cdc2 are required for the onset of metaphases. For a general reference for cyclins and cyclin-dependent kinases see, for instance, Kevin R. Webster et al, in Exp. Opin. Invest. Drugs, 1998, Vol. 7(6), 865–887.

Checkpoint controls are defective in tumor cells due, in part, to disregulation of cdk activity. For example altered expression of cyclin E and cdks has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

SUMMARY OF THE INVENTION

It is an object of the invention to provide compounds which are useful in treating cell proliferative disorders associated with an altered cell dependent kinase activity. It is another object to provide compounds which have cdk/cyclin kinase inhibitory activity.

It is another object of the invention to provide compounds which are useful in therapy as antitumor agents but lack, in terms of both toxicity and side effects, the drawbacks associated with currently available antitumor drugs discussed above.

The present inventors have now discovered that 3-amino-pyrazoles are endowed with cdk/cyclin kinase inhibitory activity and are thus useful in therapy as antitumor agents and lack, in terms of both toxicity and side effects, the aforementioned drawbacks associated with currently available antitumor drugs.

More specifically, the 3-amino-pyrazoles of the invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Due to the key role of cdks in the regulation of cellular proliferation, the 3-amino-pyrazole derivatives are also useful in the treatment of a variety of cell proliferative disorders such as, for example, benign prostate hyperplasia, familial adenomatosis polyposis, neurofibromatosis, psoriasis, vascular smooth cell proliferation associated with atherosclerosis, pulmonary fibrosis, arthritis glomerulonephritis and post-surgical stenosis and restenosis.

The compounds of the invention may be useful in treatment of Alzheimer's disease, as suggested by the fact that cdk5 is involved in the phosphorylation of tau protein (J. Biochem. 117, 741–749, 1995).

The compounds of this invention, as modulators of apoptosis, may also be useful in the treatment of cancer, viral infections, prevention of AIDS development in HIV-infected individuals, autoimmune diseases and neurodegenerative disorders.

The compounds of this invention may be useful in inhibiting tumor angiogenesis and metastasis.

The compounds of the invention may also act as inhibitor of other protein kinases, e.g., protein kinase C, her2, raf1, MEK1, MAP kinase, EGF receptor, PDGF receptor, IGF receptor, PI3 kinase, weel kinase, Src, Ab1, and thus be effective in the treatment of diseases associated with other protein kinases.

The compounds of the invention are also useful in the treatment and prevention of radiotherapy-induced or chemotherapy-induced alopecia.

Accordingly, the present invention provides a method for treating cell proliferative disorders associated with an altered cell dependent kinase activity, by administering to a mammal in need thereof an effective amount of a 3-amino-pyrazole derivative represented by formula (I):

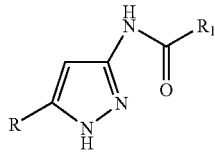

(I)

wherein
R is a $C_3$–$C_6$ cycloalkyl group optionally substituted by a straight or branched $C_1$–$C_6$ alkyl or arylalkyl group;
$R_1$ is a straight or branched $C_1$–$C_6$ alkyl, $C_2$–$C_4$ alkenyl, cycloalkyl, cycloalkenyl, heterocyclyl, aryl, arylalkyl, arylcarbonyl, aryloxyalkyl or arylalkenyl group, each of which may be optionally further substituted;

or a pharmaceutically acceptable salt thereof.

In a preferred embodiment of the method described above, the cell proliferative disorder is selected from the group consisting of cancer, Alzheimer's disease, viral infections, auto-immune diseases and neurodegenerative disorders.

Specific types of cancer that may be treated include carcinoma, squamous cell carcinoma, hematopoietic tumors of myeloid or lymphoid lineage, tumors or mesenchymal origin, tumors of the central and peripheral nervous system, melanoma, seminoma, teratocarcinoma, osteosarcoma, xenoderoma pigmentosum, keratoctanthoma, thyroid follicular cancer, and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

In addition, the inventive method provides tumor angiogenesis and metastasis inhibition. The inventive method may also provide cell cycle inhibition or cdk/cyclin dependent inhibition.

In addition to the above, the method object of the present invention provides treatment and prevention of radiotherapy-induced or chemotherapy-induced alopecia.

The present invention also provides a 3-amino-pyrazole derivative represented by formula (I):

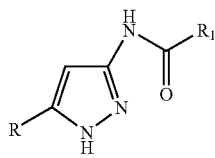

(I)

wherein
R is a $C_3$–$C_6$ cycloalkyl group optionally substituted by a straight or branched $C_1$–$C_6$ alkyl or arylalkyl group;
$R_1$ is a straight or branched $C_1$–$C_6$ alkyl, $C_2$–$C_4$ alkenyl, cycloalkyl, cycloalkenyl, heterocyclyl, aryl, arylalkyl, arylcarbonyl, aryloxyalkyl or arylalkenyl group, each of which may be optionally further substituted;

or a pharmaceutically acceptable salt thereof.

The present invention also includes methods of synthesizing the 3-amino-pyrazole derivative represented by formula (I). A pharmaceutical composition comprising the 3-amino-pyrazole derivative represented by formula (I) is also included in the present invention.

The present invention also includes a compound useful in the synthesis the 3-amino-pyrazole derivative represented by formula (I), which is represented by formula (V):

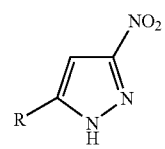

(V)

wherein R is a $C_3$–$C_6$ cycloalkyl group optionally substituted with a straight or branched $C_1$–$C_6$ alkyl group.

A more complete appreciation of the invention and many of the attendant advantages thereof will be readily obtained as the same becomes better understood by reference to the following detailed description.

DETAILED DESCRIPTION OF THE INVENTION

Several 3-amino-pyrazole derivatives are known as pesticides, herbicides or even as therapeutic agents. Among them are, as an example, heteroaryl-pyrazoles active as p38 kinase inhibitors (WO 98/52941, G.D. Searle and Co.) and other 3-amino-pyrazoles which inhibit protein kinases (WO 96/14843, COR Therapeutics, Inc.).

As will be readily appreciated, the unsubstituted ring nitrogen pyrazoles in the compounds of the invention are known to rapidly equilibrate, in solution, as admixtures of both tautomers:

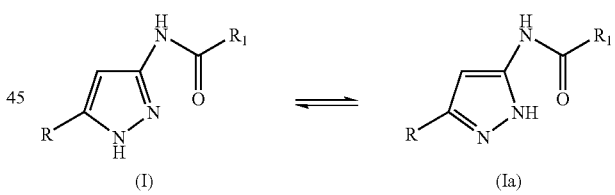

(I)     (Ia)

Accordingly, in the present invention, where only one tautomer is indicated for the compounds of formula (I), the other, (Ia), is also within the scope of the present invention, unless specifically noted otherwise.

As used herein, unless otherwise specified, the term $C_3$–$C_6$ cycloalkyl includes cyclopropyl, cyclobutyl, cyclopentyl and cyclohexyl; the term cycloalkyl is also intended to cover cycloalkyl groups with, e.g., up to 10 carbon atoms, e.g., an adamantane group.

As used herein, unless otherwise indicated, the term cycloalkenyl includes the above cycloalkyl rings wherein at least one carbon-carbon bond forming the said ring is a double bond.

As used herein, unless otherwise indicated, the term alkyl includes straight or branched $C_1$–$C_6$ alkyl groups such as, for instance, methyl, ethyl, n-propyl, isopropyl, n-butyl, isobutyl, sec-butyl, tert-butyl, n-pentyl, n-hexyl and the like.

As used herein, unless otherwise indicated, the term $C_2$–$C_4$ alkenyl includes a group selected from vinyl, allyl, 1-propenyl, isopropenyl, 1-butenyl, 2-butenyl, 3-butenyl and the like.

The term aryl includes mono-, bi- or poly-carbocyclic or heterocyclic hydrocarbons with from 1 to 4 ring moieties, wherein at least one of the rings is aromatic, either fused or linked to each other by single bonds. Thus, these groups may have 5 to 20 carbon atoms. Preferably 6 to 20 carbon atoms.

Examples of aryl groups are, for instance, phenyl, biphenyl, α- or β-naphthyl, dihydronaphthyl, thienyl, benzothienyl, furyl, isobenzofuranyl, dihydrobenzofuranyl, chromenyl, xanthenyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, fluorenyl, bicyclo[4.2.0]octa-1,3,5-trien-yl, dibenzo[b,d]furanyl, chromanyl, chromenyl, triazolyl, tetrazolyl, tetrazol[1,5-b]pyridazinyl, benzodioxinyl and the like.

The term heterocycle, hence encompassing heteroaromatic rings also referred to as aryl groups, includes a 3 to 6 membered saturated or unsaturated carbocycle wherein one or more carbon atoms are replaced by one or more atoms selected from nitrogen, oxygen and sulphur. Examples of saturated or partly unsaturated heterocycles are, for instance, azetidine, pyran, pyrrolidine, pyrroline, imidazolidine, imidazoline, dihydrofurane, tetrahydrofuran, dihydropyrrole, 1,3-dioxolane, piperidine, piperazine, morpholine and the like.

According to the above indicated substituent meanings and unless otherwise specified, any of the above $R_1$ groups may be optionally substituted in any of the free positions by one or more groups, for instance 1 to 6 groups, independently selected from: halogen, nitro, oxo groups (C=O), cyano, alkyl, perfluorinated alkyl, hydroxyalkyl, aryl, arylalkyl, heterocyclyl, cycloalkyl, hydroxy, alkoxy, perfluorinated alkoxy, aryloxy, heterocyclyloxy, methylenedioxy, alkylcarbonyloxy, arylcarbonyloxy, carboxy, alkoxycarbonyl, aryloxycarbonyl, cycloalkyloxycarbonyl, amino, ureido, alkylamino, dialkylamino, arylamino, diarylamino, formylamino, alkylcarbonylamino, arylcarbonylamino, heterocyclylcarbonylamino, alkoxycarbonylamino, alkoxyimino, alkylsulfonylamino, arylsulfonylamino, formyl, alkylcarbonyl, arylcarbonyl, cycloalkylcarbonyl, heterocyclylcarbonyl, aminocarbonyl, alkylaminocarbonyl, dialkylaminocarbonyl, alkylsulfonyl, arylsulfonyl, aminosulfonyl, alkylaminosulfonyl, dialkylaminosulfonyl, arylthio and alkylthio.

In their turn, whenever appropriate, each of the above possible substituents may be further substituted by one or more of the aforementioned groups. Compounds of formula (I) wherein the given $R_1$ group is substituted by one or more of the aforementioned substituents which, in turn, are optionally further substituted as set forth above, are given below.

Just as an example, the compound N-(3-cyclopropyl-1H-pyrazol-5-yl)-2-[2,2-difluoro-3-(3-fluorophenyl)cyclopropyl]acetamide is represented by formula (I) wherein $R_1$ is alkyl (e.g. methyl), the alkyl being substituted by cycloalkyl (e.g. cyclopropyl), the cycloalkyl being further substituted by two halogen atoms (e.g. fluorine) and by an aryl group (e.g. phenyl), the aryl group being substituted by a halogen atom (e.g. fluorine).

Among the meanings of the substituents and unless otherwise indicated, the term halogen atom includes, fluorine, chlorine, bromine and iodine; the term perfluorinated alkyl and alkoxy group includes an alkyl or alkoxy group further substituted by more than one fluorine atom such as, for example, trifluoromethyl, trifluoromethoxy and the like.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, cycloalkyl and heterocycly moieties are as above defined.

Pharmaceutically acceptable salts of the compounds of formula (I) include the acid addition salts with inorganic or organic acids, e.g., nitric, hydrochloric, hydrobromic, sulphuric, perchloric, phosphoric, acetic, trifluoroacetic propionic, glycolic, lactic, oxalic, malonic, malic, maleic, tartaric, citric, benzoic, cinnamic, mandelic, methanesulphonic, isethionic and salicyclic acid, as well as the salts with inorganic or organic bases, e.g., alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

The compounds of formula (I) may have asymmetric carbon atoms and may therefore exist either as racemic admixtures or as individual optical isomers.

Accordingly, the use an an antitumor agent of all possible isomers and their admixtures and of both metabolites and the pharmaceutically acceptable bio-precursors (otherwise referred to as pro-drugs) of the compounds of formula (I) are also within the scope of the present invention.

Preferred compounds of the invention of formula (I) are those wherein R is a cycloalkyl group and $R_1$ is a $C_1$–$C_4$ alkyl, cycloalkyl, aryl, arylalkyl, 5 or 6 membered heterocyclyl or heterocyclylalkyl group, which may be optionally further substituted as described above. Even more preferred compounds represented by formula (I) are those wherein R is cycloalkyl and $R_1$ is $C_1$–$C_4$ alkyl, phenyl, phenylalkyl, phenylalkenyl, biphenyl, biphenylalkyl, α- or β-naphthyl, α- or β-naphthylalkyl, pyridyl, thienyl, thienylalkyl, isoxazolyl, isoxazolylalkyl, pyrazolyl, pyrazolylalkyl, furyl, thiazolyl, thiazolylalkyl, pyrrolyl, dihydropyrrolyl, indolyl, indolylalkyl, benzothienyl, benzothienylalkyl, florenylalkyl, pyrimidinylalkyl, quinoxalynyl and cyclopropyl.

Still more preferred, within this class, are the compounds of formula (I) wherein R is cyclopropyl.

Examples of preferred compounds of the invention, which may be in the form of pharmaceutically acceptable salts, e.g., a hydrobromide or hydrochloride salt, include the following:

1. N-(5-cyclopropyl-1H-pyrazol-3-yl)-2,2-diphenylacetamide;
2. N-(3-cyclopropyl-1H-pyrazol-5-yl)-2-(4-nitrophenyl)acetamide;
3. N-(3-cyclopropyl-1H-pyrazol-5-yl)-4-methoxybenzamide;
4. N-(3-cyclopropyl-1H-pyrazol-5-yl)-2-(3-methoxyphenyl)acetamide;
5. N-(3-cyclopropyl-1H-pyrazol-5-yl)-2-[4-(dimethylamino)phenyl]acetamide;
6. N-(3-cyclopropyl-1H-pyrazol-5-yl)-1-phenylcyclopropancarboxamide;
7. 2-(1,3-benzodioxol-5-yl-N-(3-cyclopropyl-1H-pyrazol-5-yl)acetamide;
8. N-(3-cyclopropyl-1H-pyrazol-5-yl)-2-(4-methoxyphenyl)acetamide;
9. N-(3-cyclopropyl-1H-pyrazol-5-yl)-2-phenylpropanamide;

10. N-(3-cyclopropyl-1H-pyrazol-5-yl)-2-(3,4-dimethoxyphenyl)acetamide;
11. N-(3-cyclopropyl-1H-pyrazol-5-yl)-2-(1H-indol-3-yl)acetamide;
12. N-(3-cyclopropyl-1H-pyrazol-5-yl)-2-(5-methoxy-1H-indol-3-yl)acetamide;
13. N-(3-cyclopropyl-1H-pyrazol-5-yl)-2-(1-methyl-1H-indol-3-yl)acetamide;
14. 2-(5-chloro-1-benzothiophen-3-yl)-N-(3-cyclopropyl-1H-pyrazol-5-yl)acetamide;
15. 2-(1-benzothiophen-3-yl)-N-(3-cyclopropyl-1H-pyrazol-5-yl)acetamide;
16. N-(3-cyclopropyl-1H-pyrazol-5-yl)-3-cyclopentylpropanamide;
17. 2-(4-chlorophenyl)-N-(3-cyclopropyl-1H-pyrazol-5-yl)acetamide;
18. N-(3-cyclopropyl-1H-pyrazol-5-yl)-4-oxo-4-phenylbutanamide;
19. N-(3-cyclopropyl-1H-pyrazol-5-yl)-2-(2,3-dihydro-1H-inden-5-yl)acetamide;
20. 3-(2-chlorophenoxy)-N-(3-cyclopropyl-1H-pyrazol-5-yl)propanamide;
21. N-(3-cyclopropyl-1H-pyrazol-5-yl)-2-oxo-2-phenylacetamide;
22. N-(3-cyclopropyl-1H-pyrazol-5-yl)-2-(4-methylphenyl)acetamide;
23. 2-[1,1'-biphenyl]-4-yl-N-(3-cyclopropyl-1H-pyrazol-5-yl)acetamide;
24. N-(3-cyclopropyl-1H-pyrazol-5-yl)-2-(3-chlorophenyl)acetamide;
25. N-(3-cyclopropyl-1H-pyrazol-5-yl)-2-(1-naphtyl)acetamide;
26. N-(3-cyclopropyl-1H-pyrazol-5-yl)-2-(2-fluorophenyl)acetamide;
27. N-(3-cyclopropyl-1H-pyrazol-5-yl)-2-(2-chlorophenyl)acetamide;
28. N-(3-cyclopropyl-1H-pyrazol-5-yl)-2-(4-fluorophenyl)acetamide;
29. N-(3-cyclopropyl-1H-pyrazol-5-yl)-2-(4-trifluoromethyl-phenyl)acetamide;
30. N-(3-cyclopropyl-1H-pyrazol-5-yl)-2-methoxy-2-phenylacetamide;
31. N-(3-cyclopropyl-1H-pyrazol-5-yl)-3-oxo-1-indanecarboxamide;
32. N-(3-cyclopropyl-1H-pyrazol-5-yl)-2-(3-thienyl)acetamide;
33. N-(3-cyclopropyl-1H-pyrazol-5-yl)bicyclo[4.2.0]octa-1,3,5-triene-7-carboxamide;
34. N-(3-cyclopropyl-1H-pyrazol-5-yl)-4-phenyl-3-butenamide;
35. 4-[(4-chlorophenyl)sulphonyl]-N-(5-cyclopropyl-1H-pyrazol-3-yl)-3-methyl-2-thiophenecarboxamide;
36. 5-[(4-chlorophenyl)sulphonyl]-N-(5-cyclopropyl-1H-pyrazol-3-yl)-3-methyl-2-thiophenecarboxamide;
37. N-(5-cyclopropyl-1H-pyrazol-3-yl)-4-phenoxybenzamide;
38. 4-bromo-N-(5-cyclopropyl-1H-pyrazol-3-yl)benzamide;
39. N-(5-cyclopropyl-1H-pyrazol-3-yl)-3,5-bis(trifluoromethyl)benzamide;
40. N-(5-cyclopropyl-1H-pyrazol-3-yl)-3,3-dimethylbutanamide;
41. N-(5-cyclopropyl-1H-pyrazol-3-yl)-4-iodobenzamide;
42. N-(5-cyclopropyl-1H-pyrazol-3-yl)-1-napthamide;
43. N-(5-cyclopropyl-1H-pyrazol-3-yl)-3-cyanobenzamide;
44. N-(5-cyclopropyl-1H-pyrazol-3-yl)-1,3-benzodioxole-5-carboxamide;
45. 3-(2-chlorophenyl)-N-(5-cyclopropyl-1H-pyrazol-3-yl)-2-propenamide;
46. 2,5-dichloro-N-(5-cyclopropyl-1H-pyrazol-3-yl)-3-thiophenecarboxamide;
47. N-(5-cyclopropyl-1H-pyrazol-3-yl)-2-(propylsulfanyl)nicotinamide;
48. N-(5-cyclopropyl-1H-pyrazol-3-yl)-2,2,5,7-tetramethyl-1-oxo-4-indanecarboxamide;
49. N-(5-cyclopropyl-1H-pyrazol-3-yl)-2-pyridinecarboxamide;
50. N-(5-cyclopropyl-1H-pyrazol-3-yl)-2-adamantancarboxamide;
51. N-(5-cyclopropyl-1H-pyrazol-3-yl)-4-methylbenzamide;
52. N-(5-cyclopropyl-1H-pyrazol-3-yl)-2,3,4,5,6-pentafluorobenzamide;
53. N-(5-cyclopropyl-1H-pyrazol-3-yl)-2-phenylacetamide;
54. N-(5-cyclopropyl-1H-pyrazol-3-yl)-cyclopentancarboxamide;
55. N-(5-cyclopropyl-1H-pyrazol-3-yl)-2-(2-thienyl)acetamide;
56. N-(5-cyclopropyl-1H-pyrazol-3-yl)-3,5-dichlorobenzamide;
57. 2-chloro-N-(5-cyclopropyl-1H-pyrazol-3-yl)-6-methyl-isonicotinamide;
58. N-(5-cyclopropyl-1H-pyrazol-3-yl)-5-isoxazolecarboxamide;
59. 2,4-dichloro-N-(5-cyclopropyl-1H-pyrazol-3-yl)-5-fluorobenzamide;
60. N-(5-cyclopropyl-1H-pyrazol-3-yl)-2,4-difluorobenzamide;
61. N-(5-cyclopropyl-1H-pyrazol-3-yl)-2-chlorobenzamide;
62. N-(5-cyclopropyl-1H-pyrazol-3-yl)-2,4-dichlorobenzamide;
63. N-(5-cyclopropyl-1H-pyrazol-3-yl)-2,6-dichlorobenzamide;
64. N-(5-cyclopropyl-1H-pyrazol-3-yl)-2-methoxybenzamide;
65. N-(5-cyclopropyl-1H-pyrazol-3-yl)-2-methylbenzamide;
66. N-(5-cyclopropyl-1H-pyrazol-3-yl)-3-fluorobenzamide;
67. N-(5-cyclopropyl-1H-pyrazol-3-yl)-3-chlorobenzamide;
68. N-(5-cyclopropyl-1H-pyrazol-3-yl)-3,5-dimethoxybenzamide;
69. N-(5-cyclopropyl-1H-pyrazol-3-yl)-3-methylbenzamide;
70. N-(5-cyclopropyl-1H-pyrazol-3-yl)-4-fluorobenzamide;
71. N-(5-cyclopropyl-1H-pyrazol-3-yl)-4-trifluoromethyl-benzamide;
72. Methyl 4-[(5-cyclopropyl-1H-pyrazol-3-yl)amino]-4-oxobutanoate;
73. N-(5-cyclopropyl-1H-pyrazol-3-yl)-cyclopropanecarboxamide;
74. N-(5-cyclopropyl-1H-pyrazol-3-yl)-4-cyanobenzamide;
75. N-(5-cyclopropyl-1H-pyrazol-3-yl)-2-napthamide;
76. N-(5-cyclopropyl-1H-pyrazol-3-yl)-2-thiophenecarboxamide;
77. N-(5-cyclopropyl-1H-pyrazol-3-yl)-2-quinoxalinecarboxamide;
78. N-(5-cyclopropyl-1H-pyrazol-3-yl)-3,4-difluorobenzamide;
79. N-(5-cyclopropyl-1H-pyrazol-3-yl)-3,5-difluorobenzamide;
80. N-(5-cyclopropyl-1H-pyrazol-3-yl)-2-(2,5-dimethoxyphenyl)acetamide;
81. N-(5-cyclopropyl-1H-pyrazol-3-yl)-2-ethoxybenzamide;

82. N-(5-cyclopropyl-1H-pyrazol-3-yl)-3,4-dimethoxybenzamide;
83. N-(5-cyclopropyl-1H-pyrazol-3-yl)-2-phenylbutanamide;
84. N-(5-cyclopropyl-1H-pyrazol-3-yl)-4-(trifluoromethoxy)benzamide;
85. 3-chloro-N-(5-cyclopropyl-1H-pyrazol-3-yl)-1-benzothiophene-2-carboxamide;
86. 2-(4-chlorophenoxy)-N-(5-cyclopropyl-1H-pyrazol-3-yl)nicotinamide;
87. 3-chloro-N-(5-cyclopropyl-1H-pyrazol-3-yl)-2-thiophenecarboxamide;
88. N-(3-cyclopropyl-1H-pyrazol-5-yl)acetamide;
89. N-(3-cyclopropyl-1H-pyrazol-5-yl)benzamide;
90. 4-chloro-N-(3-cyclopropyl-1H-pyrazol-5-yl)benzamide;
91. N-(3-cyclopropyl-1H-pyrazol-5-yl)-1-benzothiophene-2-carboxamide;
92. N-(3-cyclopropyl-1H-pyrazol-5-yl)[1,1'-biphenyl]-4-carboxamide;
93. N-(3-cyclopropyl-1H-pyrazol-5-yl)-3-phenylpropanamide;
94. Methyl 4-{[(3-cyclopropyl-1H-pyrazol-5-yl)amino]carbonyl}benzoate;
95. 4-{[(3-cyclopropyl-1H-pyrazol-5-yl)amino]carbonyl}benzoic acid;
96. N-(3-cyclopropyl-1H-pyrazol-5-yl)-3-bromobenzamide;
97. N-(3-cyclopropyl-1H-pyrazol-5-yl)-3,4-dichlorobenzamide;
98. N-(3-cyclopropyl-1H-pyrazol-5-yl)-2-bromobenzamide;
99. N-(3-cyclopropyl-1H-pyrazol-5-yl)-3-methoxybenzamide;
100. N-(3-cyclopropyl-1H-pyrazol-5-yl)-3-trifluoromethylbenzamide;
101. 4-butoxy-N-(3-cyclopropyl-1H-pyrazol-5-yl)benzamide;
102. N-(3-cyclopropyl-1H-pyrazol-5-yl)-1H-indole-2-carboxamide;
103. N-(3-cyclopropyl-1H-pyrazol-5-yl)-2-[5-(2,6-difluorobenzyl)-2-methoxyphenyl]acetamide;
104. N'-(3-cyclopropyl-1H-pyrazol-5-yl)therephthalamide.
105. N-(5-cyclopropyl-1H-pyrazol-3-yl)-4-(3,3-dimethylbutanoyl)-1H-pyrrole-2-carboxamide;
106. N-(5-cyclopropyl-1H-pyrazol-3-yl)-4-(cyclopropylcarbonyl)-1H-pyrrole-2-carboxamide;
107. N-(5-cyclopropyl-1H-pyrazol-3-yl)-4-(2-thienylcarbonyl)-1H-pyrrole-2-carboxamide;
108. N-(5-cyclopropyl-1H-pyrazol-3-yl)-4-(2-methylbenzoyl)-1H-pyrrole-2-carboxamide;
109. 4-(1-benzothien-2-ylcarbonyl)-N-(5-cyclopropyl-1H-pyrazol-3-yl)-1H-pyrrole-2-carboxamide;
110. 2-[(4-acetylamino)phenyl]-N-(5-cyclopropyl-1H-pyrazol-3-yl)acetamide;
111. 4-bromo-N-(5-cyclopentyl-1H-pyrazol-3-yl)benzamide;
112. 4-bromo-N-(5-cycloHexyl-1H-pyrazol-3-yl)benzamide;
113. N-[5-(2-benzylcyclopropyl)-1H-pyrazol-3-yl]4-bromobenzamide;
114. 4-bromo-N-(5-cyclobutyl-1H-pyrazol-3-yl)benzamide;
115. N-(5-cyclopropyl-1H-pyrazol-3-yl)-2,4-dimethoxybenzamide;
116. N-(5-cyclopropyl-1H-pyrazol-3-yl)-4-(3-methylbenzoyl)-1H-pyrrole-2-carboxamide;
117. N-(5-cyclopropyl-1H-pyrazol-3-yl)-4-(3-methylbutanoyl)-1H-pyrrole-2-carboxamide;
118. N-(5-cyclopropyl-1H-pyrazol-3-yl)-4-(3-fluorobenzoyl)-1H-pyrrole-2-carboxamide;
119. N-(5-cyclopropyl-1H-pyrazol-3-yl)-4-(2-fluorobenzoyl)-1H-pyrrole-2-carboxamide;
120. 4-cyclopentylcarbonyl)-N-(5-cyclopropyl-1H-pyrazol-3-yl)-1H-pyrrole-2-carboxamide;
121. N-(5-cyclopropyl-1H-pyrazol-3-yl)-4-pentanoyl-1H-pyrrole-2-carboxamide;
122. 4-(3-chlorobenzoyl)-N-(5-cyclopropyl-1H-pyrazol-3-yl)-1H-pyrrole-2-carboxamide;
123. N-(5-cyclopropyl-1H-pyrazol-3-yl)-4-(phenylacetyl)-1H-pyrrole-2-carboxamide;
124. N-(5-cyclopropyl-1H-pyrazol-3-yl)-4-[(4-fluorophenyl)acetyl]-1H-pyrrole-2-carboxamide;
125. 4-butyryl-N-(5-cyclopropyl-1H-pyrazol-3-yl)-1H-pyrrole-2-carboxamide;
126. N-(5-cyclopropyl-1H-pyrazol-3-yl)-4-(4-fluorobenzoyl)-1H-pyrrole-2-carboxamide;
127. 2-(4-bromophenyl)-N-(5-cyclopropyl-1H-pyrazol-3-yl)-acetamide;
128. N-(5-cyclopropyl-1H-pyrazol-3-yl)-2-[4-(1-pyrrolidinyl)phenyl]acetamide;
129. (2S)-N-(5-cyclopropyl-1H-pyrazol-3-yl)-2-(2-naphtyl)propanamide;
130. N-(5-cyclopropyl-1H-pyrazol-3-yl)-2-(4$^1$-(hydroxymethyl)[1,1$^1$-biphenyl]-4-yl)acetamide;
131. 3-tert-butyl-N-(5-cyclopropyl-1H-pyrazol-3-yl)-1-(2-thienylcarbonyl)-1H-pyrazole-5-carboxamide;
132. N-(3-{[(3-cyclopropyl-1H-pyrazol-3-yl)amino]carbonyl}-2-thienyl)-2-thiophenecarboxamide;
133. N-(5-cyclopropyl-1H-pyrazol-3-yl)-5-(methylsulfonyl)-2-thiophenecarboxamide;
134. N-(5-cyclopropyl-1H-pyrazol-3-yl)-2-oxo-4-phenyl-3-butenamide;
135. N-5-cyclopropyl-1H-pyrazol-3-yl)-2-[4-(3-thienyl)phenyl]acetamide;
136. N-(5-cyclopropyl-1H-pyrazol-3-yl)-2-(4$^1$-fluoro[1$^{1,11}$-biphenyl]-4-yl)acetamide;
137. N-(5-cyclopropyl-1H-pyrazol-3-yl)-2,4-dimethyl-5-phenyl-1H-pyrrole-3-carboxamide;
138. N-(5-cyclopropyl-1H-pyrazol-3-yl)-2,5-dimethyl-1-(2-thienylmethyl)-1H-pyrrole-3-carboxamide;
139. N-(5-cyclopropyl-1H-pyrazol-3-yl)-2-methyl-5-phenyl-3-furamide;
140. N-{2-[(5-cyclopropyl-1H-pyrazol-3-yl)amino]-2-oxoethyl}benzamide;
141. N-(5-cyclopropyl-1H-pyrazol-3-yl)-2-(2-naphtyl)acetamide;
142. 5-chloro-N-(5-cyclopropyl-1H-pyrazol-3-yl)-2-thiophenecarboxamide;
143. 4$^1$-{2-[(5-cyclopropyl-1H-pyrazol-3-yl)amino]-2-oxoethyl}[1.1$^1$-biphenyl]-4-carboxylic acid;
144. 4$^1$-{2-[(5-cyclopropyl-1H-pyrazol-3-yl)amino]-2-oxethyl}[1,1$^1$-biphenyl]-4-carboxamide;
145. N-(5-cyclopropyl-1H-pyrazol-3-yl)-2-(4$^1$-formyl[1,1$^1$-biphenyl]-4-yl)acetamide;
146. N-(5-cyclopropyl-1H-pyrazol-3-yl)-2-{4$^1$-[(dimethylamino)methyl][1,1$^1$-biphenyl]-4-yl}acetamide;
147. 2-amino-N-(4-{2-[(5-cyclopropyl-1H-pyrazol-3-yl)amino]-2-oxethyl}phenyl)acetamide;
148. 2-4-aminomethyl)phenyl]-N-(5-cyclopropyl-1H-pyrazol-3-yl)acetamide;
149. 2-[4'-(aminomethyl)[1,1'-biphenyl]-4-yl]-N-(5-cyclopropyl-1H-pyrazol-3-yl)acetamide;
150. N-(5-cyclopropyl-1H-pyrazol-3-yl)-2-{4'-[(methylamino)methyl][1,1'-biphenyl]-4-yl}acetamide;
151. N-(5-cyclopropyl-1H-pyrazol-3-yl)-2-[4'-(1-pyrrolidinylmethyl)[1,1'-biphenyl]-4-yl]acetamide;

152. N-(5-cyclopropyl-1H-pyrazol-3-yl)-2-[4'-(1-piperidinylmethyl)[1,1'-biphenyl]-4-yl]acetamide;
153. N-(5-cyclopropyl-1H-pyrazol-3-yl)-2-[4'-(4-morpholinylmethyl)[1,1'-biphenyl]-4-yl]acetamide;
154. N-(5-cyclopropyl-1H-pyrazol-3-yl)-2-{4'-[(4-methyl-1-piperazinyl)methyl][1,1'-biphenyl]-4-yl}acetamide;
155. N-(5-cyclopropyl-1H-pyrazol-3-yl)-2-[4'-(1H-imidazol-2-yl)[1,1'-biphenyl]-4-yl]acetamide;
156. N-(5-cyclopropyl-1H-pyrazol-3-yl)-2-(4-{[(dimethylamino)carbonyl]amino}phenyl)acetamide;
157. N-(5-cyclopropyl-1H-pyrazol-3-yl)-2-{4-[(methylsulfonyl)amino]phenyl}acetamide;
158. 2-[4-(aminomethyl)phenyl]-N-(5-cyclopropyl-1H-pyrazol-3-yl)acetamide;
159. 2-{4-[(acetylamino)methyl]phenyl}-N-(5-cyclopropyl-1H-pyrazol-3-yl)acetamide;
160. 2-[4-(aminosulfonyl)phenyl]-N-(5-cyclopropyl-1H-pyrazol-3-yl)acetamide;
161. N-(5-cyclopropyl-1H-pyrazol-3-yl)-2-[4-(2-oxo-1-pyrrolidinyl)phenyl]acetamide;
162. N-(3-cyclopropyl-1H-pyrazol-5-yl)-4-(2-methoxyphenoxy)benzamide;
163. 4-(4-chlorophenoxy)-N-(3-cyclopropyl-1H-pyrazol-5-yl)benzamide;
164. 4-(4-chlorophenoxy)-N-(3-cyclopropyl-1H-pyrazol-5-yl)-3-nitrobenzamide;
165. 4-[3,5-bis(trifluoromethyl)phenoxy]-N-(3-cyclopropyl-1H-pyrazol-5-yl)benzamide;
166. N-(3-cyclopropyl-1H-pyrazol-5-yl)-4-(4-fluorophenoxy)benzamide;
167. N-(3-cyclopropyl-1H-pyrazol-5-yl)-4-(4-methylphenoxy)benzamide;
168. 4-(4-cyanophenoxy)-N-(3-cyclopropyl-1H-pyrazol-5-yl)benzamide;
169. N-(3-cyclopropyl-1H-pyrazol-5-yl)-4-(4-hydroxyphenoxy)benzamide;
170. N-(3-cyclopropyl-1H-pyrazol-5-yl)-4-(3-hydroxyphenoxy)benzamide;
171. 2-[1,1'-biphenyl]-4-yl-N-(3-cyclopropyl-1H-pyrazol-5-yl)propanamide;
172. N-(3-cyclopropyl-1H-pyrazol-5-yl)-2-(4-phenoxyphenyl)acetamide;
173. N-(3-cyclopropyl-1H-pyrazol-5-yl)-3,5-diiodo-4-(4-methoxyphenoxy)benzamide;
174. N-(3-cyclopropyl-1H-pyrazol-5-yl)-4-[3-(hydroxymethyl)phenyl]-3-butenamide;
175. N-(3-cyclopropyl-1H-pyrazol-5-yl)-4-{3-[(methylamino)methyl]phenyl}-3-butenamide;
176. N-(3-cyclopropyl-1H-pyrazol-5-yl)-2-(2-phenylcyclopropyl)acetamide;
177. 2-[2-(1,3-benzodioxol-5-yl)cyclopropyl]-N-(3-cyclopropyl-1H-pyrazol-5-yl)acetamide;
178. 2-[3-(1,3-benzodioxol-5-yl)-2,2-difluorocyclopropyl]-N-(3-cyclopropyl-1H-pyrazol-5-yl)acetamide;
179. N-(3-cyclopropyl-1H-pyrazol-5-yl)-2-(2,2-difluoro-3-phenylcyclopropyl)acetamide;
180. N-(3-cyclopropyl-1H-pyrazol-5-yl)-2-(5-methyl-4-phenyl-3-isoxazolyl)acetamide;
181. N-(3-cyclopropyl-1H-pyrazol-5-yl)-2-(5-methyl-3-phenyl-4-isoxazolyl)acetamide;
182. 2-[3-(1,3-benzodioxol-5-yl)-5-methyl-4-isoxazolyl]-N-(3-cyclopropyl-1H-pyrazol-5-yl)acetamide;
183. 2-[4-(1,3-benzodioxol-5-yl)-5-methyl-3-isoxazolyl]-N-(3-cyclopropyl-1H-pyrazol-5-yl)acetamide;
184. N-(5-cyclopropyl-1H-pyrazol-3-yl)-2-(3-phenyl-2-oxiranyl)acetamide;
185. N-(3-cyclopropyl-1H-pyrazol-5-yl)-2-[2-(4-fluorophenyl)cyclopropyl]acetamide;
186. N-(3-cyclopropyl-1H-pyrazol-5-yl)-2-[2,2-difluoro-3-(3-fluorophenyl)cyclopropyl]acetamide;
187. N-(3-cyclopropyl-1H-pyrazol-5-yl)-2-(2-oxo-2,3-dihydro-1H-indol-5-yl)acetamide;
188. 2-[4-(acetylamino)phenyl]-N-(3-cyclopropyl-1H-pyrazol-5-yl)acetamide;
189. N-(4-{2-[(3-cyclopropyl-1H-pyrazol-5-yl)amino]-2-oxoethyl}phenyl)-1-pyrrolidinecarboxamide;
190. N-(4-{2-[(3-cyclopropyl-1H-pyrazol-5-yl)amino]-2-oxoethyl}phenyl)-1-piperidinecarboxamide;
191. N-(4-{2-[(3-cyclopropyl-1H-pyrazol-5-yl)amino]-2-oxoethyl}phenyl)-4-morpholinecarboxamide;
192. N-(4-{2-[(3-cyclopropyl-1H-pyrazol-5-yl)amino]-2-oxoethyl}phenyl)-4-methyl-1-piperazinecarboxamide;
193. N-(3-cyclopropyl-1H-pyrazol-5-yl)-2-(2-pyridinyl)acetamide;
194. N-(3-cyclopropyl-1H-pyrazol-5-yl)-2-(3-pyridinyl)acetamide;
195. N-(3-cyclopropyl-1H-pyrazol-5-yl)-2-(4-pyridinyl)acetamide;
196. N-(3-cyclopropyl-1H-pyrazol-5-yl)-5-(3-nitrophenyl)-2-furamide;
197. N-(3-cyclopropyl-1H-pyrazol-5-yl)-2-(2,5-dioxo-4-imidazolidinyl)acetamide;
198. N-(5-cyclopropyl-1H-pyrazol-3-yl)-2-(9-oxo-9H-fluoren-2-yl)acetamide;
199. N-(5-cyclopropyl-1H-pyrazol-3-yl)-2-(4'-ethyl[1,1'-biphenyl]-4-yl)acetamide;
200. N-(5-cyclopropyl-1H-pyrazol-3-yl)-2-(4'-propyl[1,1'-biphenyl]-4-yl)acetamide;
201. N-(5-cyclopropyl-1H-pyrazol-3-yl)-2-(9H-fluoren-2-yl)acetamide;
202. N-(5-cyclopropyl-1H-pyrazol-3-yl)-2-(9-methyl-9H-fluoren-2-yl)acetamide;
203. N-(5-cyclopropyl-1H-pyrazol-3-yl)-2-(2-hydroxydibenzo[b,d]furan-3-yl)acetamide;
204. N-(5-cyclopropyl-1H-pyrazol-3-yl)-2-(4'-hydroxy[1,1'-biphenyl]-4-yl)acetamide;
205. 2-(4'-cyano[1,1'-biphenyl]-4-yl)-N-(5-cyclopropyl-1H-pyrazol-3-yl)acetamide;
206. 2-(4'-bromo[1,1'-biphenyl]-4-yl)-N-(5-cyclopropyl-1H-pyrazol-3-yl)acetamide;
207. N-(5-cyclopropyl-1H-pyrazol-3-yl)-2-(4'-propoxy[1,1'-biphenyl]-4-yl)acetamide;
208. N-(5-cyclopropyl-1H-pyrazol-3-yl)-2-(4'-butoxy[1,1'-biphenyl]-4-yl)acetamide;
209. N-(5-cyclopropyl-1H-pyrazol-3-yl)-2-(4'-pentoxy[1,1'-biphenyl]-4-yl)acetamide;
210. 4'-{2-[(5-cyclopropyl-1H-pyrazol-3-yl)amino]-2-oxoethyl}[1,1'-biphenyl]-4-yl acetate;
211. 2-(4'-tert-butyl[1,1'-biphenyl]-4-yl)-N-(5-cyclopropyl-1H-pyrazol-3-yl)acetamide;
212. N-(5-cyclopropyl-1H-pyrazol-3-yl)-2-(3',4'-dichloro[1,1'-biphenyl]-4-yl)acetamide;
213. N-(5-cyclopropyl-1H-pyrazol-3-yl)-2-(3'-hydroxy[1,1'-biphenyl]-4-yl)acetamide;
214. 2-(3'-bromo[1,1'-biphenyl]-4-yl)-N-(5-cyclopropyl-1H-pyrazol-3-yl)acetamide;
215. 2-(3'-amino[1,1'-biphenyl]-4-yl)-N-(5-cyclopropyl-1H-pyrazol-3-yl)acetamide;
216. 2-(4'-amino[1,1'-biphenyl]-4-yl)-N-(5-cyclopropyl-1H-pyrazol-3-yl)acetamide;
217. N-(5-cyclopropyl-1H-pyrazol-3-yl)-2-(3-hydroxy-2-naphthyl)acetamide;

218. N-(5-cyclopropyl-1H-pyrazol-3-yl)-2-(3,5-dihydroxy-2-naphthyl)acetamide;
219. 2-(3-amino-2-naphthyl)-N-(5-cyclopropyl-1H-pyrazol-3-yl)acetamide;
220. N-(5-cyclopropyl-1H-pyrazol-3-yl)-2-(6-hydroxy-2-naphthyl)acetamide;
221. N-(5-cyclopropyl-1H-pyrazol-3-yl)-2-(2-hydroxy-1-naphthyl)acetamide;
222. N-(5-cyclopropyl-1H-pyrazol-3-yl)-2-(6-hydroxy-1-naphthyl)acetamide;
223. 3-amino-N-(5-cyclopropyl-1H-pyrazol-3-yl)-4-[(2-furylmethyl)sulfonyl]-2-thiophenecarboxamide;
224. 3-amino-4-[(4-chlorophenyl)sulfonyl]-N-(5-cyclopropyl-1H-pyrazol-3-yl)-2-thiophenecarboxamide;
225. 3-amino-N-(5-cyclopropyl-1H-pyrazol-3-yl)-4-(phenylsulfonyl)-2-thiophenecarboxamide;
226. 3-chloro-N-(5-cyclopropyl-1H-pyrazol-3-yl)-4-(methylsulfonyl)-2-thiophenecarboxamide;
227. 3-amino-N-(5-cyclopropyl-1H-pyrazol-3-yl)-4-(isopropylsulfonyl)-2-thiophenecarboxamide;
228. 3-amino-N-(5-cyclopropyl-1H-pyrazol-3-yl)-4-(propylsulfonyl)-2-thiophenecarboxamide;
229. 3-chloro-N-(5-cyclopropyl-1H-pyrazol-3-yl)-4-(isopropylsulfonyl)-2-thiophenecarboxamide;
230. N-(5-cyclopropyl-1H-pyrazol-3-yl)-4-(isopropylsulfonyl)-2-thiophenecarboxamide;
231. 4-{2-[(5-cyclopropyl-1H-pyrazol-3-yl)amino]-2-oxoethyl}benzamide;
232. 4'-{2-[(5-cyclopropyl-1H-pyrazol-3-yl)amino]-2-oxoethyl}-N-[2-(1-pyrrolidinyl)ethyl][1,1'-biphenyl]-4-carboxamide;
233. 4'-{2-[(5-cyclopropyl-1H-pyrazol-3-yl)amino]-2-oxoethyl}-N-[2-(1-pyrrolidinyl)propyl][1,1'-biphenyl]-4-carboxamide;
234. 4'-{2-[(5-cyclopropyl-1H-pyrazol-3-yl)amino]-2-oxoethyl}-N-[2-(1-piperidinyl)ethyl][1,1'-biphenyl]-4-carboxamide;
235. 4'-{2-[(5-cyclopropyl-1H-pyrazol-3-yl)amino]-2-oxoethyl}-N-[2-(1-piperidinyl)propyl][1,1'-biphenyl]-4-carboxamide;
236. 4'-{2-[(5-cyclopropyl-1H-pyrazol-3-yl)amino]-2-oxoethyl}-N-[2-(4-morpholinyl)ethyl][1,1'-biphenyl]-4-carboxamide;
237. 4'-{2-[(5-cyclopropyl-1H-pyrazol-3-yl)amino]-2-oxoethyl}-N-[2-(4-morpholinyl)propyl][1,1'-biphenyl]-4-carboxamide;
238. 4'-{2-[(5-cyclopropyl-1H-pyrazol-3-yl)amino]-2-oxoethyl}-N-[2-(4-methyl-1-piperazinyl)ethyl][1,1'-biphenyl]-4-carboxamide;
239. 4'-{2-[(5-cyclopropyl-1H-pyrazol-3-yl)amino]-2-oxoethyl}-N-[2-(4-methyl-1-piperazinyl)propyl][1,1'-biphenyl]-4-carboxamide;
240. N-(3-cyclopropyl-1H-pyrazol-5-yl)-4-(3,4-dimethylbenzoyl)-1H-pyrrole-2-carboxamide;
241. N-(3-cyclopropyl-1H-pyrazol-5-yl)-4-(4-fluorobenzoyl)-1H-pyrrole-2-carboxamide;
242. N-(3-cyclopropyl-1H-pyrazol-5-yl)-4-(4-methylbenzoyl)-1H-pyrrole-2-carboxamide;
243. 4-(4-chlorobenzoyl)-N-(3-cyclopropyl-1H-pyrazol-5-yl)-1H-pyrrole-2-carboxamide;
244. 4-(cyclohexylcarbonyl)-N-(3-cyclopropyl-1H-pyrazol-5-yl)-1H-pyrrole-2-carboxamide;
245. methyl 5-(5-{[(3-cyclopropyl-1H-pyrazol-5-yl)amino]carbonyl}-1H-pyrrol-3-yl)-5-oxopentanoate
246. 4-acetyl-N-(3-cyclopropyl-1H-pyrazol-5-yl)-1H-pyrrole-2-carboxamide;
247. N-(3-cyclopropyl-1H-pyrazol-5-yl)-4-(2,6-dimethoxybenzoyl)-1H-pyrrole-2-carboxamide;
248. N-(3-cyclopropyl-1H-pyrazol-5-yl)-1H-pyrrole-2-carboxamide;
249. N-(3-cyclobutyl-1H-pyrazol-5-yl)-1H-pyrrole-2-carboxamide
250. N-(3-cyclopropyl-1H-pyrazol-5-yl)-1-methyl-1H-pyrrole-2-carboxamide;
251. 4-bromo-N-(3-cyclopropyl-1H-pyrazol-5-yl)-1H-pyrrole-2-carboxamide;
252. N-(3-cyclopropyl-1H-pyrazol-5-yl)-1-methyl-4-(3-methylbenzoyl)-1H-pyrrole-2-carboxamide;
253. N-(3-cyclopropyl-1H-pyrazol-5-yl)-2-quinoxalinecarboxamide;
254. (1R,2R)-N-(3-cyclopropyl-1H-pyrazol-5-yl)-2-phenylcyclopropanecarboxamide;
255. N-(3-cyclopropyl-1H-pyrazol-5-yl)-2-phenylcyclopropanecarboxamide;
256. 3-chloro-N-(3-cyclopropyl-1H-pyrazol-5-yl)-2-thiophenecarboxamide;
257. 4-benzoyl-N-(3-cyclopropyl-1H-pyrazol-5-yl)benzamide;
258. (2S)-N-(5-cyclopropyl-1H-pyrazol-3-yl)-2-(6-methoxy-2-naphthyl)propanamide;
259. N-(3-cyclopropyl-1H-pyrazol-5-yl)-4-morpholinocarboxamide;
260. (2S)-N-(3-cyclopropyl-1H-pyrazol-5-yl)-3,3,3-trifluoro-2-methoxy-2-phenylpropanamide;
261. (2S)-N-(3-cyclopropyl-1H-pyrazol-5-yl)-2-methoxy-2-phenylethanamide;
262. 2-[5-(benzyloxy)-1H-indol-3-yl]-N-(5-cyclopropyl-1H-pyrazol-3-yl)acetamide;
263. N-(5-cyclopropyl-1H-pyrazol-3-yl)-2-(5-methoxy-2-methyl-1H-indol-3-yl)acetamide;
264. (2S)-N-(3-cyclopropyl-1H-pyrazol-5-yl)-2,5-dihydro-1H-pyrrole-2-carboxamide;
265. N-(5-cyclopropyl-1H-pyrazol-3-yl)-2-(2,5-difluorophenyl)acetamide;
266. N-(5-cyclopropyl-1H-pyrazol-3-yl)-2-(5-hydroxy-1H-indole-3-yl)acetamide;
267. 2-[1-(4-chlorobenzoyl)-5-methoxy-2-methyl-1H-indol-3-yl]-N-(5-cyclopropyl-1H-pyrazol-3-yl)acetamide;
268. N-(5-cyclopropyl-1H-pyrazol-3-yl)-2-(3-methylphenyl)acetamide;
269. N-(5-cyclopropyl-1H-pyrazol-3-yl)-2-(3-hydroxyphenyl)acetamide;
270. (2S)-2-amino-N-(3-cyclopropyl-1H-pyrazol-5-yl)-2-phenylethanamide;
271. N-(5-cyclopropyl-1H-pyrazol-3-yl)-2-(4-nitrophenyl)propanamide;
272. N-(5-cyclopropyl-1H-pyrazol-3-yl)-2-(4-hydroxy-3-methoxyphenyl)acetamide;
273. N-(5-cyclopropyl-1H-pyrazol-3-yl)-2-[3,5-bis(trifluoromethyl)phenyl]acetamide;
274. N-(5-cyclopropyl-1H-pyrazol-3-yl)-2-(2-chloro-6-fluorophenyl)acetamide;
275. N-(5-cyclopropyl-1H-pyrazol-3-yl)-2-hydroxy-2-(4-hydroxy-3-methoxyphenyl)acetamide;
276. N-(5-cyclopropyl-1H-pyrazol-3-yl)-2-{4-[(2S)-2-aminopropanoyloxymethyl]phenyl}acetamide;
277. N-(5-cyclopropyl-1H-pyrazol-3-yl)-2-(4-bromomethylphenyl)acetamide;
278. N-(5-cyclopropyl-1H-pyrazol-3-yl)-2-(4-methylsulphonylphenyl)acetamide;
279. (2R)-N-(3-cyclopropyl-1H-pyrazol-5-yl)-2-methoxy-2-phenylethanamide;

280. N-(5-cyclopropyl-1H-pyrazol-3-yl)-2-(2-methylphenyl)acetamide;
281. N-(5-cyclopropyl-1H-pyrazol-3-yl)-2-[2-(formylamino)-1,3-thiazol-4-yl]-2-(methoxyimino)ethanamide;
282. 2-[5-(chloroacetyl)-2-thienyl]-N-(5-cyclopropyl-1H-pyrazol-3-yl)acetamide;
283. N-(3-cyclopropyl-1H-pyrazol-5-yl)-2-oxo-2-(2-thienyl)acetamide;
284. N-(5-cyclopropyl-1H-pyrazol-3-yl)-2-(2-methyl-1H-indol-3-yl)acetamide;
285. N-(5-cyclopropyl-1H-pyrazol-3-yl)-2-(3,5-dimethoxyphenyl)acetamide;
286. N-(5-cyclopropyl-1H-pyrazol-3-yl)-2-(3,4-difluorophenyl)acetamide;
287. N-(5-cyclopropyl-1H-pyrazol-3-yl)-2-(3,4-dichlorophenyl)acetamide;
288. N-(5-cyclopropyl-1H-pyrazol-3-yl)-2-(3-bromophenyl)acetamide;
289. 2-cyclohexyl-N-(3-cyclopropyl-1H-pyrazol-5-yl)-2-phenylacetamide;
290. (1R)-2-[(3-cyclopropyl-1H-pyrazol-5-yl)amino]-2-oxo-1-phenylethyl acetate;
291. 2-chloro-N-(5-{2-[(5-cyclopropyl-1H-pyrazol-3-yl)amino]-2-oxoethyl}-1,3-thiazol-2-yl)acetamide;
292. 9H-fluoren-9-yl (2S)-2-{[(3-cyclopropyl-1H-pyrazol-5-yl)amino]carbonyl}-2,5-dihydro-1H-pyrrole-1-carboxylate;
293. N-(5-cyclopropyl-1H-pyrazol-3-yl)-2-(2-hydroxy-2-diphenyl)acetamide;
294. N-(5-cyclopropyl-1H-pyrazol-3-yl)-2-(4-methylsulfanylphenyl)acetamide;
295. N-(5-cyclopropyl-1H-pyrazol-3-yl)-2-(2-bromophenyl)acetamide;
296. N-(5-cyclopropyl-1H-pyrazol-3-yl)-2-(2,6-dihydroxy-4-pyrimidinyl)acetamide;
297. N-(5-cyclopropyl-1H-pyrazol-3-yl)-2-(4-hydroxy-3-nitrophenyl)acetamide;
298. N-(5-cyclopropyl-1H-pyrazol-3-yl)-2-(3-chloro-4-hydroxyphenyl)acetamide;
299. N-(5-cyclopropyl-1H-pyrazol-3-yl)-2-(7-methoxy-2-oxo-2H-chromen-4-yl)acetamide;
300. N-(5-cyclopropyl-1H-pyrazol-3-yl)-2-(2-acetylamino-2-phenyl)acetamide;
301. N-(5-cyclopropyl-1H-pyrazol-3-yl)-2-(1-methylimidazol-4-yl)acetamide;
302. N-(5-cyclopropyl-1H-pyrazol-3-yl)-2-(3-nitrophenyl)acetamide;
303. N-(5-cyclopropyl-1H-pyrazol-3-yl)-2-(2-bromo-2-phenyl)acetamide;
304. N-(5-cyclopropyl-1H-pyrazol-3-yl)-2-(4-benzyloxy-3-methoxyphenyl)acetamide;
305. (2S)-N-(5-cyclopropyl-1H-pyrazol-3-yl)-2-hydroxy-2-phenylethanamide;
306. 1-(4-chlorophenyl)-N-(5-cyclopropyl-1H-pyrazol-3-yl)cyclopentanecarboxamide;
307. N-(5-cyclopropyl-1H-pyrazol-3-yl)-2-(3-trifluoromethylphenyl)acetamide;
308. N-(5-cyclopropyl-1H-pyrazol-3-yl)-2-(1H-indol-3-yl)-2-oxoacetamide;
309. N-(5-cyclopropyl-1H-pyrazol-3-yl)-2-(2,4-dichlorophenyl)acetamide;
310. N-(5-cyclopropyl-1H-pyrazol-3-yl)-2-(3,4-dihydroxyphenyl)acetamide;
311. N-(5-cyclopropyl-1H-pyrazol-3-yl)-2-(3,5-di-tert-butyl-4-hydroxyphenyl)acetamide;
312. N-(5-cyclopropyl-1H-pyrazol-3-yl)-2-(3,5-difluorophenyl)acetamide;
313. N-(5-cyclopropyl-1H-pyrazol-3-yl)-2-benzyloxycarbonyl-2-phenylacetamide;
314. N-(5-cyclopropyl-1H-pyrazol-3-yl)-2-(3-methyl-1-benzothien-2-yl)acetamide;
315. N-(5-cyclopropyl-1H-pyrazol-3-yl)-2-(4-butoxyphenyl)acetamide;
316. N-(5-cyclopropyl-1H-pyrazol-3-yl)-2-(2-thienyl)acetamide;
317. N-(5-cyclopropyl-1H-pyrazol-3-yl)-2-(3-fluorophenyl)acetamide;
318. 5-cyclohexyl 1-(4-{2-[(5-cyclopropyl-1H-pyrazol-3-yl)amino]-2-oxoethyl}benzyl) 2-aminopentanedioate;
319. N-(5-cyclopropyl-1H-pyrazol-3-yl)-2-(4-isobutylphenyl)propanamide;
320. N-(5-cyclopropyl-1H-pyrazol-3-yl)-2-(7-hydroxy-2-oxo-2H-chromen-4-yl)acetamide;
321. N-(5-cyclopropyl-1H-pyrazol-3-yl)-2-(4-hydroxyphenyl)acetamide;
322. 2-cyclopentyl-N-(5-cyclopropyl-1H-pyrazol-3-yl)-2-phenylacetamide;
323. (1S)-2-[(3-cyclopropyl-1H-pyrazol-5-yl)amino]-2-oxo-1-phenylethyl acetate;
324. N-(3-cyclopropyl-1H-pyrazol-5-yl)-2-fluoro-2-phenylacetamide;
325. N-(5-cyclopropyl-1H-pyrazol-3-yl)-2-(2-furyl)-2-oxoacetamide;
326. N-(5-cyclopropyl-1H-pyrazol-3-yl)-2-(5-bromo-1H-indol-3-yl)acetamide;
327. N-(5-cyclopropyl-1H-pyrazol-3-yl)-2-(2-trifluoromethylphenyl)acetamide;
328. N-(5-cyclopropyl-1H-pyrazol-3-yl)-2-(2-methoxyphenyl)acetamide;
329. N-(5-cyclopropyl-1H-pyrazol-3-yl)-2-(3,4,5-trimethoxyphenyl)acetamide;
330. N-(5-cyclopropyl-1H-pyrazol-3-yl)-2-(2,5-dioxo-2,5-dihydro-3-furanyl)acetamide;
331. 2-chloro-2,2-bis(2-chlorophenyl)-N-(5-cyclopropyl-1H-pyrazol-3-yl)acetamide;
332. N-(5-cyclopropyl-1H-pyrazol-3-yl)-2-hydroxy-2-(3-hydroxy-4-methoxyphenyl)acetamide;
333. N-(5-cyclopropyl-1H-pyrazol-3-yl)-2-(pentafluorophenyl)acetamide;
334. N-(3-cyclopropyl-1H-pyrazol-5-yl)-3-methyl-2-phenylpentamide;
335. N-(5-cyclopropyl-1H-pyrazol-3-yl)-2-(2-nitrophenyl)acetamide;
336. N-(5-cyclopropyl-1H-pyrazol-3-yl)-1-phenylcyclopentane-1-carboxamide;
337. N-(5-cyclopropyl-1H-pyrazol-3-yl)-2-(4-trifluoromethoxyphenyl)acetamide;
338. N-(5-cyclopropyl-1H-pyrazol-3-yl)-2-(4-ethoxyphenyl)acetamide;
339. N-(5-cyclopropyl-1H-pyrazol-3-yl)-2-(2-fluorophenyl)acetamide;
340. N-(5-cyclopropyl-1H-pyrazol-3-yl)-2-(2-nitro-4-trifluoromethylphenyl)acetamide;
341. 2-(5-bromo-3-pyridinyl)-N-(5-cyclopropyl-1H-pyrazol-3-yl)acetamide;
342. N-(5-cyclopropyl-1H-pyrazol-3-yl)-2-(2,6-dichlorophenyl)acetamide;
343. N-(5-cyclopropyl-1H-pyrazol-3-yl)-2-oxo-2H-pyran-5-carboxamide;
344. N-(5-cyclopropyl-1H-pyrazol-3-yl)-2-(2,4-dinitrophenyl)acetamide;
345. N-(5-cyclopropyl-1H-pyrazol-3-yl)-2,4-difluorophenylacetamide;

346. N-(5-cyclopropyl-1H-pyrazol-3-yl)-2-(3-bromo-4-methoxyphenyl)acetamide;
347. N-(5-cyclopropyl-1H-pyrazol-3-yl)-3-hydroxy-2-phenylpropanamide;
348. N-(5-cyclopropyl-1H-pyrazol-3-yl)-2-(3-fluoro-4-hydroxyphenyl)acetamide;
349. 2-{2-[(chloroacetyl)amino]-1,3-thiazol-5-yl}-N-(5-cyclopropyl-1H-pyrazol-3-yl)-2-(methoxyimino)ethanamide;
350. N-(5-cyclopropyl-1H-pyrazol-3-yl)-1-phenylcyclopropanecarboxamide;
351. N-(5-cyclopropyl-1H-pyrazol-3-yl)-2-(2,6-difluorophenyl)acetamide;
352. N-(5-cyclopropyl-1H-pyrazol-3-yl)-2-(2,5-dihydroxyphenyl)acetamide;
353. N-(5-cyclopropyl-1H-pyrazol-3-yl)-2-(2,4,6-trimethylphenyl)acetamide;
354. N-(5-cyclopropyl-1H-pyrazol-3-yl)-2-[2,5-bis(trifluoromethyl)phenyl]acetamide;
355. N-(5-cyclopropyl-1H-pyrazol-3-yl)-2-[2-(2,4-difluorophenyl)-1,3-thiazol-4-yl]acetamide;
356. N-(5-cyclopropyl-1H-pyrazol-3-yl)-2-(5-methoxy-3-hydroxy-2-propylphenyl)acetamide;
357. N-(3-cyclopropyl-1H-pyrazol-5-yl)-2-(2-fluoro-[1,1'-biphenyl]-4-yl)propanamide;
358. (2R)-N-(3-cyclopropyl-1H-pyrazol-5-yl)-2-(2-fluoro[1,1'-biphenyl]-4-yl)propanamide;;
359. 2-{4-[(aminocarbonyl)amino]phenyl}-N-(5-cyclopropyl-1H-pyrazol-3-yl)acetamide;
360. 2-{4-[(2-amino-2-oxoethyl)amino]phenyl}-N-(5-cyclopropyl-1H-pyrazol-3-yl)acetamide;
361. N-(5-cyclopropyl-1H-pyrazol-3-yl)-2-(5-methyl-2-phenyl-1,3-thiazol-4-yl)acetamide;
362. 4-bromo-N-(4-{2-[(5-cyclopropyl-1H-pyrazol-3-yl)amino]-2-oxoethyl}-1,3-thiazol-2-yl)benzamide
363. 2-[2-(4-chlorophenyl)-4-hydroxy-1,3-thiazol-5-yl]-N-(5-cyclopropyl-1H-pyrazol-3-yl)acetamide;
364. N-(4-{2-[(5-cyclopropyl-1H-pyrazol-3-yl)amino]-2-oxoethyl}-1,3-thiazol-2-yl)-2-(2-pyridinylsulfanyl)acetamide;
365. N-(4-{2-[(5-cyclopropyl-1H-pyrazol-3-yl)amino]-2-oxoethyl}-1,3-thiazol-2-yl)-2-(isopropylsulfanyl)acetamide;
366. 2-(5-{[(4-chlorophenyl)sulfanyl]acetyl}-2-thienyl)-N-(5-cyclopropyl-1H-pyrazol-3-yl)acetamide;
367. 2-(5-chloro-3-methyl-1-benzothien-2-yl)-N-(5-cyclopropyl-1H-pyrazol-3-yl)acetamide;
368. N-(5-cyclopropyl-1H-pyrazol-3-yl)-2-(2-iodophenyl)acetamide;
369. N-(5-cyclopropyl-1H-pyrazol-3-yl)-9H-xanthene-9-carboxamide;
370. N-(5-cyclopropyl-1H-pyrazol-3-yl)-2-(2-phenyl-1,3-thiazol-4-yl)acetamide;
371. 2-[2-(4-chlorophenyl)-5-methyl-1,3-thiazol-4-yl]-N-(5-cyclopropyl-1H-pyrazol-3-yl)acetamide;
372. N-(4-{2-[(5-cyclopropyl-1H-pyrazol-3-yl)amino]-2-oxoethyl}-1,3-thiazol-2-yl)benzamide;
373. N-(5-cyclopropyl-1H-pyrazol-3-yl)-2-(6-methoxy-2-naphthyl)acrylamide;
374. N-(5-cyclopropyl-1H-pyrazol-3-yl)-2-(2-hydroxyphenyl)acetamide;
375. N-(5-cyclopropyl-1H-pyrazol-3-yl)-2,3-di(2-thienyl)-2-propenamide;
376. N-(5-cyclopropyl-1H-pyrazol-3-yl)-2-[2-(2-pyrazinyl)-1,3-thiazol-4-yl]acetamide;
377. N-(5-cyclopropyl-1H-pyrazol-3-yl)-2-(2,5-dibromo-3-thienyl)acetamide;
378. N-(5-cyclopropyl-1H-pyrazol-3-yl)-2-(3-methylsulfonaylaminophenyl)acetamide;
379. N-(5-cyclopropyl-1H-pyrazol-3-yl)-2-(4-methylsulfonaylaminophenyl)acetamide;
380. N-(5-cyclopropyl-1H-pyrazol-3-yl)-2-{4-[2-(4-methyl-1-piperazinyl)ethoxy]phenyl}acetamide;
381. N-(5-cyclopropyl-1H-pyrazol-3-yl)-2-{4-[2-(1-pyrrolidinyl)ethoxy]phenyl}acetamide;
382. N-(5-cyclopropyl-1H-pyrazol-3-yl)-2-{4-(amino-2-oxoethoxy)phenyl}acetamide;
383. N-(5-cyclopropyl-1H-pyrazol-3-yl)-2-{4-[2-oxo-2-(1-pyrrolidinyl)ethoxy]phenyl}acetamide;
384. N-(5-cyclopropyl-1H-pyrazol-3-yl)-2-[3-(2-amino-2-oxoethoxy)phenyl]acetamide;
385. N-(5-cyclopropyl-1H-pyrazol-3-yl)-2-phenoxyacetamide;
386. N-(5-cyclopropyl-1H-pyrazol-3-yl)-2-(2,4-dichlorophenoxy)acetamide;
387. N-(5-cyclopropyl-1H-pyrazol-3-yl)-2-phenoxy-2-methylpropanamide;
388. N-(5-cyclopropyl-1H-pyrazol-3-yl)-2-(4-chlorophenoxy)propanamide;
389. N-(5-cyclopropyl-1H-pyrazol-3-yl)-2-(2-nitrophenoxy)acetamide;
390. N-(5-cyclopropyl-1H-pyrazol-3-yl)-2-(5-isopropyl-2-methyl-1H-indol-3-yl)acetamide;
391. N-(5-cyclopropyl-1H-pyrazol-3-yl)-2-(3-methoxyphenyl)acetamide;
392. N-(5-cyclopropyl-1H-pyrazol-3-yl)-2-methyl-2-(2-methyl-2,3-dihydro-1-benzofuran-5-yl)propanamide;
393. N-(5-cyclopropyl-1H-pyrazol-3-yl)-2-[2-(4-methoxyphenyl)-4-oxo-4H-chromen-6-yl]acetamide;
394. N-(5-cyclopropyl-1H-pyrazol-3-yl)-2-(6-chloro-2,3-dihydro-1H-inden-3-yl)butanamide;
395. N-(5-cyclopropyl-1H-pyrazol-3-yl)-2-[4-(1-oxo-1,3-dihydro-2H-isoindol-2-yl)phenyl]hexanamide;
396. N-(5-cyclopropyl-1H-pyrazol-3-yl)-2-phenyl-3-(4-pyridinyl)propenamide;
397. 2-[1,1'-biphenyl]-4-yl-N-(5-cyclopropyl-1H-pyrazol-3-yl)butanamide;
398. N-(5-cyclopropyl-1H-pyrazol-3-yl)-2-[4-(1,3-dihydro-2H-isoindol-2-yl)phenyl]propanamide;
399. N-(5-cyclopropyl-1H-pyrazol-3-yl)-2-[4-(1-oxo-1,3-dihydro-2H-isoindol-2-yl)phenyl]butanamide;
400. N-(5-cyclopropyl-1H-pyrazol-3-yl)-(2S)-2-[4-(1-oxo-1,3-dihydro-2H-isoindol-2-yl)phenyl]propanamide;
401. N-(5-cyclopropyl-1H-pyrazol-3-yl)-2-[4-(5-amino-4-phenyl-1H-1,2,3-triazol-1-yl)phenyl]acetamide;
402. N-(5-cyclopropyl-1H-pyrazol-3-yl)-2-[4-(1-oxo-1,3-dihydro-2H-isoindol-2-yl)phenyl]pentanamide;
403. N-(5-cyclopropyl-1H-pyrazol-3-yl)-2-(4-benzyloxyphenyl)acetamide;
404. N-(5-cyclopropyl-1H-pyrazol-3-yl)-2-{4-[(3,3-diethyl-4-oxo-2-azetidinyl)oxy]phenyl}acetamide;
405. N-(5-cyclopropyl-1H-pyrazol-3-yl)-2-(5,6-dimethyl-1H-benzimidazol-1-yl)acetamide;
406. N-(5-cyclopropyl-1H-pyrazol-3-yl)-2-(4-pyridylsulfanyl)acetamide;
407. N-(5-cyclopropyl-1H-pyrazol-3-yl)-2-(1H-tetrazol-1-yl)acetamide;
408. N-(5-cyclopropyl-1H-pyrazol-3-yl)-2-(tetrazolo[1,5-b]pyridazin-6-ylsulfanyl)acetamide;
409. 2-[1,1'-biphenyl]-4-yl-N-(5-cyclopropyl-1H-pyrazol-3-yl)-2-hydroxyacetamide;
410. N-(5-cyclopropyl-1H-pyrazol-3-yl)-2-cyclohexene-1-carboxamide;

411. N-(5-cyclopropyl-1H-pyrazol-3-yl)-2-oxo-2H-pyran-4-carboxamide;
412. N-(5-cyclopropyl-1H-pyrazol-3-yl)-3-bromo-2,2-diphenylpropanamide;
413. N-(5-cyclopropyl-1H-pyrazol-3-yl)-4,4-bis(4-methylphenyl)-3-butenamide;
414. N-(5-cyclopropyl-1H-pyrazol-3-yl)-2-(4-hydroxy-5-isopropyl-2-methylphenyl)acetamide;
415. N-(5-cyclopropyl-1H-pyrazol-3-yl)-2-(4-nitrophenyl)-2-butenamide;
416. N-(5-cyclopropyl-1H-pyrazol-3-yl)-2-(3,4-dihydro-1-naphthyl)butanamide;
417. N-(5-cyclopropyl-1H-pyrazol-3-yl)-2-(2,3,6-trifluorophenyl)acetamide;
418. N-(3-cyclopropyl-1H-pyrazol-5-yl)-1,4-benzodioxine-2-carboxamide;
419. N-(3-cyclopropyl-1H-pyrazol-5-yl)-3-phenyl-1,4-benzodioxine-2-carboxamide;
420. N-(3-cyclopropyl-1H-pyrazol-5-yl)-4-oxo-4H-chromene-2-carboxamide;
421. N-(3-cyclopropyl-1H-pyrazol-5-yl)-2-oxo-1,2-dihydro-4-quinolinecarboxamide;
422. 2-anilino-N-(3-cyclopropyl-1H-pyrazol-5-yl)acetamide;
423. N-(5-cyclopropyl-1H-pyrazol-3-yl)-2-(4'-fluoro[1,1'-biphenyl]-4-yl)acetamide
424. N-(5-cyclopropyl-1H-pyrazol-3-yl)-2-(2'-fluoro[1,1'-biphenyl]-4-yl)acetamide
425. N-(5-cyclopropyl-1H-pyrazol-3-yl)-2-(3'-fluoro[1,1'-biphenyl]-4-yl)acetamide
426. N-(5-cyclopropyl-1H-pyrazol-3-yl)-2-(3'-methoxy[1,1'-biphenyl]-4-yl)acetamide
427. N-(5-cyclopropyl-1H-pyrazol-3-yl)-2-(pentafluoro[1,1'-biphenyl]-4-yl)acetamide
428. N-(5-cyclopropyl-1H-pyrazol-3-yl)-2-(4'-(trifluoromethoxy)[1,1'-biphenyl]-4-yl)acetamide
429. N-(5-cyclopropyl-1H-pyrazol-3-yl)-2-(4'-carboxy[1,1'-biphenyl]-4-yl)acetamide
430. N-(5-cyclopropyl-1H-pyrazol-3-yl)-2-(3'-formyl-4'-methoxy[1,1'-biphenyl]-4-yl)acetamide
431. N-(5-cyclopropyl-1H-pyrazol-3-yl)-2-(4'-fluoro-3'-methyl[1,1'-biphenyl]-4-yl)acetamide
432. N-(5-cyclopropyl-1H-pyrazol-3-yl)-2-(2',5'-dichloro[1,1'-biphenyl]-4-yl)acetamide
433. N-(5-cyclopropyl-1H-pyrazol-3-yl)-2-(3'-acetyl[1,1'-biphenyl]-4-yl)acetamide
434. N-(5-cyclopropyl-1H-pyrazol-3-yl)-2-(4'-formyl[1,1'-biphenyl]-4-yl)acetamide
435. N-(5-cyclopropyl-1H-pyrazol-3-yl)-2-(2',5' difluoro[1,1'-biphenyl]-4-yl)acetamide
436. N-(5-cyclopropyl-1H-pyrazol-3-yl)-2-(2',5'-dimethyl[1,1'-biphenyl]-4-yl)acetamide
437. N-(5-cyclopropyl-1H-pyrazol-3-yl)-2-(2',6-difluoro[1,1'-biphenyl]-4-yl)acetamide
438. N-(5-cyclopropyl-1H-pyrazol-3-yl)-2-(4'-methoxy[1,1'-biphenyl]-4-yl)acetamide
439. N-(5-cyclopropyl-1H-pyrazol-3-yl)-2-(2',6-dimethyl[1,1'-biphenyl]-4-yl)acetamide
440. N-(5-cyclopropyl-1H-pyrazol-3-yl)-2-(5'-fluoro-2'-methoxy[1,1'-biphenyl]-4-yl)acetamide
441. N-(5-cyclopropyl-1H-pyrazol-3-yl)-2-(2',5'-dimethoxy[1,1'-biphenyl]-4-yl)acetamide
442. N-(5-cyclopropyl-1H-pyrazol-3-yl)-2-(2',6-dimethoxy[1,1'-biphenyl]-4-yl)acetamide
443. N-(5-cyclopropyl-1H-pyrazol-3-yl)-2-(4'-acetyl-[1,1'-biphenyl]-4-yl)acetamide
444. N-(5-cyclopropyl-1H-pyrazol-3-yl)-2-(4'-ethoxy-[1,1'-biphenyl]-4-yl)acetamide
445. N-(5-cyclopropyl-1H-pyrazol-3-yl)-2-((4'-methylthio)-[1,1'-biphenyl]-4-yl)acetamide
446. N-(5-cyclopropyl-1H-pyrazol-3-yl)-2-(3'-chloro-4'-fluoro-[1,1'-biphenyl]-4-yl)acetamide
447. N-(5-cyclopropyl-1H-pyrazol-3-yl)-2-(2'-acetyl-[1,1'-biphenyl]-4-yl)acetamide
448. N-(5-cyclopropyl-1H-pyrazol-3-yl)-2-(4'-ethyl-[1,1'-biphenyl]-4-yl)acetamide
449. N-(5-cyclopropyl-1H-pyrazol-3-yl)-2-(3'-ethoxy-[1,1'-biphenyl]-4-yl)acetamide
450. N-(5-cyclopropyl-1H-pyrazol-3-yl)-2-(3',4'-dimethoxy-[1,1'-biphenyl]-4-yl)acetamide
451. N-(5-cyclopropyl-1H-pyrazol-3-yl)-2-(2'-ethoxy-[1,1'-biphenyl]-4-yl)acetamide
452. N-(5-cyclopropyl-1H-pyrazol-3-yl)-2-(3',5'-difluoro-[1,1'-biphenyl]-4-yl)acetamide
453. N-(5-cyclopropyl-1H-pyrazol-3-yl)-2-(2',4'-dimethoxy-[1,1'-biphenyl]-4-yl)acetamide
454. N-(5-cyclopropyl-1H-pyrazol-3-yl)-2-(2',3'-dimethyl-[1,1'-biphenyl]-4-yl)acetamide
455. N-(5-cyclopropyl-1H-pyrazol-3-yl)-2-(3'-(trifluoromethoxy)[1,1'-biphenyl]-4-yl)acetamide
456. N-(5-cyclopropyl-1H-pyrazol-3-yl)-2-(3',4'-difluoro-[1,1'-biphenyl]-4-yl)acetamide
457. N-(5-cyclopropyl-1H-pyrazol-3-yl)-2-(4'-tert-butyl-[1,1'-biphenyl]-4-yl)acetamide
458. N-(5-cyclopropyl-1H-pyrazol-3-yl)-2-(3'-acetamido[1,1'-biphenyl]-4-yl)acetamide
459. N-(5-cyclopropyl-1H-pyrazol-3-yl)-2-(4'-trifluoromethyl-[1,1'-biphenyl]-4-yl)acetamide
460. N-(5-cyclopropyl-1H-pyrazol-3-yl)-2-(3'-(hydroxymethyl)[1,1'-biphenyl]-4-yl)acetamide
461. N-(5-cyclopropyl-1H-pyrazol-3-yl)-2-(3'-nitro[1,1'-biphenyl]-4-yl)acetamide
462. N-(5-cyclopropyl-1H-pyrazol-3-yl)-2-(4'-(hydroxymethyl)[1,1'-biphenyl]-4-yl)acetamide
463. N-(5-cyclopropyl-1H-pyrazol-3-yl)-2-(2'-chloro-[1,1'-biphenyl]-4-yl)acetamide
464. 2-[4-(1,3-benzodioxol-5-yl)phenyl-N-(5-cyclopropyl-1H-pyrazol-3-yl)acetamide;
465. N-(5-cyclopropyl-1H-pyrazol-3-yl)-2-[4-(1-naphthyl)phenyl]acetamide;
466. N-(5-cyclopropyl-1H-pyrazol-3-yl)-2-[4-(2-naphthyl)phenyl]acetamide;
467. N-(5-cyclopropyl-1H-pyrazol-3-yl)-2-[4-(2-furyl)phenyl]acetamide;
468. 2-[4-(5-acetyl-2-thienyl)phenyl]-N-(5-cyclopropyl-1H-pyrazol-3-yl)acetamide;
469. 2-[4-(5-chloro-2-thienyl)phenyl]-N-(5-cyclopropyl-1H-pyrazol-3-yl)acetamide;
470. N-(5-cyclopropyl-1H-pyrazol-3-yl)-2-[4-(5-methyl-2-thienyl)phenyl]acetamide;
471. 2-[4-(1-benzofuran-2-yl)phenyl]-N-(5-cyclopropyl-1H-pyrazol-3-yl)acetamide;
472. N-(5-cyclopropyl-1H-pyrazol-3-yl)-2-[4-(2-thienyl)phenyl]acetamide;
473. N-(5-cyclopropyl-1H-pyrazol-3-yl)-2-[3'-({[5-(dimethylamino)-1-naphthyl]sulfonyl}amino)[1,1'-biphenyl]-4-yl)acetamide;
474. 2-[4-(1-benzothien-2-yl)phenyl]-N-(5-cyclopropyl-1H-pyrazol-3-yl)acetamide;
475. N-(5-cyclopropyl-1H-pyrazol-3-yl)-2-[4-(3-formyl-2-thienyl)phenyl]acetamide;
476. N-(5-cyclopropyl-1H-pyrazol-3-yl)-2-[4-(3-formyl-2-thienyl)phenyl]acetamide;

477. 5-(4-{2-[(5-cyclopropyl-1H-pyrazol-3-yl)amino]-2-oxoethyl}phenyl)-2-furoic acid;
478. N-(5-cyclopropyl-1H-pyrazol-3-yl)-2-[4-(3-methyl-1H-pyrazol-4-yl)phenyl]acetamide;
479. N-(5-cyclopropyl-1H-pyrazol-3-yl)-2-[4-(3,5-dimethyl-1H-pyrazol-4-yl)phenyl]acetamide;
480. N-(5-cyclopropyl-1H-pyrazol-3-yl)-2-[4-(3-furyl)phenyl]acetamide;
481. N-(5-cyclopropyl-1H-pyrazol-3-yl)-2-[4-(5-formyl-3-thienyl)phenyl]acetamide;
482. [5-(4-{2-[(5-cyclopropyl-1H-pyrazol-3-yl)amino]-2-oxoethyl}phenyl)-1H-indol-3-yl]acetic acid;
483. 5-(4-{2-[(5-cyclopropyl-1H-pyrazol-3-yl)amino]-2-oxoethyl}phenyl)tryptophan;
484. N-(5-cyclopropyl-1H-pyrazol-3-yl)-2-[4-(2-pyridinyl)phenyl]acetamide;
485. 1-acetyl-5-(4-{2-[(5-cyclopropyl-1H-pyrazol-3-yl)amino]-2-oxoethyl}phenyl)-1H-indol-3-yl acetate;
486. 2-[4-(2-amino-4-hydroxy-6-methyl-5-pyrimidinyl)phenyl]-N-(5-cyclopropyl-1H-pyrazol-3-yl)acetamide;
487. N-(5-cyclopropyl-1H-pyrazol-3-yl)-2-[4-(5-pyrimidinyl)phenyl]acetamide;
488. N-(5-cyclopropyl-1H-pyrazol-3-yl)-2-[4-(2-pyridinyl)phenyl]acetamide;
489. N-(5-cyclopropyl-1H-pyrazol-3-yl)-2-[4-(5-nitro-2-pyridinyl)phenyl]acetamide;
490. N-(5-cyclopropyl-1H-pyrazol-3-yl)-2-[4-(6-amino-3-pyridinyl)phenyl]acetamide;
491. N-(5-cyclopropyl-1H-pyrazol-3-yl)-2-[4-(3-pyridinyl)phenyl]acetamide;
492. N-(5-cyclopropyl-1H-pyrazol-3-yl)-2-[4-(3-quinolinyl)phenyl]acetamide;
493. N-(5-cyclopropyl-1H-pyrazol-3-yl)-2-[4-(4-isoquinolinyl)phenyl]acetamide;
494. 5-(4-{2-[(5-cyclopropyl-1H-pyrazol-3-yl)amino]-2-oxoethyl}phenyl)nicotinic acid;
495. N-(5-cyclopropyl-1H-pyrazol-3-yl)-2-[4-(2-amino-5-pyrimidinyl)phenyl]acetamide;
496. N-(5-cyclopropyl-1H-pyrazol-3-yl)-2-[4-(4-pyridinyl)phenyl]acetamide;
497. N-(5-cyclopropyl-1H-pyrazol-3-yl)-2-[4-(5-acetyl-2-thienyl)phenyl]acetamide;
498. N-(5-cyclopropyl-1H-pyrazol-3-yl)-2-[4-(9H-purin-6-yl)phenyl]acetamide;
499. 2-[4-(1-benzothien-3-yl)phenyl]-N-(5-cyclopropyl-1H-pyrazol-3-yl)acetamide;
500. 5-(4-{2-[(5-cyclopropyl-1H-pyrazol-3-yl)amino]-2-oxoethyl}phenyl)-1H-indol-3-yl acetate;
501. N-(5-cyclopropyl-1H-pyrazol-3-yl)-2-[4-(2,4-dimethoxy-5-pyrimidinyl)phenyl]acetamide;
502. N-(5-cyclopropyl-1H-pyrazol-3-yl)-2-[4-(2-chloro-3-thienyl)phenyl]acetamide;
503. N-(5-cyclopropyl-1H-pyrazol-3-yl)-2-[4-(6-methyl-2-pyridinyl)phenyl]acetamide;
504. N-(5-cyclopropyl-1H-pyrazol-3-yl)-2-[4-(1H-imidazol-5-yl)phenyl]acetamide;
505. 2-[4-(6-amino-5-nitro-3-pyridinyl)phenyl]-N-(5-cyclopropyl-1H-pyrazol-3-yl)acetamide;
506. N-(5-cyclopropyl-1H-pyrazol-3-yl)-2-[4-(2,3,5,6-tetrafluoro-4-pyridinyl)phenyl]acetamide;
507. N-(5-cyclopropyl-1H-pyrazol-3-yl)-2-[4-(4-methyl-2-pyridinyl)phenyl]acetamide;
508. N-(5-cyclopropyl-1H-pyrazol-3-yl)-2-[4-(1H-pyrazol-4-yl)phenyl]acetamide;
509. 5-(4-{2-[(5-cyclopropyl-1H-pyrazol-3-yl)amino]-2-oxoethyl}phenyl)-2-thiophene acid;
510. N-(5-cyclopropyl-1H-pyrazol-3-yl)-2-[4-(6-methoxy-2-pyridinyl)phenyl]acetamide;
511. 6-(4-{2-[(5-cyclopropyl-1H-pyrazol-3-yl)amino]-2-oxoethyl}phenyl)-2-pyridinecarboxylic acid;
512. N-(5-cyclopropyl-1H-pyrazol-3-yl)-2-[4-(2,4-dichloro-5-pyrimidinyl)phenyl]acetamide;
513. N-(5-cyclopropyl-1H-pyrazol-3-yl)-2-[4-(4-methyl-3-thienyl)phenyl]acetamide;
514. N-(5-cyclopropyl-1H-pyrazol-3-yl)-2-[4-(5-formyl-2-furyl)phenyl]acetamide;
515. N-(5-cyclopropyl-1H-pyrazol-3-yl)-2-[4-(6-nitro-3-pyridinyl)phenyl]acetamide;
516. N-(5-cyclopropyl-1H-pyrazol-3-yl)-2-[4-(8-quinolinyl)phenyl]acetamide;
517. N-(5-cyclopropyl-1H-pyrazol-3-yl)-2-[4-(5-methyl-2-pyridinyl)phenyl]acetamide;
518. N-(5-cyclopropyl-1H-pyrazol-3-yl)-2-[4-(3-methyl-2-pyridinyl)phenyl]acetamide;
519. N-(5-cyclopropyl-1H-pyrazol-3-yl)-2-[4-(1H-indol-7-yl)phenyl]acetamide;
520. N-(5-cyclopropyl-1H-pyrazol-3-yl)-2-[4-(6-methoxy-3-pyridinyl)phenyl]acetamide;
521. N-(5-cyclopropyl-1H-pyrazol-3-yl)-2-[4-(2-amino-9H-purin-6-yl)phenyl]acetamide;
522. N-(5-cyclopropyl-1H-pyrazol-3-yl)-2-[4-(2-methyl-1H-indol-5-yl)phenyl]acetamide;
523. N-(5-cyclopropyl-1H-pyrazol-3-yl)-2-[4-(6-fluoro-3-pyridinyl)phenyl]acetamide.
524. N-(5-cyclopropyl-1H-pyrazol-3-yl)-2-[4'-(ethylsulfanyl)[1,1'-biphenyl]-4-yl]acetamide;
525. N-(5-cyclopropyl-1H-pyrazol-3-yl)-2-(3',4'-dimethyl[1,1'-biphenyl]-4-yl)acetamide;
526. N-(5-cyclopropyl-1H-pyrazol-3-yl)-2-(4'-hydroxy[1,1'-biphenyl]-4-yl)acetamide;
527. (2E)-3-(4'-{2-[(5-cyclopropyl-1H-pyrazol-3-yl)amino]-2-oxoethyl}[1,1'-biphenyl]-3-yl)-2-propenoic acid;
528. N-(5-cyclopropyl-1H-pyrazol-3-yl)-2-[3'-(trifluoromethyl)[1,1'-biphenyl]-4-yl]acetamide;
529. N-(5-cyclopropyl-1H-pyrazol-3-yl)-2-(4'-methyl[1,1'-biphenyl]-4-yl)acetamide;
530. N-(5-cyclopropyl-1H-pyrazol-3-yl)-2-[2'-(methylsulfanyl)[1,1'-biphenyl]-4-yl]acetamide;
531. 4'-{2-[(5-cyclopropyl-1H-pyrazol-3-yl)amino]-2-oxoethyl}[1,1'-biphenyl]-2-carboxylic acid;
532. 3-(4'-{2-[(5-cyclopropyl-1H-pyrazol-3-yl)amino]-2-oxoethyl}[1,1'-biphenyl]-4-yl)propanoic acid;
533. 2-[4'-(benzyloxy)[1,1'-biphenyl]-4-yl]-N-(5-cyclopropyl-1H-pyrazol-3-yl)acetamide;
534. N-(5-cyclopropyl-1H-pyrazol-3-yl)-2-(2',3'-dichloro[1,1'-biphenyl]-4-yl)acetamide;
535. N-(5-cyclopropyl-1H-pyrazol-3-yl)-2-(3'-isopropyl[1,1'-biphenyl]-4-yl)acetamide;
536. N-(5-cyclopropyl-1H-pyrazol-3-yl)-2-[4-(3-formyl-2-furyl)phenyl]acetamide;
537. (2E)-3-(4'-{2-[(5-cyclopropyl-1H-pyrazol-3-yl)amino]-2-oxoethyl}[1,1'-biphenyl]-4-yl)-2-propenoic acid;

538. N-(5-cyclopropyl-1H-pyrazol-3-yl)-2-{4'-[(E)-2-nitro-ethenyl][1,1'-biphenyl]-4-yl}acetamide;
539. 2-(4'-chloro[1,1'-biphenyl]-4-yl)-N-(5-cyclopropyl-1H-pyrazol-3-yl)acetamide;
540. N-(5-cyclopropyl-1H-pyrazol-3-yl)-2-(3'-methyl[1,1'-biphenyl]-4-yl)acetamide;
541. 2-(4'-phenyl[1,1'-biphenyl]-4-yl)-N-(5-cyclopropyl-1H-pyrazol-3-yl)acetamide;
542. N-(5-cyclopropyl-1H-pyrazol-3-yl)-2-(4'-phenoxy[1,1'-biphenyl]-4-yl)acetamide;
543. N-(5-cyclopropyl-1H-pyrazol-3-yl)-2-(2'-formyl[1,1'-biphenyl]-4-yl)acetamide;
544. 2-(3'-chloro-[1,1'-biphenyl]-4-yl)-N-(5-cyclopropyl-1H-pyrazol-3-yl)acetamide;
545. N-(5-cyclopropyl-1H-pyrazol-3-yl)-2-(3'-formyl[1,1'-biphenyl]-4-yl)acetamide;
546. tert-butyl 2-(4-{2-[(5-cyclopropyl-1H-pyrazol-3-yl)amino]-2-oxoethyl}phenyl)-1H-pyrrole-1-carboxylate;
547. 2-(3'-cyano[1,1'-biphenyl]-4-yl)-N-(5-cyclopropyl-1H-pyrazol-3-yl)acetamide;
548. N-(5-cyclopropyl-1H-pyrazol-3-yl)-2-(4-dibenzo[b,d]furan-4-ylphenyl)acetamide.

The compounds of formula (I), and the salts thereof, may be obtained, for example, by a process comprising:

(a) reacting a compound represented by formula (II):

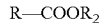   (II)

where R is as defined above and $R_2$ is an alkyl group, with acetonitrile in the presence of a basic agent, to obtain a compound represented by formula (III):

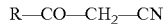   (III)

where R is as defined above;

(b) reacting a compound represented by formula (III) with hydrazine hydrate to obtain a compound represented by formula (IV):

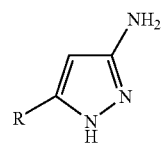   (IV)

where R is as defined above;

(c) oxidizing a compound represented by formula (IV) to obtain a compound represented by formula (V):

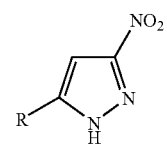   (V)

where R is as defined above;

(d) reacting a compound represented by formula (V) with tert-butoxycarbonyl anhydride ($Boc_2O$) to obtain a compound represented by formula (VI):

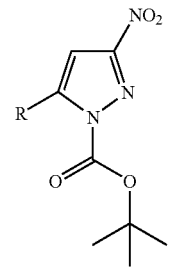   (VI)

where R is as defined above;

(e) reducing a compound represented by formula (VI) to obtain a compound represented by formula (VII):

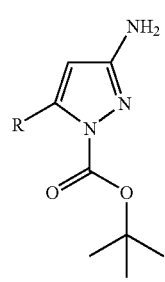   (VII)

where R is as defined above;

(f) reacting a compound represented by formula (VII) with a compound represented by formula (VIII):

   (VIII)

where X is hydroxy or a suitable leaving group and $R_1$ is as defined above, to obtain a compound represented by formula (IX):

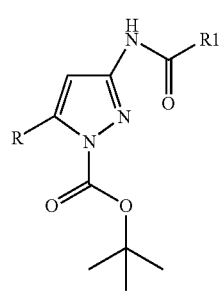   (IX)

where R and $R_1$ are as defined above; and (g) hydrolyzing a compound represented by formula (IX) in an acidic medium to obtain a compound of formula (I), where R and $R_1$ are as defined above;

and, if desired, converting a 3-amino-pyrazole derivative represented by formula (I) into another derivative represented by formula (I), and/or into a salt thereof.

Alternatively, the compounds represented by formula (I) and pharmaceutically acceptable salts thereof may be obtained by a process comprising:

(a) reacting a compound represented by formula (IV):

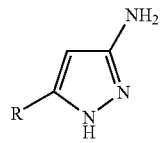
(IV)

with a compound represented by formula (VIII):

 (VIII)

where R and $R_1$ are as defined above and X is hydroxy or a suitable leaving group, preferably chlorine or bromine, to obtain a compound represented by formula (X):

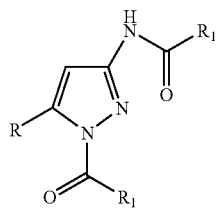
(X)

where R and $R_1$ are as defined above; and (b) selectively hydrolyzing a compound of formula (X) in a basic medium, to obtain a compound represented by formula (I).

Alternatively, the compounds represented by formula (I) and pharmaceutically acceptable salts thereof may be obtained by reacting a compound represented by formula (IV):

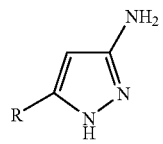
(IV)

with a compound represented by formula (XI):

 (XI)

where R and $R_1$ are as defined above.

Alternatively, the compound of formula (I) and pharmaceutically acceptable salts thereof may be obtained by reacting a compound of formula (I) wherein $R_1$ is a 4-halogeno-phenylacetyl group, or a polymer supported form of it (Ib)

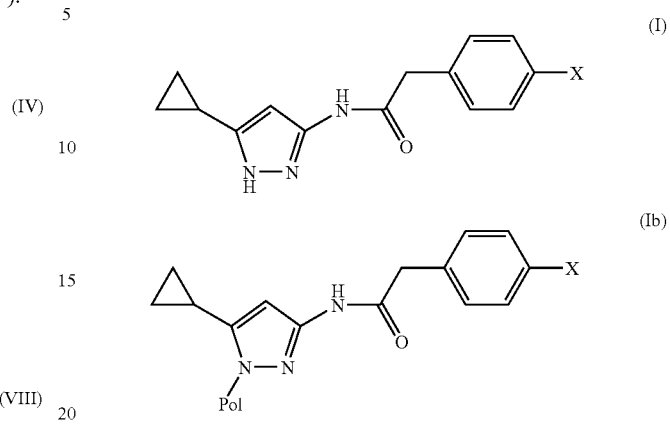

wherein X is a halogen atom such as bromine or iodine, with a compound of formula (XII)

(XII)

where $R_3$ is an aryl group, under well known Suzuki conditions, to obtain a compound of formula (I) wherein $R_3$ is aryl, or a polymer supported form of it (Ib)

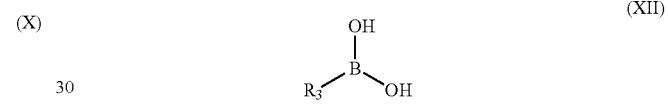

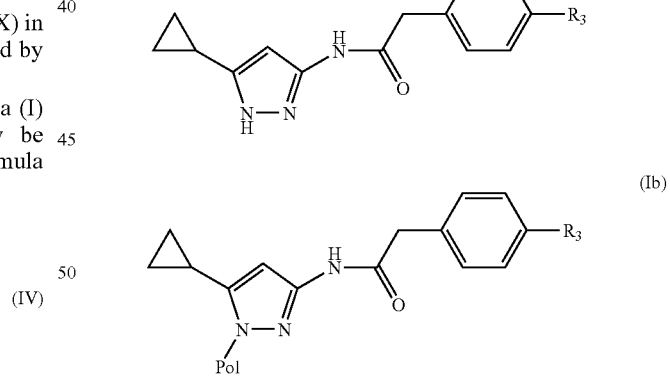

and, in the case of a polymer supported compound (Ib), hydrolizing it by acidic treatment to obtain the above compound of formula (I).

Alternatively, the compounds of formula (I) and pharmaceutically acceptable salts thereof may be obtained by a process comprising:

a) reacting a compound of formula (I) wherein $R_1$ is a 4-halgeno-phenylacetyl group, or a polymer supported form of it (Ib) with a pinacol ester of a diboron compound, under Miyaura's conditions, to obtain a compound of formula (XIII) or a polymer supported form of it (XIIIb)

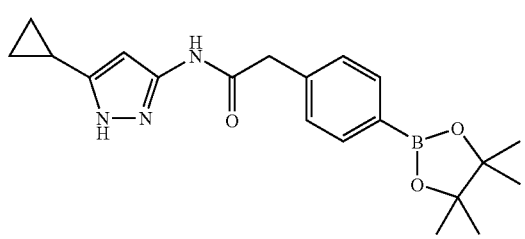

(XIII)

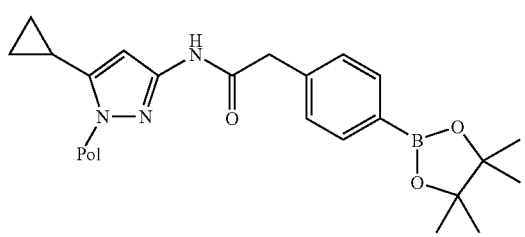

(XIIIb)

b) reacting a compound of formula (XIII) or a polymer supported form of it (XIIIb) with a compound of formula (XIV)

$R_3X$       (XIV)

where $R_3$ is aryl and X is bromine or iodine, to obtain a compound of formula (I) wherein $R_3$ is aryl or a polymer supported form of it (Ib)

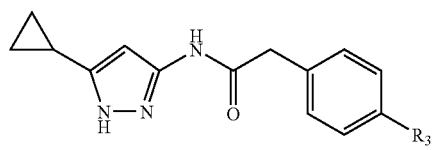

(I)

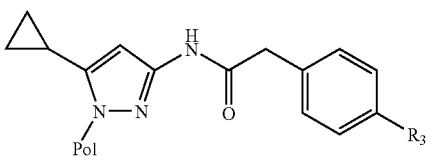

(Ib)

c) and, in the case of a polymer supported compound (Ib), hydrolizing it by acidic treatment to obtain the above compound of formula (I).

As will be readily appreciated, if the compounds of formula (I), prepared according to any one of the processes described above, are obtained as an admixture of isomers, their separation into the single isomers of formula (I), according to conventional techniques, is within the scope of the present invention.

Likewise, the conversion into the free compounds (I) of the corresponding salts thereof, according to well-known procedures, is still within the scope of the invention.

The reaction of a compound of formula (II) to produce a compound of formula (III) may be carried out with acetonitrile and a base such as sodium hydride in a suitable solvent such as diethylether, tetrahydrofuran, dioxane at a temperature ranging from room temperature to 120° C.

The reaction between a compound of formula (III) to produce a compound of formula (IV) is carried out with hydrazine hydrate, in a solvent such as methanol or ethanol at a temperature ranging from room temperature to 80° C.

The reaction of a compound of formula (IV) to produce a compound of formula (V) is carried out with OXONE® (potassium peroxymonosulfate) or another oxidizing agent such as hydrogen peroxide in a suitable solvent such as a mixture of water-acetone at a temperature ranging from 0° C. to room temperature.

The reaction of a compound of compound of formula (V) to produce a compound of formula (VI) is carried out with tert-butoxycarbonyl anhydride in a suitable solvent such as mixtures of methylene chloride-water at room temperature.

The reaction of a compound of formula (VI) to produce a compound of formula (VII) may be carried out directly with hydrogen in the presence of a catalyst such as palladium on charcoal, in a suitable solvent such as methanol or ethanol at room temperature.

The reaction between a compound of formula (VII) and a compound of formula (VIII) where X is a hydroxy group can be carried out in the presence of a coupling agent such as for instance, carbodiimide, i.e., 1,3-dicyclohexylcarbodiimide, 1,3-diisopropylcarbodiimide, or 1-(3-dimethylaminopropyl)-3-ethylcarbodiimide, in a suitable solvent such as, for example, dichloromethane, chloroform, tetrahydrofuran, diethyl ether, 1,4-dioxane, acetonitrile, toluene, or N,N-dimethylformamide at a temperature ranging from about −10 C. to reflux for a suitable time, i.e., from about 30 min. to about 96 hours. The reaction between a compound of formula (VII) and a compound of formula (VIII) may be also carried out by using a polymer supported coupling agent such as polystyrene supported dicyclohexylcarbodiimide in a suitable solvent such as methylene chloride, chloroform, dioxane, acetonitrile, N,N-dimethylformamide, tetrahydrofuran at room temperature for a time ranging from 12 to 96 hours.

The reaction between a compound of formula (VII) and a compound of formula (VIII) can be also carried out, for example, by a mixed anhydride method, using an alkyl chloroformate such as ethyl, iso-butyl, or iso-propyl chloroformate, in the presence of a tertiary base, such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

The reaction of a compound of formula (IX) to produce a compound of formula (I) can be carried out with an acid, such as trifluoroacetic acid, hydrochloric acid, formic acid, in a suitable solvent such as methylene chloride at a temperature ranging from 10° C. to room temperature.

The reaction between a compound of formula (IV) with a compound of formula (VIII) wherein X is a suitable leaving group can be carried out in the presence of a tertiary base, such as triethylamine, N-methylmorpholine, N,N-diisopropylethylamine or pyridine, in a suitable solvent such as toluene, dichloromethane, chloroform, diethylether, tetrahydrofuran, acetonitrile, dioxane or N,N-dimethylformamide, at a temperature ranging from about 10 C. to reflux. The reaction between a compound of formula (IV) and a compound of formula (VIII) can be also carried out the presence of a polymer supported tertiary base such as polystyrene supported N-methylmorpholine in a suitable solvent, for instance toluene, dichloromethane, chloroform, diethylether, tetrahydrofuran, acetonitrile, dioxane or N,N-dimethylformamide, at room temperature.

The reaction of a compound of formula (X) to produce a compound of formula (I) can be carried out with a base such as sodium hydroxide, potassium hydroxide, sodium carbonate or potassium carbonate in a suitable solvent such as mixture of methanol or ethanol and water at room temperature. The reaction of a compound of formula (X) to produce compound of formula (I) can be also carried out by using a polystyrene supported trisamine as a basic agent.

The reaction between a compound of formula (IV) with a compound of formula (XI) to obtain a compound of formula (I) can be carried out in the presence of a base such as triethylamine, N,N-diisopropylethylamine, N-methylmorpholine in a suitable solvent such as acetonitrile, dioxane, tetrahydrofurane, dimethylformamide at a temperature ranging from room temoerature to reflux.

The reaction between a compound of formula (I) wherein $R_1$ is 4-halogeno-phenylacetyl and a compound of formula (XII) to obtain a compound of formula (I) wherein $R_1$ is 4-aryl-phenylacetyl can be carried out in the presence of a base such as CsF, $Na_2CO_3$, $K_2CO_3$ and a catalyst such as $Pd(PPh_3)_4$, $PdCl_2(PPh_3)_2$, $Pd(OAc)_2/PPh_3$ in a suitable mixture of solvent such as dimethoxyethane and methanol, dioxane, tetrahydrofurane, dimethoxyethane, at a temperature ranging from room temperature to reflux.

The reaction between a compound of formula (I) wherein $R_1$ is 4-halogeno-phenylacetyl with a pinacol ester of a diboron compound to obtain a compound of formula (XIII) can be carried out in the presence of a base such as potassium acetate, triethylamine and a catalyst such as $PdCl_2$(diphenylphosphinoferrocene), $PdCl_2(PPh_3)_2$ in a suitable solvent such as dimethylformamide, dioxane, dimethylsolfoxide, dimethoxyethane, acetonitrile a temperature ranging from room temperature to reflux.

The reaction between a compound of formula (XIII) and a compound of formula (XIV) can be carried out in the presence of a suitable catalyst such as $Pd(PPh_3)_4$, $PdCl_2(PPh_3)_2$ and $K_3PO_4$, $K_2CO_3$, $Na_2CO_3$ in a suitable solvent such as dimethylformamide, dioxane, tetrahydrofurane, dimethoxyethane.

The compounds of formula (I) and the intermediates for preparing them as polymer supported forms, can be easily prepared according to conventional techniques known in the art; see, for example, *Tetrahedron Letters* 38 (15), 2629–2632 (1997).

Likewise, the conversion of these polymer supported forms into the free compounds is carried out according to conventional procedures by acid hydrolysis.

Also, the optional conversion of a compound of formula (I) into another compound of formula (I) can be carried according to known methods. The optional salification of a compound of formula (I) or the conversion of a salt into the free compound as well as the separation of a mixture of isomers into the single isomers may be carried out by conventional methods.

The compounds of formula (II), (VIII) wherein X is hydroxy or a leaving group as defined above, (XI), (XII) and (XIV) are known or can be obtained according to conventional techniques.

When preparing the compounds of formula (I), optional functional groups within both the starting materials or the intermediates thereof, which could give rise to unwanted side reactions, are preferably protected according conventional techniques. Likewise, the conversion of these protected compounds into the free deprotected compounds may be carried out according to well-known procedures.

Pharmacology

The compounds of formula (I) are active as cdk/cyclin inhibitors as they gave positive results when test according to the following procedure.

The inhibiting activity of putative cdk/cyclin inhibitors and the potency of selected compounds was determined through a method of assay based on the use of the Multi-Screen-PH 96 well plate (Millipore), in which phosphocellulose filter paper was placed at each well bottom allowing binding of positive charged substrate after a washing/filtration step.

When a radioactivity labelled phosphate moiety was transferred by the ser/threo kinase to the filter-bound histone, light emitted was measured in a scintillation counter.

The inhibition assay of cdk2/Cyclin A activity performed according to the following protocol:

Kinase reaction: 1.5·M histone H1 substrate, 25·M ATP (0.5 uCi P33g-ATP), 100 ng Cyclin A/cdk2 complex, 10·M inhibitor in a final volume of 100·1 buffer (TRIS HCl 10 mM pH 7.5, MgCl2 10 mM, 7.5 mM DTT) were added to each well of a 96 U bottom well plate. After 10 min at 37 C. incubation, reaction was stopped by 20·1 EDTA 120 mM.

Capture: 100·1 were transferred from each well Multi-Screen plate, to allow substrate binding phosphocellulose filter. Plates were then washed 3 times with 150·1/well PBS Ca++/Mg++ free and filtered by MultiScreen filtration system.

Detections: filters were allowed to dry at 37° C., then 100·1/well scintillant were added and 33P labelled histone H1 was detected by radioactivity counting in the Top-Count instrument.

Results: data were analyzed and expressed as % inhibition referred to total activity of enzyme (=100%).

All compounds showing inhibition >50% were further analyzed in order to study and define the kinetic-profile of the inhibitor via Ki calculation.

The protocol used was the same described above, except for ATP and substrate concentrations. Either the concentrate of ATP and histone H1 substrate were varied: 4, 8, 12, 24, 48·M for ATP (containing proportionally diluted P33g-ATP) and 0.4, 0.8, 1.2, 2.4, 4.8·M for histone were used in absence and presence of two different, properly chosen inhibitor concentrations.

Experimental data were analyzed by the computer program "SigmaPlot" for Ki determination, using a random bireactant system equation:

$$v = \frac{V_{max} \quad (A)(B)}{1 + (A) + (B) + (A)(B)} \\ \quad\quad aKAKB \\ \quad KA \quad KB \quad aKAKB$$

where A=ATP and B=histone H1.

In addition, the inhibiting activity of putative cdk/cyclin inhibitors and the potency of selected compounds was determined using a method of assay based on the use of a SPA (Scintillation Proximity Assay) 96 well plate assay. The assay is based on the ability of streptavidin-coated SPA beads to capture a biotinylated peptide derived from a phosphorylation site of histone.

When a radioactivity labelled phosphate moiety was transferred by the ser/threo kinase to the biotinylated histone peptide, light emitted was measured in scintillation counter.

The inhibition assay of cdk5/p25 activity was performed according to the following protocol; Kinase reaction: 1.0·M biotinylated histone peptide substrate, 0.25 uCi P33g-ATP, 4 nM cdk2/p25 complex, 0–100·M] inhibitor in a final volume of 100·1 buffer (Hepes 20 mM pH 7.5, MgCl2 15 mM, 1 mM DTT) were added to each well of a 96 U bottom well plate. After 20 min at 37 C. incubation, the reaction was stopped by the addition of 500 ug SPA beads in phosphate-buffered saline containing 0.1% Triton X-100 50 M ATP and 5 mM EDTA. The beads were allowed to settle, and the radioactivity incorporated in the 33P-labelled peptide was detected in a Top Count scintillation counter.

Results: Data were analyzed and expressed as % Inhibition using the formula:

$$100\times(1-(\text{Unknown}-\text{Bkgd})/(\text{Enz. Control}-\text{Bkgd}))$$

IC50 values were calculated using a variation of the four parameter logistics equation:

$$Y=100/[1+10^{\{(\text{LogEC50}-X)*\text{Slope}\}}]$$

Where X=log(uM) and Y=% Inhibition.

The compounds of formula (I) are therefore useful to restrict the unregulated proliferation of tumor cells, hence in therapy in the treatment of various tumors such as, for instance, carcinomas, e.g., mammary carcinoma, carcinoma, bladder carcinoma, colon carcinoma, ovary endometrial tumors, sarcomas, e.g., soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis a restenosis, and in the treatment of Alzheimer's disease.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

As an example, the compounds of the invention can be administered in combination with one or more chemotherapeutic agents such as, for instance, taxane, taxane derivatives, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, Sugen SU-5416, Sugen SU-6668, Herceptin, and the like, optionally within liposomal formulations thereof.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage, level depends upon the age, weight, conditions of patient and the administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following convention methods and are administered in a pharmaceutically suitable form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatin methylcellulose, carboxymethylcellulose or polyvinyl pyrrolidone; disintegrating agents, e.g., a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

The syrups may contain as carrier, for example, saccharose or saccharose with glycerine and/or mannitol and sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol, and, if desired, a suitable amount of lidocaine hydrochloride. The solutions for intravenous injections or infusions may contain as a carrier, for example, sterile water or preferably they may be in the form of sterile, aqueous isotonic saline solutions or they may contain as a carrier propylene glycol.

The suppositories may contain together with the active compound a pharmaceutically acceptable carrier, e.g., cocoa butter, polyethylene glycol, a polyoxyethylene sorbitan fatty acid ester surfactant or lecithin.

EXAMPLES

Having generally described this invention, a further understanding can be obtained by reference to certain specific examples which are provided herein for purposes of illustration only and are not intended to be limiting unless otherwise specified.

Example 1

N-(5-cyproyl-1H-pyrazol-3-yl)-2,2-diphenyl Acetamide

To a solution of 45.6 mg (0.215 mmol) of diphenylacetic acid in 3 ml of dichloromethane at 0° C. 41.2 mg (0.215 mmol) of N-(3-dimethylaminopropyl)-N'-ethylcarbodiimide hydrochloride were added. After 1 hour at the same temperature under stirring 40 mg (0.179 mmol) of tert-butyl-3-amino-5-cyclopropyl-1H-pyrazole-1-carboxylate were added. The mixture was maintained at room temperature for 16 hours, then was diluted with dichloromethane and washed with a saturated solution of sodium hydrogenocarbonate. The organic layer was dried over anhydrous sodium sulfate evaporated to dryness, to give, after column chromatography (hexane-ethylacetate) 60 mg (80% yield) of N-(5-cyclopropyl-1-terbutoxycarbonyl-pyrazol-3-yl)-2,2-diphenyl acetamide. This intermediate was submitted to hydrolysis with 15 ml of trifluoroacetic acid 10% v/v in dichloromethane for an hour. The solvent was then evaporated under vacuum, the residue redissolved with dichloromethane and washed with a saturated solution sodium hydrogen carbonate. The organic layer was dried over anhydrous sodium sulfate and evaporated to give 42 mg (92% yield) of the title compound.

1H-NMR (400 MHz, DMSO-d6) ppm: 0.62 (m, 2H, cyclopropyl CHH+CHH); 0.88 (m, 2H, cyclopropyl CHH+CHH); 1.81 (dddd, 1H, J=5.2, 5.2, 8.4, 8.4, cyclopropyl CH); 5.17 (s, 1H, CHPh2); 6.17 (s, 1H, pyrazole CH); 7.30 (m, 10H, phenyl CH); 10.6 (s, 1H, amidic NH); 12.04 (s, 1H, pyrazole NH).

ESI (+) MS: m/z 318 (100, MH+).

m.p. 218–220° C.

Analogously the following products were prepared starting from the corresponding carboxylic acid:

N-(5-cyclopropyl-1H-pyrazol-3-yl)-2-methyl-5-phenyl-3-furamide;

1H-NMR (400 MHz, DMSO-d6) ppm 7.6–7.3 (m, 5H, Ph), 6.24 (s, 1H, CH-pyrazole), 2.6 (s, 3H, CH3); 1.83 (m, 1H, cyclopropyl-CH);

ESI (+) MS: m/z 308 (100, MH+).

N-(5-cyclopropyl-1H-pyrazol-3-yl)-2,5-dimethyl-1-(2-thienylmethyl)-1H-pyrrole-3-carboxamide;

1H-NMR (400 MHz, DMSO-d6) ppm 7.41 (dd, J=5—1.2 Hz, 5H, SCH), 6.48 (s, 1H, CH-pyrrole), 6.09 (s, 1H, CH-pyrazole); 1.83 (m, 1H, cyclopropyl-CH);

ESI (+) MS: m/z 341 (100, MH+);

N-(5-cyclopropyl-1H-pyrazol-3-yl)-5-(methylsulfonyl)-2-thiophenecarboxamide;

1H-NMR (400 MHz, DMSO-d6) ppm 7.41 (dd, J=5–1.2 Hz, 5H, SCH), 6.48 (s, 1H, CH-pyrrole), 6.09 (s, 1H, CH-pyrazole); 1.83 (m, 1H, cyclopropyl-CH);

ESI (+) MS: m/z 312 (100, MH+);

N-(5-cyclopropyl-1H-pyrazol-3-yl)-2-oxo-4-phenyl-3-butenamide;

1H-NMR (400 MHz, DMSO-d6) ppm 7.8 (m, 3H, CH-o-Ph+CH-4), 6.48 (s, 4H, CH-m,p-Ph+CH-3), 6.25 (s, 1H, CH-pyrazole); 1.85 (m, 1H, cyclopropyl-CH);

ESI (+) MS: m/z 282 (100, MH+);

2-amino-N-(4-{2-[(N-(5-cyclopropyl-1H-pyrazol-3-yl)-amino]-2-oxoethyl}phenyl)acetamide;

1H-NMR (400 MHz, DMSO-d6) ppm 10.36 (s, 1H, NHCO), 7.20 (d, J=8.5 Hz, 2H, CH-o-Ph), 6.09 (s, 1H, CH-pyrazole); 3.49 (s, 2H, COCH2NH2), 1.81 (m, 1H, cyclopropyl-CH);

ESI (+) MS: m/z 314 (100, MH+);

2-[4-(aminomethyl)phenyl]-N-(3-cyclopropyl-1H-pyrazol-5-yl)acetamide;

1H-NMR (400 MHz, DMSO-d6) ppm 10.36 (s, 1H, NHCO), 7.47 (d, J=8.5 Hz, 4H, Ph), 6.08 (s, 1H, CH-pyrazole); 3.48 (s, 2H, COCH2), 1.81 (m, 1H, cyclopropyl-CH);

ESI (+) MS: m/z 271 (100, MH+);

N-(3-cyclopropyl-1H-pyrazol-5-yl)-2-[4-(2-oxo-1-pyrrolidinyl)phenyl]acetamide;

1H-NMR (400 MHz, DMSO-d6) ppm 10.37 (s, 1H, NHCO), 7.55 (dd, J=9.2–2.5 Hz, 2H, m-Ph), 6.09 (s, 1H, CH-pyrazole), 3.52 (s, 2H, COCH2), 1.81 (m, 1H, cyclopropyl-CH);

ESI (+) MS: m/z 325 (100, MH+);

4-{2-[(5-cyclopropyl-1H-pyrazol-3-yl)amino]-2-oxoethyl}benzamide;

1H-NMR (400 MHz, DMSO-d6) ppm 10.45 (s, 1H, NHCO), 7.77 (dd, J=6.5–1.8 Hz, 2H, m-Ph), 6.09 (s, 1H, CH-pyrazole); 3.61 (s, 2H, COCH2), 1.81 (m, 1H, cyclopropyl-CH);

ESI (+) MS: m/z 285 (100, MH+);

2-[4-(acetylamino)phenyl]-N-(5-cyclopropyl-1H-pyrazol-3-yl)acetamide;

1H-NMR (400 MHz, DMSO-d6) ppm 7.46 (d, J=8.5 Hz, 2H, m-Ph), 6.09 (s, 1H, CH-pyrazole); 3.48 (s, 2H, COCH2), 1.81 (m, 1H, cyclopropyl-CH);

ESI (+) MS: m/z 299 (100, MH+);

N-{2-[(5-cyclopropyl-1H-pyrazol-3-yl)amino]-2-oxoethyl}benzamide;

1H-NMR (400 MHz, DMSO-d6) ppm 7.9–7.4 (m, 5H, Ph), 6.12 (s, 1H, CH-pyrazole); 3.99 (d, J=6 Hz, 2H, COCH2), 1.80 (m, 1H, cyclopropyl-CH);

ESI (+) MS: m/z 285 (100, MH+);

N-(5-cyclopropyl-1H-pyrazol-3-yl)-2-(2-naphthyl)acetamide;

1H-NMR (400 MHz, DMSO-d6) ppm 6.10 (s, 1H, CH-pyrazole); 3.75 (s, 2H, COCH2), 1.80 (m, 1H, cyclopropyl-CH);

ESI (+) MS: m/z 292 (100, MH+);

5-chloro-N-(5-cyclopropyl-1H-pyrazol-3-yl)-2-thiophenecarboxamide;

1H-NMR (400 MHz, DMSO-d6) ppm 7.91 (d, J=4 Hz, 1H, CHCCl), 6.20 (s, 1H, CH-pyrazole), 1.85 (m, 1H, cyclopropyl-CH);

ESI (+) MS: m/z 268 (100, MH+);

N-(5-cyclopropyl-1H-pyrazol-3-yl)-2-[4-(1-pyrrolidinyl)phenyl]acetamide;

1H-NMR (400 MHz, DMSO-d6) ppm 6.44 (d, J=6.5 Hz, 2H, CH-m-Ph), 6.07 (s, 1H, CH-pyrazole); 3.37 (s, 2H, COCH2), 1.81 (m, 1H, cyclopropyl-CH);

ESI (+) MS: m/z 311 (100, MH+);

(2S)-N-(5-cyclopropyl-1H-pyrazol-3-yl)-2-(6-methoxy-2-naphthyl)propanamide

1H-NMR (400 MHz, DMSO-d6) ppm 6.11 (s, 1H, CH-pyrazole); 3.89 (q, J=6 Hz, 1H, COCH), 3.83 (s, 3H, OCH3), 1.81 (m, 1H, cyclopropyl-CH);
ESI (+) MS: m/z 336 (100, MH+);

N-(3-cyclopropyl-1H-pyrazol-5-yl)-2-(3-methoxyphenyl)acetamide m.p. 118–120° C.;

N-(3-cyclopropyl-1H-pyrazol-5-yl)-2-(4-nitrophenyl)acetamide m.p. 183–185° C.;

2-[5-(benzyloxy)-1H-indol-3-yl]-N-(5-cyclopropyl-1H-pyrazol-3-yl)acetamide;

N-(5-cyclopropyl-1H-pyrazol-3-yl)-2-(5-methoxy-2-methyl-1H-indol-3-yl)acetamide;

N-(5-cyclopropyl-1H-pyrazol-3-yl)-2-(5-hydroxy-1H-indole-3-yl)acetamide;

2-[1-(4-chlorobenzoyl)-5-methoxy-2-methyl-1H-indol-3-yl]-N-(5-cyclopropyl-1H-pyrazol-3-yl)acetamide;

N-(5-cyclopropyl-1H-pyrazol-3-yl)-2-(3-hydroxyphenyl)acetamide;

N-(5-cyclopropyl-1H-pyrazol-3-yl)-2-(4-hydroxy-3-methoxyphenyl)acetamide;

N-(5-cyclopropyl-1H-pyrazol-3-yl)-2-hydroxy-2-(4-hydroxy-3-methoxyphenyl)acetamide;

N-(5-cyclopropyl-1H-pyrazol-3-yl)-2-(4-bromomethylphenyl)acetamide;

N-(5-cyclopropyl-1H-pyrazol-3-yl)-2-[2-(formylamino)-1,3-thiazol-4-yl]-2-(methoxyimino)ethanamide;

2-[5-(chloroacetyl)-2-thienyl]-N-(5-cyclopropyl-1H-pyrazol-3-yl)acetamide;

N-(5-cyclopropyl-1H-pyrazol-3-yl)-2-(2-methyl-1H-indol-3-yl)acetamide;

2-chloro-N-(5-{2-[(5-cyclopropyl-1H-pyrazol-3-yl)amino]-2-oxoethyl}-1,3-thiazol-2-yl)acetamide;

N-(5-cyclopropyl-1H-pyrazol-3-yl)-2-(2-hydroxy-2-diphenyl)acetamide;

N-(5-cyclopropyl-1H-pyrazol-3-yl)-2-(2,6-dihydroxy-4-pyrimidinyl)acetamide;

N-(5-cyclopropyl-1H-pyrazol-3-yl)-2-(3-chloro-4-hydroxyphenyl)acetamide;

N-(5-cyclopropyl-1H-pyrazol-3-yl)-2-(7-methoxy-2-oxo-2H-chromen-4-yl)acetamide;

N-(5-cyclopropyl-1H-pyrazol-3-yl)-2-(2-acetylamino-2-phenyl)acetamide;

N-(5-cyclopropyl-1H-pyrazol-3-yl)-2-(1-methylimidazol-4-yl)acetamide;

N-(5-cyclopropyl-1H-pyrazol-3-yl)-2-(2-bromo-2-phenyl)acetamide;

N-(5-cyclopropyl-1H-pyrazol-3-yl)-2-(4-benzyloxy-3-methoxyphenyl)acetamide;

(2S)-N-(5-cyclopropyl-1H-pyrazol-3-yl)-2-hydroxy-2-phenylethanamide;

1-(4-chlorophenyl)-N-(5-cyclopropyl-1H-pyrazol-3-yl)cyclopentanecarboxamide;

N-(5-cyclopropyl-1H-pyrazol-3-yl)-2-(1H-indol-3-yl)-2-oxoacetamide;

N-(5-cyclopropyl-1H-pyrazol-3-yl)-2-(3,4-dihydroxyphenyl)acetamide;

N-(5-cyclopropyl-1H-pyrazol-3-yl)-2-benzyloxycarbonyl-2-phenylacetamide;

N-(5-cyclopropyl-1H-pyrazol-3-yl)-2-(3-methyl-1-benzothien-2-yl)acetamide;

N-(5-cyclopropyl-1H-pyrazol-3-yl)-2-(2-thienyl)acetamide;

5-cyclohexyl-1-(4-{2-[(5-cyclopropyl-1H-pyrazol-3-yl)amino]-2-oxoethyl}benzyl)2-aminopentanedioate;

N-(5-cyclopropyl-1H-pyrazol-3-yl)-2-(4-isobutylphenyl)propanamide;

N-(5-cyclopropyl-1H-pyrazol-3-yl)-2-(7-hydroxy-2-oxo-2H-chromen-4-yl)acetamide;

N-(5-cyclopropyl-1H-pyrazol-3-yl)-2-(4-hydroxyphenyl)acetamide;

2-cyclopentyl-N-(5-cyclopropyl-1H-pyrazol-3-yl)-2-phenylacetamide;

N-(5-cyclopropyl-1H-pyrazol-3-yl)-2-(2-furyl)-2-oxoacetamide;

N-(5-cyclopropyl-1H-pyrazol-3-yl)-2-(5-bromo-1H-indol-3-yl)acetamide;

N-(5-cyclopropyl-1H-pyrazol-3-yl)-2-(2,5-dioxo-2,5-dihydro-3-furanyl)acetamide;

2-chloro-2,2-bis(2-chlorophenyl)-N-(5-cyclopropyl-1H-pyrazol-3-yl)acetamide;

N-(5-cyclopropyl-1H-pyrazol-3-yl)-2-hydroxy-2-(3-hydroxy-4-methoxyphenyl)acetamide;

2-(5-bromo-3-pyridinyl)-N-(5-cyclopropyl-1H-pyrazol-3-yl)acetamide;

N-(5-cyclopropyl-1H-pyrazol-3-yl)-2-oxo-2H-pyran-5-carboxamide;

N-(5-cyclopropyl-1H-pyrazol-3-yl)-2-(2,4-dinitrophenyl)acetamide;

N-(5-cyclopropyl-1H-pyrazol-3-yl)-2-(3-bromo-4-methoxyphenyl)acetamide;

N-(5-cyclopropyl-1H-pyrazol-3-yl)-3-hydroxy-2-phenylpropanamide;

N-(5-cyclopropyl-1H-pyrazol-3-yl)-2-(3-fluoro-4-hydroxyphenyl)acetamide;

2-{2-[(chloroacetyl)amino]-1,3-thiazol-5-yl}-N-(5-cyclopropyl-1H-pyrazol-3-yl)-2-(methoxyimino)ethanamide;

N-(5-cyclopropyl-1H-pyrazol-3-yl)-1-phenylcyclopropanecarboxamide;

N-(5-cyclopropyl-1H-pyrazol-3-yl)-2-(2,5-dihydroxyphenyl)acetamide;

N-(5-cyclopropyl-1H-pyrazol-3-yl)-2-[2-(2,4-difluorophenyl)-1,3-thiazol-4-yl]acetamide;

N-(5-cyclopropyl-1H-pyrazol-3-yl)-2-(5-methoxy-3-hydroxy-2-propylphenyl)acetamide;

(2R)-N-(3-cyclopropyl-1H-pyrazol-5-yl)-2-(2-fluoro[1,1'-biphenyl]-4-yl)propanamide;

2-{4-[(aminocarbonyl)amino]phenyl}-N-(5-cyclopropyl-1H-pyrazol-3-yl)acetamide;

2-{4-[(2-amino-2-oxoethyl)amino]phenyl}-N-(5-cyclopropyl-1H-pyrazol-3-yl)acetamide;

N-(5-cyclopropyl-1H-pyrazol-3-yl)-2-(5-methyl-2-phenyl-1,3-thiazol-4-yl)acetamide;

4-bromo-N-(4-{2-[(5-cyclopropyl-1H-pyrazol-3-yl)amino]-2-oxoethyl}-1,3-thiazol-2-yl)benzamide;

2-[2-(4-chlorophenyl)-4-hydroxy-1,3-thiazol-5-yl]-N-(5-cyclopropyl-1H-pyrazol-3-yl)acetamide;

N-(4-{2-[(5-cyclopropyl-1H-pyrazol-3-yl)amino]-2-oxoethyl}-1,3-thiazol-2-yl)-2-(2-pyridinylsulfanyl)acetamide;

N-(4-{2-[(5-cyclopropyl-1H-pyrazol-3-yl)amino]-2-oxoethyl}-1,3-thiazol-2-yl)-2-(isopropylsulfanyl)acetamide;

2-(5-{[(4-chlorophenyl)sulfanyl]acetyl}-2-thienyl)-N-(5-cyclopropyl-1H-pyrazol-3-yl)acetamide;

2-(5-chloro-3-methyl-1-benzothien-2-yl)-N-(5-cyclopropyl-1H-pyrazol-3-yl)acetamide;

N-(5-cyclopropyl-1H-pyrazol-3-yl)-2-(2-iodophenyl)acetamide;

N-(5-cyclopropyl-1H-pyrazol-3-yl)-9H-xanthene-9-carboxamide;

N-(5-cyclopropyl-1H-pyrazol-3-yl)-2-(2-phenyl-1,3-thiazol-4-yl)acetamide;

2-[2-(4-chlorophenyl)-5-methyl-1,3-thiazol-4-yl]-N-(5-cyclopropyl-1H-pyrazol-3-yl)acetamide;

N-(4-{2-[(5-cyclopropyl-1H-pyrazol-3-yl)amino]-2-oxoethyl}-1,3-thiazol-2-yl)benzamide;

N-(5-cyclopropyl-1H-pyrazol-3-yl)-2-(6-methoxy-2-naphthyl)acrylamide;

N-(5-cyclopropyl-1H-pyrazol-3-yl)-2-(2-hydroxyphenyl)acetamide;

N-(5-cyclopropyl-1H-pyrazol-3-yl)-2,3-di(2-thienyl)-2-propenamide;

N-(5-cyclopropyl-1H-pyrazol-3-yl)-2-[2-(2-pyrazinyl)-1,3-thiazol-4-yl]acetamide;

N-(5-cyclopropyl-1H-pyrazol-3-yl)-2-(2,5-dibromo-3-thienyl)acetamide;

N-(5-cyclopropyl-1H-pyrazol-3-yl)-2-(4-methylsulfonylaminophenyl)acetamide;

N-(5-cyclopropyl-1H-pyrazol-3-yl)-2-{4-[2-(4-methyl-1-piperazinyl)ethoxy]phenyl}acetamide;

N-(5-cyclopropyl-1H-pyrazol-3-yl)-2-{4-[2-(1-pyrrolidinyl)ethoxy]phenyl}acetamide;

N-(5-cyclopropyl-1H-pyrazol-3-yl)-2-{4-(2-amino-2-oxoethoxy)phenyl}acetamide;

N-(5-cyclopropyl-1H-pyrazol-3-yl)-2-phenoxy-2-methylpropanamide;

N-(5-cyclopropyl-1H-pyrazol-3-yl)-2-(4-chlorophenoxy)propanamide;

N-(5-cyclopropyl-1H-pyrazol-3-yl)-2-(2-nitrophenoxy)acetamide;

N-(5-cyclopropyl-1H-pyrazol-3-yl)-2-(5-isopropyl-2-methyl-1H-indol-3-yl)acetamide;

N-(5-cyclopropyl-1H-pyrazol-3-yl)-2-(3-methoxyphenyl)acetamide;

N-(5-cyclopropyl-1H-pyrazol-3-yl)-2-methyl-2-(methyl-2,3-dihydro-1-benzofuran-5-yl)propanamide;

N-(5-cyclopropyl-1H-pyrazol-3-yl)-2-[2-(4-methoxyphenyl)-4-oxo-4H-chromen-6-yl]acetamide;

N-(5-cyclopropyl-1H-pyrazol-3-yl)-2-(6-chloro-2,3-dihydro-1H-inden-3-yl)butanamide;

N-(5-cyclopropyl-1H-pyrazol-3-yl)-2-[4-(1-oxo-1,3-dihydro-2H-isoindol-2-yl)phenyl]hexanamide;

N-(5-cyclopropyl-1H-pyrazol-3-yl)-2-phenyl-3-(4-pyridinyl)propenamide;

2-[1,1'-biphenyl]-4-yl-N-(5-cyclopropyl-1H-pyrazol-3-yl)butanamide;

N-(5-cyclopropyl-1H-pyrazol-3-yl)-2-[4-(1,3-dihydro-2H-isoindol-2-yl)phenyl]propanamide;

N-(5-cyclopropyl-1H-pyrazol-3-yl)-2-[4-(1-oxo-1,3-dihydro-2H-isoindol-2-yl)phenyl]butanamide;

N-(5-cyclopropyl-1H-pyrazol-3-yl)-(2S)-2-[4-(1-oxo-1,3-dihydro-2H-isoindol-2-yl)phenyl]propanamide;

N-(5-cyclopropyl-1H-pyrazol-3-yl)-2-[4-(5-amino-4-phenyl-1H-1,2,3-triazol-1-yl)phenyl]acetamide;

N-(5-cyclopropyl-1H-pyrazol-3-yl)-2-[4-(1-oxo-1,3-dihydro-2H-isoindol-2-yl)phenyl]pentanamide;

N-(5-cyclopropyl-1H-pyrazol-3-yl)-2-(4-benzyloxyphenyl)acetamide;

N-(5-cyclopropyl-1H-pyrazol-3-yl)-2-{4-[(3,3-diethyl-4-oxo-2-azetidinyl)oxy]phenyl}acetamide;

N-(5-cyclopropyl-1H-pyrazol-3-yl)-2-(5,6-dimethyl-1H-benzimidazol-1-yl)acetamide;

N-(5-cyclopropyl-1H-pyrazol-3-yl)-2-(4-pyridylsulfanyl)acetamide;

N-(5-cyclopropyl-1H-pyrazol-3-yl)-2-(1H-tetrazol-1-yl)acetamide;

N-(5-cyclopropyl-1H-pyrazol-3-yl)-2-(tetrazolo[1,5-b]pyridazin-6ylsulfanyl)acetamide;

2-[1,1'-biphenyl]-4-yl-N-(5-cyclopropyl-1H-pyrazol-3-yl)-2-hydroxyacetamide;

N-(5-cyclopropyl-1H-pyrazol-3-yl)-2-cyclohexene-1-carboxamide;

N-(5-cyclopropyl-1H-pyrazol-3-yl)-2-oxo-2H-pyran-4-carboxamide;

N-(5-cyclopropyl-1H-pyrazol-3-yl)-3-bromo-2,2-diphenylpropanamide;

N-(5-cyclopropyl-1H-pyrazol-3-yl)-4,4-bis(4-methylphenyl)-3-butenamide;

N-(5-cyclopropyl-1H-pyrazol-3-yl)-2-(4-hydroxy-5-isopropyl-2-methylphenyl)acetamide;

N-(5-cyclopropyl-1H-pyrazol-3-yl)-2-(4-nitrophenyl)-2-butenamide;

N-(5-cyclopropyl-1H-pyrazol-3-yl)-2-(3,4-dihydro-1-naphthyl)butanamide;

N-(3-cyclopropyl-1H-pyrazol-5-yl)-1,4-benzodioxine-2-carboxamide;

N-(3-cyclopropyl-1H-pyrazol-5-yl)-3-phenyl-1,4-benzodioxine-2-carboxamide;

N-(3-cyclopropyl-1H-pyrazol-5-yl)-4-oxo-4H-chromene-2-carboxamide;

N-(3-cyclopropyl-1H-pyrazol-5-yl)-2-oxo-1,2-dihydro-4-quinolinecarboxamide;

2-anilino-N-(3-cyclopropyl-1H-pyrazol-5-yl)acetamide;

Example 2

2-(1,3-benzodioxol-5-yl)-N-(3-cyclopropyl-1H-pyrazol-5-yl)-acetamide

To a solution of 96.8 mg (0.537 mmol) of 2-(1,3-benzodioxol-5-yl)-acetic acid in 3 ml of dichloromethane 360 mg (0.720 mmol) of polystyrene supported dicyclohexylcarbodiimide (loading=2 mmol/g) and 40 mg (0.179 mmol) of tert-butyl-3-amino-5-cyclopropyl-1H-pyrazole-1-carboxylate were added. The mixture was maintained under stirring at room temperature for 96 hours and after that time filtered, washed several times with dichloromethane and evaporated to dryness. The residue was re-dissolved with 3 ml of trifluoroacetic acid 10% V/V in dichloromethane and maintained at room temperature for an hour. The solvent was then evaporated, the residue re-dissolved in dichloromethane and washed with a saturated solution of sodium hydrogenocarbonate. The organic layer was evaporated to dryness to give, after trituration with diethylether, 32 mg (63% yield) of the title compound.

ESI (+) MS: m/z 286 (100, MH+).

m.p. 174–176° C.

Analogously, the following products were prepared:

N-(5-cyclopropyl-1H-pyrazol-3-yl)-2-(3,5-difluorophenyl)acetamide

1H-NMR (400 MHz, DMSO-d6) ppm 10.48 (s, 1H, NHCO), 7.1–6.9 (m, 3H, Ph), 6.09 (s, 1H, CH-pyrazole), 3.61 (s, 2H, COCH2), 1.82 (m, 1H, cyclopropyl-CH);

ESI (+) MS: m/z 278 (100, MH+);

N-(5-cyclopropyl-1H-pyrazol-3-yl)-2-(2,4-difluorophenyl)acetamide;

1H-NMR (400 MHz, DMSO-d6) ppm 10.46 (s, 1H, NHCO), 7.4–7.0 (m, 3H, Ph), 6.07 (s, 1H, CH-pyrazole), 3.62 (s, 2H, COCH2), 1.81 (m, 1H, cyclopropyl-CH);

ESI (+) MS: m/z 278 (100, MH+);

N-(5-cyclopropyl-1H-pyrazol-3-yl)-2-(2-chloro-6-fluorophenyl)acetamide;

1H-NMR (400 MHz, DMSO-d6) ppm 10.55 (s, 1H, NHCO), 7.3–7.1 (m, 3H, Ph), 6.05 (s, 1H, CH-pyrazole), 3.80 (s, 2H, COCH2), 1.82 (m, 1H, cyclopropyl-CH);

ESI (+) MS: m/z 294 (100, MH+);

N-(5-cyclopropyl-1H-pyrazol-3-yl)-2-(4-methylsulphonylphenyl)acetamide;

1H-NMR (400 MHz, DMSO-d6) ppm 10.54 (s, 1H, NHCO), 7.54 (dd, J=6.5–2 Hz, 2H, CH-o-Ph), 6.08 (s, 1H, CH-pyrazole), 3.70 (s, 2H, COCH2), 1.81 (m, 1H, cyclopropyl-CH);

ESI (+) MS: m/z 320 (100, MH+);

N-(5-cyclopropyl-1H-pyrazol-3-yl)-2-[3,5-bis(trifluoromethyl)phenyl]acetamide;

1H-NMR (400 MHz, DMSO-d6) ppm 10.56 (s, 1H, NHCO), 6.08 (s, 1H, CH-pyrazole), 3.83 (s, 2H, COCH2), 1.81 (m, 1H, cyclopropyl-CH);

ESI (+) MS: m/z 378 (100, MH+);

N-(5-cyclopropyl-1H-pyrazol-3-yl)-2-(2,5-difluorophenyl)acetamide;

1H-NMR (400 MHz, DMSO-d6) ppm 10.48 (s, 1H, NHCO), 7.2–7.0 (m, 3H, Ph), 6.08 (s, 1H, CH-pyrazole), 3.65 (s, 2H, COCH2), 1.81 (m, 1H, cyclopropyl-CH);

ESI (+) MS: m/z 278 (100, MH+);

N-(5-cyclopropyl-1H-pyrazol-3-yl)-2-(2-nitro-4-trifluoromethylphenyl)acetamide;

1H-NMR (400 MHz, DMSO-d6) ppm 10.56 (s, 1H, NHCO), 7.78 (d, J=8 Hz, 1H, CH-o-Ph), 6.01 (s, 1H, CH-pyrazole), 4.14 (s, 2H, COCH2), 1.81 (m, 1H, cyclopropyl-CH);

ESI (+) MS: m/z 355 (100, MH+);

N-(5-cyclopropyl-1H-pyrazol-3-yl)-2-(2,6-difluorophenyl)acetamide;

1H-NMR (400 MHz, DMSO-d6) ppm 10.52 (s, 1H, NHCO), 7.4–7.0 (m, 3H, Ph), 6.06 (s, 1H, CH-pyrazole), 3.68 (s, 2H, COCH2), 1.81 (m, 1H, cyclopropyl-CH);

ESI (+) MS: m/z 278 (100, MH+);

N-(5-cyclopropyl-1H-pyrazol-3-yl)-2-(2-fluorophenyl)acetamide;

1H-NMR (400 MHz, DMSO-d6) ppm 10.45 (s, 1H, NHCO), 7.3–7.1 (m, 4H, Ph), 6.08 (s, 1H, CH-pyrazole), 3.64 (s, 2H, COCH2), 1.81 (m, 1H, cyclopropyl-CH);

ESI (+) MS: m/z 260 (100, MH+);

N-(5-cyclopropyl-1H-pyrazol-3-yl)-2-(2-trifluoromethylphenyl)acetamide;

1H-NMR (400 MHz, DMSO-d6) ppm 10.45 (s, 1H, NHCO), 7.6–7.4 (m, 4H, Ph), 6.06 (s, 1H, CH-pyrazole), 3.83 (s, 2H, COCH2), 1.81 (m, 1H, cyclopropyl-CH);

ESI (+) MS: m/z 310 (100, MH+);

N-(5-cyclopropyl-1H-pyrazol-3-yl)-2-(3-fluorophenyl)acetamide;

1H-NMR (400 MHz, DMSO-d6) ppm 10.46 (s, 1H, NHCO), 7.3–7.0 (m, 4H, Ph), 6.08 (s, 1H, CH-pyrazole), 3.58 (s, 2H, COCH2), 1.81 (m, 1H, cyclopropyl-CH);

ESI (+) MS: m/z 260 (100, MH+);

N-(5-cyclopropyl-1H-pyrazol-3-yl)-2-(3bromophenyl)acetamide;

1H-NMR (400 MHz, DMSO-d6) ppm 10.46 (s, 1H, NHCO), 7.5–7.2 (m, 4H, Ph), 6.08 (s, 1H, CH-pyrazole), 3.56 (s, 2H, COCH2), 1.81 (m, 1H, cyclopropyl-CH);

ESI (+) MS: m/z 320 (100, MH+);

N-(5-cyclopropyl-1H-pyrazol-3-yl)-2-(3,4-dichlorophenyl)acetamide;

1H-NMR (400 MHz, DMSO-d6) ppm 10.49 (s, 1H, NHCO), 6.08 (s, 1H, CH-pyrazole), 3.59 (s, 2H, COCH2), 1.81 (m, 1H, cyclopropyl-CH);

ESI (+) MS: m/z 310 (100, MH+);

N-(5-cyclopropyl-1H-pyrazol-3-yl)-2-(3-trifluoromethylphenyl)acetamide;

1H-NMR (400 MHz, DMSO-d6) ppm 10.51 (s, 1H, NHCO), 6.08 (s, 1H, CH-pyrazole), 3.68 (s, 2H, COCH2), 1.81 (m, 1H, cyclopropyl-CH);
ESI (+) MS: m/z 310 (100, MH+);

N-(5-cyclopropyl-1H-pyrazol-3-yl)-2-(2,6-dichlorophenyl)acetamide;

1H-NMR (400 MHz, DMSO-d6) ppm 10.54 (s, 1H, NHCO), 7.5–7.3 (m, 3H, Ph), 6.04 (s, 1H, CH-pyrazole), 3.96 (s, 2H, COCH2), 1.81 (m, 1H, cyclopropyl-CH);
ESI (+) MS: m/z 310 (100, MH+);

N-(5-cyclopropyl-1H-pyrazol-3-yl)-2-(3,4-difluorophenyl)acetamide;

1H-NMR (400 MHz, DMSO-d6) ppm 10.43 (s, 1H, NHCO), 6.08 (s, 1H, CH-pyrazole), 3.57 (s, 2H, COCH2), 1.81 (m, 1H, cyclopropyl-CH);
ESI (+) MS: m/z 278 (100, MH+);

N-(5-cyclopropyl-1H-pyrazol-3-yl)-2-(3,5-dimethoxyphenyl)acetamide;

1H-NMR (400 MHz, DMSO-d6) ppm 10.35 (s, 1H, NHCO), 6.45 (d, J=2.4 Hz, 2H, CH-o-Ph), 6.08 (s, 1H, CH-pyrazole), 3.78 (s, 2H, COCH2), 1.81 (m, 1H, cyclopropyl-CH);
ESI (+) MS: m/z 302 (100, MH+);

N-(5-cyclopropyl-1H-pyrazol-3-yl)-2-(3-methylphenyl)acetamide;

1H-NMR (400 MHz, DMSO-d6) ppm 10.38 (s, 1H, NHCO), 7.2–7.0 (m, 4H, Ph), 6.08 (s, 1H, CH-pyrazole), 3.50 (s, 2H, COCH2), 1.81 (m, 1H, cyclopropyl-CH);
ESI (+) MS: m/z 256 (100, MH+);

N-(5-cyclopropyl-1H-pyrazol-3-yl)-2-(2-methylphenyl)acetamide;

1H-NMR (400 MHz, DMSO-d6) ppm 10.37 (s, 1H, NHCO), 7.2–7.0 (m, 4H, Ph), 6.08 (s, 1H, CH-pyrazole), 3.59 (s, 2H, COCH2), 1.81 (m, 1H, cyclopropyl-CH);
ESI (+) MS: m/z 256 (100, MH+);

N-(5-cyclopropyl-1H-pyrazol-3-yl)-2-(4-hydroxy-3-nitrophenyl)acetamide;

1H-NMR (400 MHz, DMSO-d6) ppm 10.45 (s, 1H, NHCO), 6.08 (s, 1H, CH-pyrazole), 3.54 (s, 2H, COCH2), 1.81 (m, 1H, cyclopropyl-CH);
ESI (+) MS: m/z 303 (100, MH+);

N-(5-cyclopropyl-1H-pyrazol-3-yl)-2-(4-ethoxyphenyl)acetamide;

1H-NMR (400 MHz, DMSO-d6) ppm 10.35 (s, 1H, NHCO), 6.07 (s, 1H, CH-pyrazole), 3.96 (q, J=7 Hz, 2H, OCH2), 3.45 (s, 2H, COCH2), 1.81 (m, 1H, cyclopropyl-CH);
ESI (+) MS: m/z 286 (100, MH+);

N-(5-cyclopropyl-1H-pyrazol-3-yl)-2-(2,4,6-trimethylphenyl)acetamide;

1H-NMR (400 MHz, DMSO-d6) ppm 10.31 (s, 1H, NHCO), 6.78 (s, 2H, Ph), 6.05 (s, 1H, CH-pyrazole), 3.60 (s, 2H, COCH2), 1.81 (m, 1H, cyclopropyl-CH);
ESI (+) MS: m/z 284 (100, MH+);

N-(5-cyclopropyl-1H-pyrazol-3-yl)-2-(4-trifluoromethoxyphenyl)acetamide;

1H-NMR (400 MHz, DMSO-d6) ppm 10.48 (s, 1H, NHCO), 7.4–7.2 (m, 4H, Ph), 6.08 (s, 1H, CH-pyrazole), 3.60 (s, 2H, COCH2), 1.81 (m, 1H, cyclopropyl-CH);
ESI (+) MS: m/z 326 (100, MH+);

N-(5-cyclopropyl-1H-pyrazol-3-yl)-2-(2-nitrophenyl)acetamide;

1H-NMR (400 MHz, DMSO-d6) ppm 10.47 (s, 1H, NHCO), 8.0–7.5 (m, 4H, Ph), 6.01 (s, 1H, CH-pyrazole), 4.03 (s, 2H, COCH2), 1.81 (m, 1H, cyclopropyl-CH);
ESI (+) MS: m/z 287 (100, MH+);

N-(5-cyclopropyl-1H-pyrazol-3-yl)-2-(3,4,5-trimethoxyphenyl)acetamide;

1H-NMR (400 MHz, DMSO-d6) ppm 10.36 (s, 1H, NHCO), 6.60 (s, 2H, Ph), 6.08 (s, 1H, CH-pyrazole), 3.60 (s, 2H, COCH2), 1.81 (m, 1H, cyclopropyl-CH);
ESI (+) MS: m/z 332 (100, MH+);

N-(5-cyclopropyl-1H-pyrazol-3-yl)-2-(2-methoxyphenyl)acetamide;

1H-NMR (400 MHz, DMSO-d6) ppm 10.22 (s, 1H, NHCO), 7.2–6.8 (m, 4H, Ph), 6.07 (s, 1H, CH-pyrazole), 3.54 (s, 2H, COCH2), 1.81 (m, 1H, cyclopropyl-CH);
ESI (+) MS: m/z 272 (100, MH+);

N-(5-cyclopropyl-1H-pyrazol-3-yl)-2-(4-butoxyphenyl)acetamide;

1H-NMR (400 MHz, DMSO-d6) ppm 10.35 (s, 1H, NHCO), 7.17 (dd, J=7.2 Hz, 2H, CH-o-Ph), 6.07 (s, 1H, CH-pyrazole), 3.45 (s, 2H, COCH2), 1.81 (m, 1H, cyclopropyl-CH);
ESI (+) MS: m/z 314 (100, MH+);

N-(5-cyclopropyl-1H-pyrazol-3-yl)-2-(pentafluorophenyl)acetamide;

1H-NMR (400 MHz, DMSO-d6) ppm 10.63 (s, 1H, NHCO), 6.07 (s, 1H, CH-pyrazole), 3.80 (s, 2H, COCH2), 1.81 (m, 1H, cyclopropyl-CH);
ESI (+) MS: m/z 332 (100, MH+);

N-(5-cyclopropyl-1H-pyrazol-3-yl)-2-(4-methylsulfanylphenyl)acetamide;

1H-NMR (400 MHz, DMSO-d6) ppm 10.40 (s, 1H, NHCO), 7.20 (m, 4H, Ph), 6.07 (s, 1H, CH-pyrazole), 3.50 (s, 2H, COCH2), 1.81 (m, 1H, cyclopropyl-CH);
ESI (+) MS: m/z 288 (100, MH+);

N-(5-cyclopropyl-1H-pyrazol-3-yl)-2-(2-bromophenyl)acetamide;

1H-NMR (400 MHz, DMSO-d6) ppm 10.44 (s, 1H, NHCO), 7.6–7.2 (m, 4H, Ph), 6.08 (s, 1H, CH-pyrazole), 3.76 (s, 2H, COCH2), 1.81 (m, 1H, cyclopropyl-CH);
ESI (+) MS: m/z 320 (100, MH+);

N-(5-cyclopropyl-1H-pyrazol-3-yl)-2-[2,5-bis(trifluoromethyl)phenyl]acetamide;

1H-NMR (400 MHz, DMSO-d6) ppm 10.55 (s, 1H, NHCO), 8.0–7.8 (m, 3H, Ph), 6.05 (s, 1H, CH-pyrazole), 3.98 (s, 2H, COCH2), 1.81 (m, 1H, cyclopropyl-CH);
ESI (+) MS: m/z 378 (100, MH+);

N-(5-cyclopropyl-1H-pyrazol-3-yl)-2-(3-nitrophenyl)acetamide;

1H-NMR (400 MHz, DMSO-d6) ppm 10.56 (s, 1H, NHCO), 6.09 (s, 1H, CH-pyrazole), 3.74 (s, 2H, COCH2), 1.81 (m, 1H, cyclopropyl-CH);
ESI (+) MS: m/z 287 (100, MH+);

N-(5-cyclopropyl-1H-pyrazol-3-yl)-2-(2,4-dichlorophenyl)acetamide;

1H-NMR (400 MHz, DMSO-d6) ppm 10.48 (s, 1H, NHCO), 7.6–7.4 (m, 3H, Ph), 6.07 (s, 1H, CH-pyrazole), 3.75 (s, 2H, COCH2), 1.82 (m, 1H, cyclopropyl-CH);
ESI (+) MS: m/z 310 (100, MH+);

N-(5-cyclopropyl-1H-pyrazol-3-yl)-2-(3,5-di-tert-butyl-4-hydroxyphenyl)acetamide;

1H-NMR (400 MHz, DMSO-d6) ppm 10.33 (s, 1H, NHCO), 7.04 (s, 2H, Ph), 6.08 (s, 1H, CH-pyrazole), 3.40 (s, 2H, COCH2), 1.81 (m, 1H, cyclopropyl-CH);
ESI (+) MS: m/z 370 (100, MH+);

N-(5-cyclopropyl-1H-pyrazol-3-yl)-2-(2,3,6-trifluorophenyl)acetamide

1H-NMR (400 MHz, DMSO-d6) ppm 10.58 (s, 1H, NHCO), 7.4–7.1 (m, 2H, Ph), 6.06 (s, 1H, CH-pyrazole), 3.74 (s, 2H, COCH2), 1.81 (m, 1H, cyclopropyl-CH);
ESI (+) MS: m/z 296 (100, MH+);

N-(5-cyclopropyl-1H-pyrazol-3-yl)-2-(3-methylsulfonylaminophenyl)acetamide;

1H-NMR (400 MHz, DMSO-d6) ppm 10.39 (s, 1H, NHCO), 6.08 (s, 1H, CH-pyrazole), 3.58 (s, 2H, COCH2), 1.81 (m, 1H, cyclopropyl-CH);
ESI (+) MS: m/z 350 (100, MH+);

N-(5-cyclopropyl-1H-pyrazol-3-yl)-2-(4-fluorophenyl)acetamide;

1H-NMR (400 MHz, DMSO-d6) ppm 10.43 (s, 1H, NHCO), 7.4–7.0 (m, 4H, Ph), 6.08 (s, 1H, CH-pyrazole), 3.55 (s, 2H, COCH2), 1.81 (m, 1H, cyclopropyl-CH);
ESI (+) MS: m/z 260 (100, MH+);

N-(3-cyclopropyl-1H-pyrazol-5-yl)-2-(2,3-dihydro-1H-inden-5-yl)acetamide;

1H-NMR (400 MHz, DMSO-d6) ppm 10.35 (s, 1H, NHCO), 7.2–7.0 (m, 3H, Ph), 6.07 (s, 1H, CH-pyrazole), 3.48 (s, 2H, COCH2), 1.81 (m, 1H, cyclopropyl-CH);
ESI (+) MS: m/z 282 (100, MH+);

N-(5-cyclopropyl-1H-pyrazol-3-yl)-2-[3-(2-amino-2-oxoethoxy)phenyl]acetamide;

1H-NMR (400 MHz, DMSO-d6) ppm 10.41 (s, 1H, NHCO), 6.08 (s, 1H, CH-pyrazole), 4.37 (s, 2H, COCH2O), 1.81 (m, 1H, cyclopropyl-CH);
ESI (+) MS: m/z 315 (100, MH+);

N-(5-cyclopropyl-1H-pyrazol-3-yl)-2-{4-[2-oxo-2-(1-pyrrolidinyl)ethoxy]phenyl}acetamide;

1H-NMR (400 MHz, DMSO-d6) ppm 10.37 (s, 1H, NHCO), 6.07 (s, 1H, CH-pyrazole), 4.64 (s, 2H, COCH2O), 1.81 (m, 1H, cyclopropyl-CH);
ESI (+) MS: m/z 369 (100, MH+);

N-(3-cyclopropyl-1H-pyrazol-5-yl)-2-(2-fluoro[1,1'-biphenyl]-4-yl)propanamide;

1H-NMR (400 MHz, DMSO-d6) ppm 10.45 (s, 1H, NHCO), 6.11 (s, 1H, CH-pyrazole), 3.82 (q, J=7 Hz, 1H, NHCOCH), 1.81 (m, 1H, cyclopropyl-CH);
ESI (+) MS: m/z 350 (100, MH+);

N-(3-cyclopropyl-1H-pyrazol-5-yl)-2-oxo-2-(2-thienyl)acetamide;

1H-NMR (400 MHz, DMSO-d6) ppm 10.85 (s, 1H, NHCO), 6.25 (s, 1H, CH-pyrazole), 1.81 (m, 1H, cyclopropyl-CH);
ESI (+) MS: m/z 262 (100, MH+);

N-(5-cyclopropyl-1H-pyrazol-3-yl)-2-(4-nitrophenyl)propanamide;

1H-NMR (400 MHz, DMSO-d6) ppm 10.51 (s, 1H, NHCO), 6.11 (s, 1H, CH-pyrazole), 3.98 (q, J=7 Hz, 1H, NHCOCH), 1.81 (m, 1H, cyclopropyl-CH);
ESI (+) MS: m/z 301 (100, MH+);

2-cyclohexyl-N-(3-cyclopropyl-1H-pyrazol-5-yl)-2-phenylacetamide;

1H-NMR (400 MHz, DMSO-d6) ppm 10.36 (s, 1H, NHCO), 7.4–7.1 (m, 5H, Ph), 6.09 (s, 1H, CH-pyrazole), 3.15 (m, 1H, NHCOCH), 1.80 (m, 1H, cyclopropyl-CH);
ESI (+) MS: m/z 324 (100, MH+);

(2R)-N-(3-cyclopropyl-1H-pyrazol-5-yl)-2-methoxy-2-phenylethanamide;

1H-NMR (400 MHz, DMSO-d6) ppm 10.23 (s, 1H, NHCO), 7.4–7.2 (m, 5H, Ph), 6.08 (s, 1H, CH-pyrazole), 4.83 (s, 1H, NHCOCHPh), 1.81 (m, 1H, cyclopropyl-CH);
ESI (+) MS: m/z 272 (100, MH+);

(2S)-2-amino-N-(3-cyclopropyl-1H-pyrazol-5-yl)-2-phenylethanamide;

1H-NMR (400 MHz, DMSO-d6) ppm 10.95 (s, 1H, NHCO), 7.5–7.4 (m, 5H, Ph), 6.15 (s, 1H, CH-pyrazole), 4.99 (m, 1H, NHCOCH), 1.82 (m, 1H, cyclopropyl-CH);
ESI (+) MS: m/z 257 (100, MH+);

(2S)-N-(3-cyclopropyl-1H-pyrazol-5-yl)-2,5-dihydro-1H-pyrrole-2-carboxamide;

1H-NMR (400 MHz, DMSO-d6) ppm 10.18 (s, 1H, NHCO), 6.14 (s, 1H, CH-pyrazole), 4.1–3.9 (m, 1H, NHCOCH), 1.81 (m, 1H, cyclopropyl-CH);
ESI (+) MS: m/z 219 (100, MH+);

N-(5-cyclopropyl-1H-pyrazol-3-yl)-2-(2,4-dichlorophenoxy)acetamide;

1H-NMR (400 MHz, DMSO-d6) ppm 10.37 (s, 1H, NHCO), 6.12 (s, 1H, CH-pyrazole), 4.80 (s, 2H, NHCOCH2), 1.81 (m, 1H, cyclopropyl-CH);
ESI (+) MS: m/z 226 (100, MH+);

N-(5-cyclopropyl-1H-pyrazol-3-yl)-2-phenoxyacetamide;

1H-NMR (400 MHz, DMSO-d6) ppm 10.30 (s, 1H, NHCO), 7.26 (m, 2H, CH-m-Ph), 6.13 (s, 1H, CH-pyrazole), 4.64 (s, 2H, NHCOCH2), 1.81 (m, 1H, cyclopropyl-CH);
ESI (+) MS: m/z 258 (100, MH+);

(2S)-N-(3-cyclopropyl-1H-pyrazol-5-yl)-2-methoxy-2-phenylethanamide;

1H-NMR (400 MHz, DMSO-d6) ppm 10.23 (s, 1H, NHCO), 7.4–7.2 (m, 5H, Ph), 6.08 (s, 1H, CH-pyrazole), 4.83 (s, 1H, NHCOCHPh), 1.81 (m, 1H, cyclopropyl-CH);
ESI (+) MS: m/z 272 (100, MH+);

(2S)-N-(3-cyclopropyl-1H-pyrazol-5-yl)-3,3,3-trifluoro-2-methoxy-2-phenylpropanamide;

1H-NMR (400 MHz, DMSO-d6) ppm 10.30 (s, 1H, NHCO), 7.5–7.4 (m, 5H, Ph), 6.14 (s, 1H, CH-pyrazole), 1.83 (m, 1H, cyclopropyl-CH);
ESI (+) MS: m/z 340 (100, MH+);

N-(5-cyclopropyl-1H-pyrazol-3-yl)-1-phenylcyclopentane-1-carboxamide;

1H-NMR (400 MHz, DMSO-d6) ppm 10.32 (s, 1H, NHCO), 6.09 (s, 1H, CH-pyrazole), 3.20 (m, 1H, cyclopentyl-CH), 1.81 (m, 1H, cyclopropyl-CH);
ESI (+) MS: m/z 310 (100, MH+);

9H-fluoren-9-yl (2S)-2-{[(3-cyclopropyl-1H-pyrazol-5-yl)amino]carbonyl}-2,5-dihydro-1H-pyrrole-1-carboxylate;

1H-NMR (400 MHz, DMSO-d6, syn/anti isomers) ppm 10.67/10.45 (2s, 1H, NHCO), 6.20/6.05 (2s, 1H, CH-pyrazole), 4.4–4.0 (m, 3H, COOCH2CH);
ESI (+) MS: m/z 441 (100, MH+);

(1R)-2-[(3-cyclopropyl-1H-pyrazol-5-yl)amino]-2-oxo-1-phenylethyl acetate;

1H-NMR (400 MHz, DMSO-d6) ppm 10.67 (s, 1H, NHCO), 7.5–7.3 (m, 5H, Ph), 6.08 (s, 1H, CH-pyrazole), 5.94 (s, 1H, COCHPh);
ESI (+) MS: m/z 300 (100, MH+);

N-(5-cyclopropyl-1H-pyrazol-3-yl)-2-{4-[(2S)-2-aminopropanoyloxymethyl]phenyl}acetamide;

1H-NMR (400 MHz, DMSO-d6) ppm 10.44 (s, 1H, NHCO), 7.30 (m, 4H, Ph), 6.07 (s, 1H, CH-pyrazole), 3.59 (s, 2H, COCH2), 1.81 (m, 1H, cyclopropyl-CH);
ESI (+) MS: m/z 343 (100, MH+);

(1S)-2-[(3-cyclopropyl-1H-pyrazol-5-yl)amino]-2-oxo-1-phenylethyl acetate;

1H-NMR (400 MHz, DMSO-d6) ppm 10.67 (s, 1H, NHCO), 7.5–7.3 (m, 5H, Ph), 6.08 (s, 1H, CH-pyrazole), 5.94 (s, 1H, COCHPh); 1.81 (m, 1H, cyclopropyl-CH);
ESI (+) MS: m/z 300 (100, MH+);

N-(3-cyclopropyl-1H-pyrazol-5-yl)-2-fluoro-2-phenylacetamide;

1H-NMR (400 MHz, DMSO-d6) ppm 10.67 (s, 1H, NHCO), 7.3–7.4 (m, 5H, Ph), 6.10 (s, 1H, CH-pyrazole), 5.95 (d, J=47.5, 1H, CHF), 1.82 (m, 1H, cyclopropyl-CH);
ESI (+) MS: m/z 260 (100, MH+);

N-(3-cyclopropyl-1H-pyrazol-5-yl)-3-methyl-2-phenylpentanamide;

1H-NMR (400 MHz, DMSO-d6) ppm 7.4–7.1 (m, 5H, Ph), 6.09 (s, 1H, CH-pyrazole), 3.75 (d, J=10.0, 1H, COCH), 1.82 (m, 1H, cyclopropyl-CH);
ESI (+) MS: m/z 298 (100, MH+);

N-(3-cyclopropyl-1H-pyrazol-5-yl)-2-(3,4-dimethoxyphenyl)acetamide;

1H-NMR (400 MHz, DMSO-d6) ppm 6.9–6.7 (m, 3H, Ph), 6.07 (s, 1H, CH-pyrazole), 3.50 (s, 2H, COCH2), 1.81 (m, 1H, cyclopropyl-CH);
ESI (+) MS: m/z 302 (100, MH+);

2-(4-chlorophenyl)-N-(3-cyclopropyl-1H-pyrazol-5-yl)acetamide;

1H-NMR (400 MHz, DMSO-d6) ppm 7.4–7.3 (m, 4H, Ph), 6.09 (s, 1H, CH-pyrazole), 3.56 (s, 2H, COCH2), 1.82 (m, 1H, cyclopropyl-CH);
ESI (+) MS: m/z 276 (100, MH+);

N-(3-cyclopropyl-1H-pyrazol-5-yl)-2-(1-naphthyl)acetamide;

1H-NMR (400 MHz, DMSO-d6) ppm 6.07 (s, 1H, CH-pyrazole), 4.07 (s, 2H, COCH2), 1.80 (m, 1H, cyclopropyl-CH);
ESI (+) MS: m/z 292 (100, MH+);

N-(3-cyclopropyl-1H-pyrazol-5-yl)-2-(5-methoxy-1H-indol-3-yl)acetamide;

1H-NMR (400 MHz, DMSO-d6) ppm 7.17 (s, 1H, CCHNH), 6.10 (s, 1H, CH-pyrazole), 3.60 (s, 2H, COCH2), 1.80 (m, 1H, cyclopropyl-CH);
ESI (+) MS: m/z 311 (100, MH+);

N-(3-cyclopropyl-1H-pyrazol-5-yl)-2-(1-methyl-1H-indol-3-yl)acetamide;

1H-NMR (400 MHz, DMSO-d6) ppm 7.19 (s, 1H, CCHNCH3), 6.09 (s, 1H, CH-pyrazole), 3.64 (s, 2H, COCH2), 1.80 (m, 1H, cyclopropyl-CH);
ESI (+) MS: m/z 295 (100, MH+);

2-(5-chloro-1-benzothiophen-3-yl)-N-(3-cyclopropyl-1H-pyrazol-5-yl)acetamide;

1H-NMR (400 MHz, DMSO-d6) ppm 7.66 (s, 1H, CCHS), 6.08 (s, 1H, CH-pyrazole), 3.85 (s, 2H, COCH2), 1.82 (m, 1H, cyclopropyl-CH);
ESI (+) MS: m/z 332 (100, MH+);

2-(1-benzothiophen-3-yl)-N-(3-cyclopropyl-1H-pyrazol-5-yl)acetamide;

1H-NMR (400 MHz, DMSO-d6) ppm 7.54 (s, 1H, CCHS), 6.10 (s, 1H, CH-pyrazole), 3.85 (s, 2H, COCH2), 1.82 (m, 1H, cyclopropyl-CH);
ESI (+) MS: m/z 298 (100, MH+);

N-(3-cyclopropyl-1H-pyrazol-5-yl)-2-(4-methylphenyl)acetamide;

1H-NMR (400 MHz, DMSO-d6) ppm 7.2–7.1 (m, 4H, Ph), 6.08 (s, 1H, CH-pyrazole), 2.25 (s, 3H, CH3), 1.81 (m, 1H, cyclopropyl-CH);
ESI (+) MS: m/z 256 (100, MH+);

N-(3-cyclopropyl-1H-pyrazol-5-yl)-2-oxo-2-phenylacetamide;

1H-NMR (400 MHz, DMSO-d6) ppm 7.94 (d, J=7.5 Hz, 2H, o-Ph), 7.74 (t, J=7.5 Hz, 1H, p-Ph), 6.27 (s, 1H, CH-pyrazole), 1.89 (m, 1H, cyclopropyl-CH);
ESI (+) MS: m/z 256 (100, MH+);

N-(3-cyclopropyl-1H-pyrazol-5-yl)-2-methoxy-2-phenylacetamide;

1H-NMR (400 MHz, DMSO-d6) 7.4–7.2 (m, 5H, Ph), 6.05 (s, 1H, CH-pyrazole), 4.80 (s, 1H, COCH), 1.82 (m, 1H, cyclopropyl-CH);
ESI (+) MS: m/z 272 (100, MH+);

N-(3-cyclopropyl-1H-pyrazol-5-yl)-3-cyclopentylpropanamide;

1H-NMR (400 MHz, DMSO-d6) 6.07 (s, 1H, CH-pyrazole), 2.15 (t, J=8 Hz, 2H, COCH2), 1.82 (m, 1H, cyclopropyl-CH);
ESI (+) MS: m/z 248 (100, MH+);

N-(3-cyclopropyl-1H-pyrazol-5-yl)-4-oxo-4-phenylbutanamide;

1H-NMR (400 MHz, DMSO-d6) 7.85 (d, J=8 Hz, 2H, CH-o-Ph), 6.05 (s, 1H, CH-pyrazole), 1.82 (m, 1H, cyclopropyl-CH);

ESI (+) MS: m/z 284 (100, MH+);

N-(3-cyclopropyl-1H-pyrazol-5-yl)-4-phenyl-3-butenamide;

1H-NMR (400 MHz, DMSO-d6) 6.49 (d, J=15.8 Hz, 1H, CHPh), 6.15 (s, 1H, CH-pyrazole), 3.2 (d, J=7.7 Hz, 2H, COCH2), 1.83 (m, 1H, cyclopropyl-CH);

ESI (+) MS: m/z 268 (100, MH+);

N-(3-cyclopropyl-1H-pyrazol-5-yl)-2-phenylpropanamide;

1H-NMR (400 MHz, DMSO-d6) 7.4–7.2 (m, 5H, Ph), 6.08 (s, 1H, CH-pyrazole), 3.79 (s, 1H, COCH), 1.81 (m, 1H, cyclopropyl-CH);

ESI (+) MS: m/z 256 (100, MH+);

N-(3-cyclopropyl-1H-pyrazol-5-yl)-2-[4-(dimethylamino)phenyl]acetamide;

N-(3-cyclopropyl-1H-pyrazol-5-yl)-1-phenylcyclopropancarboxamide;

N-(3-cyclopropyl-1H-pyrazol-5-yl)-2-(4-methoxyphenyl)acetamide;

N-(3-cyclopropyl-1H-pyrazol-5-yl)-2-(1H-indol-3-yl)acetamide;

3-(2-chlorophenoxy)-N-(3-cyclopropyl-1H-pyrazol-5-yl)propanamide;

N-(3-cyclopropyl-1H-pyrazol-5-yl)-2-(3-chlorophenyl)acetamide;

N-(3-cyclopropyl-1H-pyrazol-5-yl)-2-(2-fluorophenyl)acetamide;

N-(3-cyclopropyl-1H-pyrazol-5-yl)-2-(2-chlorophenyl)acetamide;

N-(3-cyclopropyl-1H-pyrazol-5-yl)-2-(4-trifluoromethylphenyl)acetamide;

N-(3-cyclopropyl-1H-pyrazol-5-yl)-3-oxo-1-indanecarboxamide;

N-(3-cyclopropyl-1H-pyrazol-5-yl)-2-(3-thienyl)acetamide;

N-(3-cyclopropyl-1H-pyrazol-5-yl)bicyclo[4.2.0]octa-1,3,5-triene-7-carboxamide;

All compounds were characterized by mass spectrometry (MS). LC-MS confirmed that in each case the principle component had a molecular ion corresponding to the expected product. The compounds showed an HPLC area % ranging from 78 to 100.

HPLC analysis:
Solvent A: H2O/CH3CN=90/10+0.1% TFA
Solvent B: H2O/CH3CN=10/90+0.075% TFA

| Time (min) | % A | % B |
|---|---|---|
| 0 | 0 | 100 |
| 6.5 | 0 | 100 |
| 7 | 100 | 0 |
| 10 | 100 | 0 |

Rate: 1.5 ml/min
Detection: UV 254 nm
Temperature: room temperature

Column: Supelco™, Discovery RP Amide C16, 5·m, (50×4.6) mm

Example 3

3-Cyclopropyl-3-oxo-propanenitrile 4.5 g (0.15 mol) of sodium hydride 80% were suspended in 200 ml of dioxane, 7.5 ml of acetonitrile (0.15 mol) were dropped and, after 20 minutes, a solution of ethyl cyclopropancarboxylate (0.125 mol) in 100 ml of the same solvent was added. The mixture was maintained at reflux for 3 hours, under stirring, then 400 ml of water were added and the unreacted starting material extracted with methylene chloride. The aqueous layer was acidified with diluted hydrochloric acid and extracted with the same solvent. The organic layer was dried over anhydrous sodium sulfate and evaporated to dryness to give a residue that, after column chromatography (cyclohexane-ethylacetate), afforded 7.8 g (57% yield) of the title compound.

1H-NMR (400 MHz, CDCl3) ppm: 1.20 (m, 2H, cyclopropyl CHH+CHH); 1.21 (m, 2H, CHH+CHN; 2.12 (dddd, 1H, J=7.6, 7.6, 4.5, 4.5, cyclopropyl CH); 3.59 (s, 2H, COCH2).

EI-MS: m/z 69 (85, M-C3H5–); m/z 39 (100, C3H5+).

Example 4

3-Cyclopropyl-5-amino-1H-pyrazole 5 g (0.046 mol) of 3-cyclopropyl-3-oxo-propanenitrile were dissolved in 200 ml of ethanol and 2.26 ml (0.046 mol) of hydrazine hydrate were added. The solution was maintained at reflux for 5 hours and then the solvent evaporated under vacuum. The residue was re-dissolved with methylene chloride and washed several times with brine. The organic layer was dried over anhydrous sodium sulfate and the solvent evaporated to give 4.53 g (80% yield) of the title compound.

1H-NMR (400 MHz, DMSO-d6) ppm: 0.54 (m, 2H, pyrazole CHH+CHH); 0.76 (m, 2H, CHH+CHH); 1.68 (dddd, 1H, J=4.9, 4.9, 8.3, 8.3, pyrazole CH); 5.02 (s, 1H, pyrazole CH); 6–7 (b, 3H, NH+NH2).

ESI (+) MS: m/z 124 (100, MH+).

Analogously the following compounds were prepared:

3-Cyclobutyl-5-amino-1H-pyrazole

1H-NMR (DMSO-d6) ppm 11.10 (br. s, 1H), 5.23 (s, 1H), 4.43 (br. s, 2H), 3.31 (m, 1H), 2.18 (m, 2H), 2.04 (m, 2H), 1.80 (m, 2H);

MS (FAB) m/z 138 (MH+, 100).

3-(2-benzylcyclopropyl)-1H-pyrazol-5-amine hydrochloride

1H-NMR (DMSO-d6) pm 7.23 (complex, 5H), 5.48 (s, 1H), 2.67 (m, 2H), 1.85 (m, 1H), 1.48 (m, 1H), 1.06 (m, 2H);

MS (FAB) m/z 214 (MH+, 100).

3-Cyclopentyl-5-amino-1H-pyrazole

1H-NMR (DMSO-d6) ppm 11.15 (s, 1H), 5.17 (s, 1H), 4.41 (br. s, 2H), 2.49 (m, 1H), 2.20 (complex, 4H), 1.80 (complex, 2H), 1.39 (complex, 2H).

Example 5

3-Cyclopropyl-5-nitro-1H-pyrazole

To a solution of 2.7 g of sodium hydrate in 454 ml of water 7.1 g (0.058 mol) of 3-cyclopropyl-5-amino-1H-pyrazole and 46.5 g of sodium hydrogenocarbonate were added at 0° C. After 10 minutes a solution of 337 ml of acetone in 221 ml of water and a solution of 130 g (0.21 mol) of OXONE® in 580 ml of water were contemporaneously dropped under vigorous stirring. After 4 hours at the same temperature the reaction is quenched with a saturated solution of sodium sulfite and extracted with ethylacetate. The organic layer was dried over anhydrous sodium sulfate and evaporated to dryness to give 4.6 g (52% yield) of the title compound.

1H-NMR (400 MHz, CDCl3) ppm: 0.79 (m, 2H, cyclopropyl CHH+CHH); 1.10 (m, 2H, cyclopropyl CHH+CHH); 2.01 (dddd, 1H, J=5.1, 5.1, 8.2, 8.2, cyclopropyl CH); 6.51 (s, 1H, pyrazole CH).

EI-MS: m/z 153 (100, M+); 136 (60, M-OH).

Example 6

Tert-butyl-3-nitro-5-cyclopropyl-1H-pyrazole-1-carboxylate 4.9 g (0.032 mol) of 3-cyclopropyl-5-nitro-1H-pyrazole were dissolved in 200 ml of methylene chloride and 200 ml of a saturated solution of sodium hydrogenocarbonate were added. 35 g (0.16 mol) of tertbutoxycarbonyl anhydride were then added under stirring at room temperature. After 24 hours the layers were separated and the organic one dried over sodium sulfate and evaporated under vacuum. The residue was chromatographed on a silica gel column (cyclohexane-ethyl acetate) to give 7.7 g (95% yield) of the title compound.

1H-NMR (400 MHz, CDCl3) ppm: 0.78 (m, 2H, cyclopropyl CHH+CHH); 1.13 (m, 2H, CHH+CHH); 1.68 (s, 9H, (CH3)3–); 2.48 (dddd, 1H, J=5.3, 5.3, 8.5, 8.5, cyclopropyl CH); 6.49 (s, 1H, pyrazole CH).

ESI (+) MS: m/z 276 (100, MNa+); 220 [60, MNa-C4H8)+].

Example 7

Tert-butyl-3-amino-5-cyclopropyl-1H-pyrazole-1-carboxylate 1.2 g (4.74 mmol) of tert-butyl-3-nitro-5-cyclopropyl-1-carboxylate were dissolved in 20 ml of ethanol and hydrogenated in presence of 200 mg of palladium on charcoal (10%) at 50 psi and room temperature to give, after filtration on celite and evaporation of the solvent, 0.96 g (95% yield) of the title compound.

1H-NMR (400 MHz, CDCl3) ppm: 0.64 (m, 2H, cyclopropyl CHH+CHH); 0.97 (m, 2H cyclopropyl CHH+CHH); 1.63 (s, 9H, (CH3)3); 2.34 (dddd, 1H, J=5.2, 5.2, 8.4, 8.4, cyclopropyl CH); 3.82 (s b, 2H, NH2); 5.39 (s, 1H, pyrazole CH).

ESI (+) MS: m/z 246 (20, MNa+); 168 [100, (MH-C4H8)+]; 124 [90, [MH-C5H8O2)+].

Example 8

N-(3-cyclopropyl-1H-pyrazol-5-yl)benzamide

To a solution of 0.37 g (3 mmol) of 3-cyclopropyl-5-amino-1H-pyrazole in 15 ml of dichloromethane 0.8 ml (7.3 mmol) of N-methylmorpholine and 0.8 ml (6.9 mmol) of benzoyl chloride were successively added at room temperature. After 16 hours under stirring the mixture was concentrated and the residue was dissolved in 15 ml of methanol. 3.5 ml of sodium hydrate 2.5 M were added dropwise and 10 ml of tetrahydrofuran were finally added in order to obtain a homogeneous solution. After 15 minutes the mixture was concentrated and poured into water. The precipitate was filtered and dried in vacuum to afford 585 mg (86% yield) the title compound.

m.p. 234° C.;

1H NMR (DMSO-d6) ppm 12.1 (s, 1H), 10.65 (s, 1H), 7.97 (app.d, 2H), 7.7 (m, 3H), 6.31 (s, 1H), 1.89 (m, 1H), 0.93 (m, 2H), 0.69 (m, 2H);

MS (EI) m/z (rel. intensity) 227 (M+, 22), 226 (11), 199 (23), 106 (13), 105 (95), 78 (11), 77 (99), 66 (9), 65 (14), 51 (29).

Analogously, the following products were prepared starting from the corresponding carboxylic acid:

N-(3-cyclopropyl-1H-pyrazol-5-yl)-4-chlorobenzamide m.p. 186–187° C.;

1H NMR (DMSO-d6) ppm 12.2 (s, 1H), 10.8 (s, 1H), 7.97 (app.d, 2H), 7.53 (app.d, 2H), 6.28 (s, 1H), 1.87 (m, 1H), 0.91 (m, 2H), 0.67 (m, 2H);

MS (EI) m/z (rel. intensity) 261 (M+, 27), 235 (8), 233 (36), 141 (66), 139 (99), 113 (31), 111 (78), 65 (10).

N-(3-cyclopropyl-1H-pyrazol-5-yl)-4-methoxybenzamide;

m.p. 175–176° C.;

1H NMR (DMSO-d6) ppm 12.11 (s, 1H), 10.51 (s, 1H), 7.97 (d, J=8.8 Hz, 2H), 7.00 (d, J=8.8 Hz, 2H), 6.26 (s, 1H), 3.80 (s, 3H), 1.86 (m, 1H), 0.91 (m, 2H), 0.67 (m, 2H);

MS (EI) m/z (rel. intensity) 257 (M+, 32), 257 (32), 229 (14), 135 (99), 107 (19), 92 (38), 77 (58), 74 (15), 73 (18), 65 (17), 64 (18).

N-(3-cyclopropyl-1H-pyrazol-5-yl)-4-butoxybenzamide;

m.p. 192° C.;

1H NMR (DMSO-d6) ppm 12.11 (s, 1H), 10.48 (s, 1H), 7.95 (d, J=8.8 Hz, 2H), 6.98 (d, J=8.7 Hz, 2H), 6.26 (s, 1H), 4.01 (t, J=6.5 Hz, 2H), 1.86 (m, 1H), 1.69 (m, 2H), 1.43 (m, 2H), 0.92 (m, 5H), 0.66 (m, 2H);

MS (EI) m/z (rel. intensity) 299 (M+, 58), 299 (58), 271 (25), 177 (92), 121 (99), 93 (66), 92 (16), 67 (16), 65 (62), 63 (17).

N-(5-cyclopropyl-1H-pyrazol-3-yl)[1,1'-biphenyl]-4-carboxamide;

m.p. 253–254° C.;

1H NMR (DMSO-d6) ppm 12.15 (s, 1H), 10.7 (s, 1H), 8.05 (d, J=8 Hz, 2H), 7.76 (d, J=8 Hz, 2H), 7.72 (d, J=7 Hz, 2H), 7.48 (t, J=7 Hz, 2H), 7.39 (t, J=7 Hz, 1H), 6.31 (br s, 1H), 1.88 (m, 1H), 0.91 (m, 2H), 0.68 (m, 2H);

MS (FAB) m/z (rel. intensity) 304 (M+, 83), 152 (34), 151 (47), 128 (36), 107 (50), 95 (38), 89 (32), 78 (27), 77 (99), 39 (35).

N-(3-cyclopropyl-1H-pyrazol-5-yl)phenylacetamide m.p. 208° C.;

1H NMR (DMSO-d6) ppm 12.05 (s, 1H), 10.5 (s, 1H), 7.28 (app.d, 4H), 7.21 (m, 1H), 6.10 (s, 1H), 3.54 (s, 2H), 1.80 (m, 1H), 0.86 (m, 2H), 0.59 (m, 2H);

MS (EI) m/z (rel. intensity) 241 (M+, 64), 123 (99), 118 (10), 96 (16), 95 (9), 91 (99), 80 (35), 73 (14), 66 (10), 65 (48).

N-(3-cyclopropyl-1H-pyrazol-5-yl)-3-phenylpropanamide m.p. 152–160° C.;

1H NMR (DMSO-d6) ppm 12.00 (br s, 1H), 10.25 (s, 1H), 7.21 (m, 5H), 6.12 (s, 1H), 2.83 (t, J=8 Hz, 2H), 2.53 (t, J=8 Hz, 2H), 1.82 (m, 1H), 0.87 (m, 2H), 0.61 (m, 2H);

MS (FAB) m/z (rel. intensity) 256 (MH+, 99), 255 (18), 219 (15), 167 (9), 150 (9), 135 (10), 107 (26), 105 (23), 93 (9), 89 (28).

N-(3-cyclopropyl-1H-pyrazol-5-yl)-3-trifluoromethylbenzamide;

m.p. 193–194° C.;

1H-NMR (DMSO-d6) ppm 12.25 (s, 1H), 11.00 (s, 1), 8.32 (s, 1H), 8.26 (d, J=7.9 Hz, 1H), 7.90 (d, 1H), 7.71 (t, 1H), 6.31 (s, 1H), 1.88 (m, 1H), 0.92 (m, 2H). 0.62 (m, 2H);

MS (EI) m/z (rel. intensity) 295 (M+, 15), 295 (15), 267 (21), 266 (10), 173 (99), 145 (99), 126 (13), 95 (18), 75 (15), 66 (19), 65 (18).

N-(3-cyclopropyl-1H-pyrazol-5-yl)-1-benzothiophene-2-carboxamide m.p. 238–239° C.;

1H NMR (DMSO-d6) ppm 12.2 (s, 1H), 11.1 (s, 1H), 8.39 (s, 1H), 8.01 (app.d, 1H), 7.91 (app.d, 1H), 7.44 (m, 2H), 6.28 (s, 1H), 1.88 (m, 1H), 0.91 (m, 2H), 0.67 (m, 2H);

MS (EI) m/z (rel. intensity) 283 (M+, 78), 255 (18), 162 (23), 161 (99), 133 (75), 89 (93), 73 (18), 65 (14), 63 (11).

4-[(4-chlorophenyl)sulphonyl]-N-(5-cyclopropyl-1H-pyrazol-3-yl)-3-methyl-2-thiophenecarboxamide 1H-NMR (DMSO-d6) ppm 10.81 (s, 1H), 8.67 (s, 1H), 7.93–7.91 (d, J=7 Hz, 2H), 7.74–7.71 (d, J=9 Hz, 2H), 6.16 (s, 1H), 2.32 (s, 3H), 1.87 (m, 1H), 0.91 (m, J=2.8 Hz, 2H), 0.67 (m, J=2.5 Hz, 2H);

MS (FAB) m/z (rel. intensity) 422 (MH+, 100).

N¹-(3-cyclopropyl-1H-pyrazol-5-yl)terephthalamide;

m.p. 262–263° C.

1H-NMR (DMSO-d6) ppm 12.2 (s, 1H), 10.85 (s, 1H), 8.09 (s, 1H), 8.01 (d, J=8.0 Hz, 2H), 7.92 (d, J=8.0 Hz, 2H), 7.50 (s, 1H), 6.28 (s, 1H), 1.87 (m, 1H), 0.91 (m, 2H), 067 (m, 2H);

MS (EI) m/z (rel. intensity) 270 (M+, 10), 148 (99), 128 (72), 103 (25), 73 (87), 71 (42), 60 (25), 59 (58), 58 (50).

N-(3-cyclopropyl-1H-pyrazol-5-yl)acetamide;

m.p. 167–171° C.

1H-NMR (DMSO-d6) ppm 12.0 (s, 1H), 10.2 (s, 1H), 6.13 (s, 1H), 1.95 (s, 3H), 1.84 (m, 1H), 0.89 (m, 2H), 0.64 (m, 2H);

MS (EI) m/z (rel. intensity) 165 (M+, 47), 123 (99), 122 (33), 97 (15), 96 (31), 81 (19), 80 (72), 67 (17), 66 (28), 65 (40).

Methyl 4-{[(3-cyclopropyl-1H-pyrazol-5-yl)amino]carbonyl}benzoate;

m.p. 173–174° C.;

1H-NMR (DMSO-d6) ppm 12.2 (s, 1H), 10.9 (s, 1H), 8.06 (d, J=8.0 Hz, 2H), 8.01 (d, J=8.0 Hz, 2H), 6.30 (s, 1H), 3.87 (s, 3H), 1.88 (m, 1H), 0.91 (m, 2H), 0.67 (m, 2H);

MS (EI) m/z (rel. intensity) 285 (M+, 9), 256 (13), 163 (99), 136 (21), 135 (22), 119 (14), 104 (14), 103 (28), 77 (26), 75 (18).

N-(3-cyclopropyl-1H-pyrazol-5-yl)-3-bromobenzamide;

m.p. 158–159° C.

1H-NMR (DMSO-d6) ppm 12.20 (s, 1H), 10.75 (s, 1H), 8.14 (s, 1H), 7.96 (d, J=7.9 Hz, 1H), 7.72 (d, 1H), 7.43 (t, J=7.9 Hz, 1H), 6.28 (s, 1H), 1.87 (m, 1H), 0.92 (m, 2H), 0.67 (m, 2H);

MS (EI) m/z (rel. intensity) 305 (M+, 16), 185 (99), 183 (99), 157 (45), 155 (50), 77 (39), 76 (53), 75 (22), 66 (31), 65 (17), 51 (24).

N-(3-cyclopropyl-1H-pyrazol-5-yl)-3-methoxybenzamide;

m.p. 149° C.;

1H-NMR (DMSO-d6) ppm 12.15 (s, 1H), 10.65 (s, 1H), 7.55 (d, 2H), 7.39–7.36 (t, J=8.0 Hz, 1H), 7.10 (app.D. 1H), 6.29 (s, 1H), 3.80 (s, 3H), 1.87 (m, 1H), 0.92 (m, 2H), 0.67 (m, 2H);

MS (FAB) m/z (rel. intensity) 258 (M+, 100).

4-bromo-N-(5-cyclobutyl-1H-pyrazol-3-yl)benzamide;

m.p. 192–194° C.

MS (EI) m/z (rel. intensity) 319 (M+, 5), 263 (59), 185 (96), 183 (99), 157 (76), 155 (82), 76 (83), 73 (74), 53 (56).

2-[(4-acetylamino)phenyl]-N-(5-cyclopropyl-1H-pyrazol-3-yl)acetamide;

4-bromo-N-(5-cyclohexyl-1H-pyrazol-3-yl)benzamide;

4-bromo-N-(5-cyclopentyl-1H-pyrazol-3-yl)benzamide;

N-[5-(2-benzylcyclopropyl)-1H-pyrazol-3-yl]4-bromobenzamide;

N-(5-cyclopropyl-1H-pyrazol-3-yl)-2,4-dimethoxybenzamide;

5-[(4-chlorophenyl)sulphonyl]-N-(5-cyclopropyl-1H-pyrazol-3-yl)-3-methyl-2-thiophenecarboxamide;

N-(5-cyclopropyl-1H-pyrazol-3-yl)-2,3,4,5,6-pentafluorobenzamide;

N-(5-cyclopropyl-1H-pyrazol-3-yl)-cyclopentancarboxamide;

N-(5-cyclopropyl-1H-pyrazol-3-yl)-2-(2-thienyl)acetamide;

N-(5-cyclopropyl-1H-pyrazol-3-yl)-3,5-dichlorobenzamide;

2-chloro-N-(5-cyclopropyl-1H-pyrazol-3-yl)-6-methyl-isonicotinamide;

N-(5-cyclopropyl-1H-pyrazol-3-yl)-5-isoxazolecarboxamide;

2,4-dichloro-N-(5-cyclopropyl-1H-pyrazol-3-yl)-5-fluorobenzamide;

N-(5-cyclopropyl-1H-pyrazol-3-yl)-2,4-difluorobenzamide;

N-(5-cyclopropyl-1H-pyrazol-3-yl)-3,4-dimethoxybenzamide;

4-{[(3-cyclopropyl-1H-pyrazol-5-yl)amino]carbonyl}benzoic acid;

2-(4-bromophenyl)-N-(5-cyclopropyl-1H-pyrazol-3-yl)-acetamide;

(2S)-N-(5-cyclopropyl-1H-pyrazol-3-yl)-2-(2-naphtyl)propanamide;

N-(5-cyclopropyl-1H-pyrazol-3-yl)-2-[4$^1$-(hydroxymethyl)[1,1$^1$-biphenyl]-4-yl)acetamide;

3-tert-butyl-N-(5-cyclopropyl-1H-pyrazol-3-yl)-1-(2-thienylcarbonyl)-1H-pyrazole-5-carboxamide;

N-(3-{[(3-cyclopropyl-1H-pyrazol-3-yl)amino]carbonyl}-2-thienyl)-2-thiophenecarboxamide;

N-(5-cyclopropyl-1H-pyrazol-3-yl)-2-(4$^1$-fluoro[1,1$^1$-biphenyl]-4-yl)acetamide;

N-(5-cyclopropyl-1H-pyrazol-3-yl)-2,4-dimethyl-5-phenyl-1H-pyrrole-3-carboxamide;

N-(5-cyclopropyl-1H-pyrazol-3-yl)-2-{4$^1$-[(dimethylamino]methyl)[1,1$^1$-biphenyl]-4-yl}acetamide;

2-[4'-(aminomethyl)[1,1'-biphenyl]-4-yl]-N-(5-cyclopropyl-1H-pyrazol-3-yl)acetamide;

N-(5-cyclopropyl-1H-pyrazol-3-yl)-2-{4'-[(methylamino)methyl][1,1'-biphenyl]-4-yl}acetamide;

N-(5-cyclopropyl-1H-pyrazol-3-yl)-2-[4'-(1-pyrrolidinylmethyl)[1,1'-biphenyl]-4-yl]acetamide;

N-(5-cyclopropyl-1H-pyrazol-3-yl)-2-[4'-(1-piperidinylmethyl)[1,1'-biphenyl]-4-yl]acetamide;

N-(5-cyclopropyl-1H-pyrazol-3-yl)-2-[4'-(4-morpholinylmethyl)[1,1'-biphenyl]-4-yl]acetamide;

N-(5-cyclopropyl-1H-pyrazol-3-yl)-2-{4'-[(4-methyl-1-piperazinyl)methyl][1,1'-biphenyl]-4-yl}acetamide;

N-(5-cyclopropyl-1H-pyrazol-3-yl)-2-[4'-(1H-imidazol-2-yl)[1,1'-biphenyl]-4-yl]acetamide;

N-(5-cyclopropyl-1H-pyrazol-3-yl)-2-(4-{[dimethylamino)carbonyl]amino}phenyl)acetamide;

N-(5-cyclopropyl-1H-pyrazol-3-yl)-2-{4-[(methylsulfonyl)amino]phenyl}acetamide;

2-[4-(aminomethyl)phenyl]-N-(5-cyclopropyl-1H-pyrazol-3-yl)acetamide;

2-{4-[(acetylamino)methyl]phenyl}-N-(5-cyclopropyl-1H-pyrazol-3-yl)acetamide;

2-[4-(aminosulfonyl)phenyl]-N-(5-cyclopropyl-1H-pyrazol-3-yl)acetamide;

N-(3-cyclopropyl-1H-pyrazol-5-yl)-4-(2-methoxyphenoxy)benzamide;

4-(4-chlorophenoxy)-N-(3-cyclopropyl-1H-pyrazol-5-yl)benzamide;

4-(4-chlorophenoxy)-N-(3-cyclopropyl-1H-pyrazol-5-yl)-3-nitrobenzamide;

4-[3,5-bis(trifluoromethyl)phenoxy]-N-(3-cyclopropyl-1H-pyrazol-5-yl)benzamide;

N-(3-cyclopropyl-1H-pyrazol-5-yl)-4-(4-fluorophenoxy)benzamide;

N-(3-cyclopropyl-1H-pyrazol-5-yl)-4-(4-methylphenoxy)benzamide;

4-(4-cyanophenoxy)-N-(3-cyclopropyl-1H-pyrazol-5-yl)benzamide;

N-(3-cyclopropyl-1H-pyrazol-5-yl)-4-(4-hydroxyphenoxy)benzamide;

N-(3-cyclopropyl-1H-pyrazol-5-yl)-4-(3-hydroxyphenoxy)benzamide;

2-[1,1'-biphenyl]-4-yl-N-(3-cyclopropyl-1H-pyrazol-5-yl)propanamide;

N-(3-cyclopropyl-1H-pyrazol-5-yl)-2-(4-phenoxyphenyl)acetamide;

N-(3-cyclopropyl-1H-pyrazol-5-yl)-3,5-diiodo-4-(4-methoxyphenoxy)benzamide;

N-(3-cyclopropyl-1H-pyrazol-5-yl)-4-[3-(hydroxymethyl)phenyl]-3-butenamide;

N-(3-cyclopropyl-1H-pyrazol-5-yl)-4-{3-[(methylamino)methyl]phenyl}-3-butenamide;

N-(3-cyclopropyl-1H-pyrazol-5-yl)-2-(2-phenylcyclopropyl)acetamide;

2-[2-(1,3-benzodioxol-5-yl)cyclopropyl]-N-(3-cyclopropyl-1H-pyrazol-5-yl)acetamide;

2-[3-(1,3-benzodioxol-5-yl)-2,2-difluorocyclopropyl]-N-(3-cyclopropyl-1H-pyrazol-5-yl)acetamide;

N-(3-cyclopropyl-1H-pyrazol-5-yl)-2-(2,2-difluoro-3-phenylcyclopropyl)acetamide;

N-(3-cyclopropyl-1H-pyrazol-5-yl)-2-(5-methyl-4-phenyl-3-isoxazolyl)acetamide;

N-(3-cyclopropyl-1H-pyrazol-5-yl)-2-(5-methyl-3-phenyl-4-isoxazolyl)acetamide;

2-[3-(1,3-benzodioxol-5-yl)-5-methyl-4-isoxazolyl]-N-(3-cyclopropyl-1H-pyrazol-5-yl)acetamide;

2-[4-(1,3-benzodioxol-5-yl)-5-methyl-3-isoxazolyl]-N-(3-cyclopropyl-1H-pyrazol-5-yl)acetamide;

N-(5-cyclopropyl-1H-pyrazol-3-yl)-2-(3-phenyl-2-oxiranyl)acetamide;

N-(3-cyclopropyl-1H-pyrazol-5-yl)-2-[2-(4-fluorophenyl)cyclopropyl]acetamide;

N-(3-cyclopropyl-1H-pyrazol-5-yl)-2-[2,2-difluoro-3-(3-fluorophenyl)cyclopropyl]acetamide;

N-(3-cyclopropyl-1H-pyrazol-5-yl)-2-(2-oxo-2,3-dihydro-1H-indol-5-yl)acetamide;

N-(4-{2-[(3-cyclopropyl-1H-pyrazol-5-yl)amino]-2-oxoethyl}phenyl)-1-pyrrolidinecarboxamide;

N-(4-{2-[(3-cyclopropyl-1H-pyrazol-5-yl)amino]-2-oxoethyl}phenyl)-1-piperidinecarboxamide;

N-(4-{2-[(3-cyclopropyl-1H-pyrazol-5-yl)amino]-2-oxoethyl}phenyl)-4-morpholinecarboxamide;

N-(4-{2-[(3-cyclopropyl-1H-pyrazol-5-yl)amino]-2-oxoethyl}phenyl)-4-methyl-1-piperazinecarboxamide;

N-(3-cyclopropyl-1H-pyrazol-5-yl)-2-(2-pyridinyl)acetamide;

N-(3-cyclopropyl-1H-pyrazol-5-yl)-2-(3-pyridinyl)acetamide;

N-(3-cyclopropyl-1H-pyrazol-5-yl)-2-(4-pyridinyl)acetamide;

N-(3-cyclopropyl-1H-pyrazol-5-yl)-5-(3-nitrophenyl)-2-furamide;

N-(3-cyclopropyl-1H-pyrazol-5-yl)-2-(2,5-dioxo-4-imidazolidinyl)acetamide;

N-(5-cyclopropyl-1H-pyrazol-3-yl)-2-(9-oxo-9H-fluoren-2-yl)acetamide;

N-(5-cyclopropyl-1H-pyrazol-3-yl)-2-(4'-ethyl[1,1'-biphenyl]-4-yl)acetamide;

N-(5-cyclopropyl-1H-pyrazol-3-yl)-2-(4'-propyl[1,1'-biphenyl]-4-yl)acetamide;

N-(5-cyclopropyl-1H-pyrazol-3-yl)-2-(9H-fluoren-2-yl)acetamide;

N-(5-cyclopropyl-1H-pyrazol-3-yl)-2-(9-methyl-9H-fluoren-2-yl)acetamide;

N-(5-cyclopropyl-1H-pyrazol-3-yl)-2-(2-hydroxydibenzo[b,d]furan-3-yl)acetamide;

N-(5-cyclopropyl-1H-pyrazol-3-yl)-2-(4'-hydroxy[1,1'-biphenyl]-4-yl)acetamide;

2-(4'-cyano[1,1'-biphenyl]-4-yl)-N-(5-cyclopropyl-1H-pyrazol-3-yl)acetamide;

2-(4'-bromo[1,1'-biphenyl]-4-yl)-N-(5-cyclopropyl-1H-pyrazol-3-yl)acetamide;

N-(5-cyclopropyl-1H-pyrazol-3-yl)-2-(4'-propoxy[1,1'-biphenyl]-4-yl)acetamide;

N-(5-cyclopropyl-1H-pyrazol-3-yl)-2-(4'-butoxy[1,1'-biphenyl]-4-yl)acetamide;

N-(5-cyclopropyl-1H-pyrazol-3-yl)-2-(4'-pentoxy[1,1'-biphenyl]-4-yl)acetamide;

4'-{2-[(5-cyclopropyl-1H-pyrazol-3-yl)amino]-2-oxoethyl}[1,1'-biphenyl]-4-yl acetate;

2-(4'-tert-butyl[1,1'-biphenyl]-4-yl)-N-(5-cyclopropyl-1H-pyrazol-3-yl)acetamide;

N-(5-cyclopropyl-1H-pyrazol-3-yl)-2-(3',4'-dichloro[1,1'-biphenyl]-4-yl)acetamide;

N-(5-cyclopropyl-1H-pyrazol-3-yl)-2-(3'-hydroxy[1,1'-biphenyl]-4-yl)acetamide;

2-(3'-bromo[1,1'-biphenyl]-4-yl)-N-(5-cyclopropyl-1H-pyrazol-3-yl)acetamide;

2-(3'-amino[1,1'-biphenyl]-4-yl)-N-(5-cyclopropyl-1H-pyrazol-3-yl)acetamide;

2-(4'-amino[1,1'-biphenyl]-4-yl)-N-(5-cyclopropyl-1H-pyrazol-3-yl)acetamide;

N-(5-cyclopropyl-1H-pyrazol-3-yl)-2-(3-hydroxy-2-naphthyl)acetamide;

N-(5-cyclopropyl-1H-pyrazol-3-yl)-2-(3,5-dihydroxy-2-naphthyl)acetamide;

2-(3-amino-2-naphthyl)-N-(5-cyclopropyl-1H-pyrazol-3-yl)acetamide;

N-(5-cyclopropyl-1H-pyrazol-3-yl)-2-(6-hydroxy-2-naphthyl)acetamide;

N-(5-cyclopropyl-1H-pyrazol-3-yl)-2-(2-hydroxy-1-naphthyl)acetamide;

N-(5-cyclopropyl-1H-pyrazol-3-yl)-2-(6-hydroxy-1-naphthyl)acetamide;

3-amino-N-(5-cyclopropyl-1H-pyrazol-3-yl)-4-[(2-furylmethyl)sulfonyl]-2-thiophenecarboxamide;

3-amino-4-[(4-chlorophenyl)sulfonyl]-N-(5-cyclopropyl-1H-pyrazol-3-yl)-2-thiophenecarboxamide;

3-amino-N-(5-cyclopropyl-1H-pyrazol-3-yl)-4-(phenylsulfonyl)-2-thiophenecarboxamide;

3-chloro-N-(5-cyclopropyl-1H-pyrazol-3-yl)-4-(methylsulfonyl)-2-thiophenecarboxamide;

3-amino-N-(5-cyclopropyl-1H-pyrazol-3-yl)-4-(isopropylsulfonyl)-2-thiophenecarboxamide;

3-amino-N-(5-cyclopropyl-1H-pyrazol-3-yl)-4-(propylsulfonyl)-2-thiophenecarboxamide;

3-chloro-N-(5-cyclopropyl-1H-pyrazol-3-yl)-4-(isopropylsulfonyl)-2-thiophenecarboxamide;

N-(5-cyclopropyl-1H-pyrazol-3-yl)-4-(isopropylsulfonyl)-2-thiophenecarboxamide;

4'-{2-[(5-cyclopropyl-1H-pyrazol-3-yl)amino]-2-oxoethyl}-N-[2-(1-pyrrolidinyl)ethyl][1,1'-biphenyl]-4-carboxamide;

4'-{2-[(5-cyclopropyl-1H-pyrazol-3-yl)amino]-2-oxoethyl}-N-[2-(1-pyrrolidinyl)propyl][1,1'-biphenyl]-4-carboxamide;

4'-{2-[(5-cyclopropyl-1H-pyrazol-3-yl)amino]-2-oxoethyl}-N-[2-(1-piperidinyl)ethyl][1,1'-biphenyl]-4-carboxamide;

4'-{2-[(5-cyclopropyl-1H-pyrazol-3-yl)amino]-2-oxoethyl}-N-[2-(1-piperidinyl)propyl][1,1'-biphenyl]-4-carboxamide;

4'-{2-[(5-cyclopropyl-1H-pyrazol-3-yl)amino]-2-oxoethyl}-N-[2-(4-morpholinyl)ethyl][1,1'-biphenyl]-4-carboxamide;

4'-{2-[(5-cyclopropyl-1H-pyrazol-3-yl)amino]-2-oxoethyl}-N-[2-(4-morpholinyl)propyl][1,1'-biphenyl]-4-carboxamide;

4'-{2-[(5-cyclopropyl-1H-pyrazol-3-yl)amino]-2-oxoethyl}-N-[2-(4-methyl-1-piperazinyl)ethyl][1,1'-biphenyl]-4-carboxamide;

4'-{2-[(5-cyclopropyl-1H-pyrazol-3-yl)amino]-2-oxoethyl}-N-[2-(4-methyl-1-piperazinyl)propyl][1,1'-biphenyl]-4-carboxamide;

Example 9

N-(3-cyclopropyl-1H-pyrazol-5-yl)-4-bromobenzamide 122 mg (loading 1.91 mmol/g, 0.233 mmol) of polystyrene supported N-methylmorpholine were suspended in 4 ml of chloromethane and then treated with 25.6 mg (0.117 mmol) of 4-bromobenzoyl chloride followed by 4.8 mg (0.039 mmol) of 3-cyclopropyl-5-amino-pyrazole. After 48 hours under stirring at room temperature the resin was separated by filtration and washed with 2 ml of dichloromethane. The filtrate was evaporated to dryness, the residue re-dissolved in 4 ml of dichloromethane and 100 mg of polystyrene supported trisamine were added. After 48 hours or stirring at room temperature the resin was filtered, washed with 2 ml of dichloromethane and concentrated to give, after triturating with diethylether, 9.3 mg (78% yield) of the title compound.

m.p. 190–192° C.

1H-NMR (DMSO-d6) ppm 7.91 (d, J=8.5 Hz, 2H), 7.68 (d, 2H), 6.29 (s, 1H), 1.88 (m, 1H), 0.90 (m, 2H), 0.67 (m, 2H);

MS (EI) m/z (rel. intensity) 305 (M+, 27), 185 (99), 183 (68), 157 (44), 155 (49), 77 (38), 76 (41), 66 (42), 51 (29).

Analogously the following compounds were prepared:

N-(3-cyclopropyl-1H-pyrazol-5-yl)-2-chlorobenzamide;

m.p. 155–156° C.;

1H-NMR (DMSO-d6) ppm 12.15 (s, 1H), 10.75 (s, 1H), 7.47–7.37 (m, 4H), 6.25 (s, 1H), 1.87 (m, 1H), 0.92 (m, 2H), 0.67 (m, 2H);

MS (EI) m/z (rel. intensity) 261 (M+, 6), 226 (22), 141 (23), 139 (99), 113 (19), 111 (58), 75 (42), 67 (17), 65 (38), 52 (16), 51 (24).

N-(3-cyclopropyl-1H-pyrazol-5-yl)-2-bromobenzamide;

m.p. 158–159° C.;

1H-NMR (DMSO-d6) ppm 12.15 (s, 1H), 10.75 (s, 1H), 7.65 (d, J=7.7 Hz, 1H), 7.41 (app.d., 1H), 7.35 (m, 2H), 6.26 (s, 1H), 1.86 (s, 1H), 0.92 (m, 2H), 0.68 (m, 2H);

MS (FAB) m/z (rel. intensity) 306 (MH+, 99), 613 (10), 384 (15), 382 (15), 308 (97), 307 (26), 306 (99), 305 (13), 226 (10). 185 (15), 183 (16).

N-(3-cyclopropyl-1H-pyrazol-5-yl)-3,4-dichlorobenzamide;

m.p. 196–197° C.;

H-NMR (DMSO-d6) ppm 12.20 (s, 1H), 10.90 (s, 1H), 8.21 (s, 1H), 7.94 (d, J=8.4 Hz, 1H), 7.76 (d, J=8.4 Hz, 1H), 6.29 (s, 1H), 1.87 (m, 1H), 0.92 (m, 2H), 0.67 (m, 2H);

MS (FAB) m/z (rel. intensity) 296 (MH+, 100).

N-(3-cyclopropyl-1H-pyrazol-5-yl)-2,4-dichlorobenzamide;

m.p. 148–149° C.;

$^1$H-NMR (DMSO-d6) ppm 12.15 (s, 1H), 10.82 (s, 1H), 7.68 (s, 1H), 7.49 (complex 2H), 6.25 (s, 1H), 1.87 (m, 1H), 0.92 (m, 2H), 0.67 (m, 2H);

MS (FAB) m/z (rel. intensity) 296 (MH+, 100).

N-(3-cyclopropyl-1H-pyrazol-5-yl)-1H-indole-2-carboxamide;

m.p. 268–269° C.

$^1$H-NMR (DMSO-d6) ppm 12.05 (br. s, 1H), 11.67 (s, 1H), 10.75 (s, 1H), 7.58 (d, 1H), 7.41 (m, 2H), 7.18 (t, 1H), 7.02 (t, 1H), 6.30 (s, 1H), 1.88 (m, 1H), 0.92 (m, 2H), 0.68 (m, 2H);

MS (FAB) m/z (rel. intensity) 267 (MH+, 100).

N-(3-cyclopropyl-1H-pyrazol-5-yl)-2-[5-(2,6-difluorobenzyl)-2-methoxyphenyl]acetamide;

1H-NMR (DMSO-d6) ppm 7.65 (s, 1H), 7.65 (m, 2H), 7.30 (t, 1H), 7.10 (d, 2H), 6.07 (s, 1H), 3.84 (s, 3H), 3.63 (s, 2H), 1.81 (m, 1H), 0.85 (m, 2H), 0.60 (m, 2H);

MS (FAB) m/z (rel. intensity) 412 (MH+, 99).

N-(3-cyclopropyl-1H-pyrazol-5-yl)-3,5-ditrifluoromethylbenzamide;

N-(3-cyclopropyl-1H-pyrazol-5-yl)-3,3-dimethylbutanamide;

N-(3-cyclopropyl-1H-pyrazol-5-yl)-4-iodobenzamide;

N-(3-cyclopropyl-1H-pyrazol-5-yl)-1-napthamide;

N-(3-cyclopropyl-1H-pyrazol-5-yl)-3-cyanobenzamide;

N-(3-cyclopropyl-1H-pyrazol-5-yl)-1,3-benzodioxol-5-carboxamide;

N-(3-cyclopropyl-1H-pyrazol-5-yl)-4-morpholinocarboxamide;

3-(2-chlorophenyl)-N-(3-cyclopropyl-1H-pyrazol-5-yl)-2-propenamide;

N-(3-cyclopropyl-1H-pyrazol-5-yl)-2-(propylsulfanyl)nicotinamide;

N-(3-cyclopropyl-1H-pyrazol-5-yl)-2,2,5,7-tetramethyl-1-1-oxo-4-indanecarboxamide;

N-(3-cyclopropyl-1H-pyrazol-5-yl)-2-pyridinecarboxamide;

N-(3-cyclopropyl-1H-pyrazol-5-yl)-2-adamantanecarboxamide;

N-(3-cyclopropyl-1H-pyrazol-5-yl)-4-methylbenzamide;

N-(3-cyclopropyl-1H-pyrazol-5-yl)-2,6-dichlorobenzamide;

N-(3-cyclopropyl-1H-pyrazol-5-yl)-2-methoxybenzamide;

N-(3-cyclopropyl-1H-pyrazol-5-yl)-2-methylbenzamide;

N-(3-cyclopropyl-1H-pyrazol-5-yl)-3-fluorobenzamide;

N-(3-cyclopropyl-1H-pyrazol-5-yl)-3-chlorobenzamide;

N-(3-cyclopropyl-1H-pyrazol-5-yl)-3,5-dimethoxybenzamide;

N-(3-cyclopropyl-1H-pyrazol-5-yl)-3-methylbenzamide;

N-(3-cyclopropyl-1H-pyrazol-5-yl)-4-fluorobenzamide;

N-(3-cyclopropyl-1H-pyrazol-5-yl)-4-trifluoromethylbenzamide;

Methyl 4-[(3-cyclopropyl-1H-pyrazol-5-yl)amino]-4-oxobutanoate;

N-(3-cyclopropyl-1H-pyrazol-5-yl)-cyclopropanecarboxamide;

N-(3-cyclopropyl-1H-pyrazol-5-yl)-4-cyanobenzamide;

N-(3-cyclopropyl-1H-pyrazol-5-yl)-2-naphthamide;

N-(3-cyclopropyl-1H-pyrazol-5-yl)-2-thiophenecarboxamide;

N-(3-cyclopropyl-1H-pyrazol-5-yl)-2-quinoxalinecarboxamide;

N-(3-cyclopropyl-1H-pyrazol-5-yl)-3,4-difluorobenzamide;

N-(3-cyclopropyl-1H-pyrazol-5-yl)-3,5-difluorobenzamide;

N-(3-cyclopropyl-1H-pyrazol-5-yl)-2-(2,5-dimethoxyphenyl)acetamide;

2-(4-chlorophenoxy)-N-(3-cyclopropyl-1H-pyrazol-5-yl)nicotinamide;

3-chloro-N-(3-cyclopropyl-1H-pyrazol-5-yl)-2-thiophenecarboxamide;

2,5-dichloro-N-(3-cyclopropyl-1H-pyrazol-5-yl)-3-thiophenecarboxamide;

N-(3-cyclopropyl-1H-pyrazol-5-yl)-2-ethoxybenzamide;

N-(3-cyclopropyl-1H-pyrazol-5-yl)-2-phenylbutanamide;

N-(3-cyclopropyl-1H-pyrazol-5-yl)-4-trifluoromethoxybenzamide;

3-chloro-N-(3-cyclopropyl-1H-pyrazol-5-yl)-benzo[b]thiophene-2-carboxamide.

All compounds were characterized by mass spectrometry (MS). LC-MS confirmed that in each case the principle component had a molecular ion corresponding to the expected product. The compounds showed an HPLC area % ranging from 70 to 100.

HPLC analysis:
Solvent A: H2O/CH3CN=90/10+0.1% TFA
Solvent B: H2O/CH3CN=10/90+0.075% TFA

| Time (min) | % A | % B |
|---|---|---|
| 0 | 0 | 100 |
| 6.5 | 0 | 100 |
| 7 | 100 | 0 |
| 10 | 100 | 0 |

Rate: 1.5 ml/min

Detection: UV 254 nm

Temperature: room temperature

Column: Supelco™, Discovery RP Amide C16, 5·m, (50× 4.6) mm

Example 10

N-(3-cyclopropyl-1H-pyrazol-5-yl)-1H-pyrrole-2-carboxamide

To a solution of 5-amino-3-cyclopropylpyrazole (274 mg, 2.2 mmol) in 6 mL of acetonitrile was added a solution of 2-trichloroacetylpyrrole (430 mg, 2.0 mmol) in 6 mL of acetonitrile, followed by 250 μL of triethylamine. The mixture was stirred and heated at reflux, under nitrogen, for 8 hours. The mixture was poured into ethyl acetate and 1 M $KH_2PO_4$. The organic phase was dried over $Na_2SO_4$, concentrated, and the residue taken up in ether. White needles precipitated from ether, whose NMR spectrum revealed a one-to-one complex of the product and ether. The solid was heated to 62° C. under vacuum overnight to afford 190 mg (0.41 mmol, 44%) of ether-free product, m.p. 220–221° C., $^1$H NMR (DMSO-$d_6$) δ 12.1 (s, 1H), 11.5 (s, 1H), 10.2 (s, 1H), 7.06 (s, 1H), 6.89 (s, 1H), 6.24 (s, 1H), 6.08 (s, 1H), 1.86 (m, 1H), 0.89 (m, 2H), 0.66 (m, 2H); IR (drift) 3263 (b), 3174 (b), 2351 (w), 2328 (w), 1906 (w), 1645 (s), 1639 (s), 1587 (s), 1554, 1538, 1488, 1439, 1402, 1319, 786, cm$^{-1}$ Anal. Calcd for $C_{11}H_{12}N_4O$: C, 61.10; H, 5.59; N, 25.91. Found: C, 60.99; H, 5.63; N, 25.68.

Following the same method but employing 5-amino-3-cyclobutylpyrazole, N-(3-cyclobutyl-1H-pyrazol-5-yl)-1H-pyrrole-2-carboxamide, was prepared.

To 260 mg (1.9 mmol) of 5-amino-3-cyclobutylpyrazole in 7 mL of acetonitrile was added 407 mg (1.9 mmol) of 2-trichloroacetylpyrrole and 220 μL of triethylamine. The mixture was stirred and heated at reflux, under nitrogen, for 12 hours. TLC analysis showed some starting material still remained. The mixture was concentrated and chromatographed over silica gel, eluting with 5% methanol in chloroform. The fractions containing the product were concentrated to an oil, which crystallized upon concentration from ether and methanol, to afford 200 mg (0.87 mmol, 46%) of a beige solid, m.p. 207–209° C., $^1$H NMR (DMSO-$d_6$) δ 12.1 (s, 1H), 11.5 (s, 1H), 10.2 (s, 1H), 7.08 (s, 1H), 6.89 (s, 1H), 6.41 (s, 1H), 6.09 (s, 1H), 3.46 (m, 1H), 2.24 (m, 2H), 2.11 (m, 2H), 2.0–1.8 (m, 2H); IR (drift) 3329, 3294, 3257, 3225 (b), 2460 (w), 2351 (w), 2318 (w), 2257 (w), 1643 (s), 1588 (s), 1541, 1487 (s), 1416, 757, 747, cm$^{-1}$ Anal. Calcd for $C_{12}H_{14}N_4O$: C, 62.59; H, 6.13; N, 24.33. Found: C, 62.37; H, 6.22; N, 24.13.

Analogously the following compounds were prepared:

N-(5-cyclopropyl-1H-pyrazol-3-yl)-4-(3-methylbenzoyl)-1H-pyrrole-2-carboxamide;

1H-NMR (DMSO-d6) ppm 12.3 (s, 1H), 12.1 (s, 1H), 10.5 (s, 1H), 7.58 (m, 3H), 7.45 (m, 1H), 7.42 (m, 2H), 6.27 (s, 1H), 2.39 (s, 3H), 1.88 (d, J=7.0 Hz, 1H), 0.92 (m, 2H), 0.69 (m, 2H);

N-(5-cyclopropyl-1H-pyrazol-3-yl)-4-(3-fluorobenzoyl)-1H-pyrrole-2-carboxamide;

1H-NMR (DMSO-d6) ppm 7.67 (m, 1H), 7.58 (m, 3H), 7.49 (s, 1), 7.39 (dt, J=7.2 Hz, 1H), 6.25 (br s, 1H), 1.92 (m, 1H), 1.00 (m, 2H), 0.76 (m, 2H);

N-(5-cyclopropyl-1H-pyrazol-3-yl)-4-(2-fluorobenzoyl)-1H-pyrrole-2-carboxamide;

1H-NMR (DMSO-d6) ppm 7.58 (m, 2H), 7.48 (s, 1), 7.42 (s, 1H), 7.30 (m, 2H), 6.18 (s, 1H), 1.92 (m, 1H), 0.98 (m, 2H), 0.74 (m, 2H).

N-(5-cyclopropyl-1H-pyrazol-3-yl)-4-(3,3-dimethylbutanoyl)-1H-pyrrole-2-carboxamide;

N-(5-cyclopropyl-1H-pyrazol-3-yl)-4-(cyclopropylcarbonyl)-1H-pyrrole-2-carboxamide;

N-(5-cyclopropyl-1H-pyrazol-3-yl)-4-(2-thienylcarbonyl)-1H-pyrrole-2-carboxamide;

N-(5-cyclopropyl-1H-pyrazol-3-yl)-4-(2-methylbenzoyl)-1H-pyrrole-2-carboxamide;

4-(1-benzothien-2-ylcarbonyl)-N-(5-cyclopropyl-1H-pyrazol-3-yl)-1H-pyrrole-2-carboxamide;

N-(5-cyclopropyl-1H-pyrazol-3-yl)-4-(3-methylbutanoyl)-1H-pyrrole-2-carboxamide;

4-cyclopentylcarbonyl)-N-(5-cyclopropyl-1H-pyrazol-3-yl)-1H-pyrrolle-2-carboxamide;

N-(5-cyclopropyl-1H-pyrazol-3-yl)-4-pentanoyl-1H-pyrrole-2-carboxamide;

4-(3-chlorobenzoyl)-N-(5-cyclopropyl-1H-pyrazol-3-yl)-1H-pyrrole-2-carboxamide;

N-(5-cyclopropyl-1H-pyrazol-3-yl)-4-(phenylacetyl)-1H-pyrrole-2-carboxamide;

N-(5-cyclopropyl-1H-pyrazol-3-yl)-4-[(4-fluorophenyl)acetyl]-1H-pyrrole-2-carboxamide;

4-butyryl-N-(5-cyclopropyl-1H-pyrazol-3-yl)-1H-pyrrole-2-carboxamide;

N-(5-cyclopropyl-1H-pyrazol-3-yl)-4-(4-fluorobenzoyl)-1H-pyrrole-2-carboxamide;

N-(3-cyclopropyl-1H-pyrazol-5-yl)-4-(3,4-dimethylbenzoyl)-1H-pyrrole-2-carboxamide;

N-(3-cyclopropyl-1H-pyrazol-5-yl)-4-(4-fluorobenzoyl)-1H-pyrrole-2-carboxamide;

N-(3-cyclopropyl-1H-pyrazol-5-yl)-4-(4-methylbenzoyl)-1H-pyrrole-2-carboxamide;

4-(4-chlorobenzoyl)-N-(3-cyclopropyl-1H-pyrazol-5-yl)-1H-pyrrole-2-carboxamide;

4-(cyclohexylcarbonyl)-N-(3-cyclopropyl-1H-pyrazol-5-yl)-1H-pyrrole-2-carboxamide;

methyl 5-(5-{[(3-cyclopropyl-1H-pyrazol-5-yl)amino]carbonyl}-1H-pyrrol-3-yl)-5-oxopentanoate 4-acetyl-N-(3-cyclopropyl-1H-pyrazol-5-yl)-1H-pyrrole-2-carboxamide;

N-(3-cyclopropyl-1H-pyrazol-5-yl)-4-(2,6-dimethoxybenzoyl)-1H-pyrrole-2-carboxamide;

N-(3-cyclopropyl-1H-pyrazol-5-yl)-1-methyl-1H-pyrrole-2-carboxamide;

4-bromo-N-(3-cyclopropyl-1H-pyrazol-5-yl)-1H-pyrrole-2-carboxamide;

N-(3-cyclopropyl-1H-pyrazol-5-yl)-1-methyl-4-(3-methylbenzoyl)-1H-pyrrole-2-carboxamide;

N-(3-cyclopropyl-1H-pyrazol-5-yl)-2-quinoxalinecarboxamide;

(1R,2R)-N-(3-cyclopropyl-1H-pyrazol-5-yl)-2-phenylcyclopropanecarboxamide;

N-(3-cyclopropyl-1H-pyrazol-5-yl)-2-phenylcyclopropanecarboxamide;

3-chloro-N-(3-cyclopropyl-1H-pyrazol-5-yl)-2-thiophenecarboxamide;

4-benzoyl-N-(3-cyclopropyl-1H-pyrazol-5-yl)benzamide;

Example 11

2-[1,1'-biphenyl]-4-yl-N-(3-cyclopropyl-1H-pyrazol-5-yl)acetamide

To 5.1 g of trityl chloride resin (Novabiochem, loading 1.2 mmol/g) swelled in 76 ml of DCM and 14 ml of DMF, 3.98 g of 2-(4-bromophenyl)-N-(5-cyclopropyl-1H-pyrazol-3-yl)acetamide and 3 ml of DIPEA were added. The mixture was shaken 18 hrs at room temperature and then washed with DMF (3×50 ml), MeOH (3×50 ml) and DCM (3×50 ml). Unreacted trityl chloride resin was capped adding 50 ml of DIPEA:MeOH:DCM (1:2:17), the mixture was shaken 1 hr and then washed with DMF (3×50 ml), MeOH (3×50 ml) and DCM (3×50 ml). The resin was dried under high vacuum. Loading found 1.1 mmol/g (HPLC calibration curve).

To 40 mg of 2-(4-bromophenyl)-N-(5-cyclopropyl-1H-pyrazol-3-yl)acetamide resin linked 1 ml of a 10.4M solution of CsF in DME:MeOH (3:1), phenylboronic acid (0, 12 mmol) in DME (0.5 ml) and tetrakis triphenylphosphine palladium, (Pd(PPh$_3$)$_4$, 0.008 mmol) in DME (1 ml) were added. The mixture was shaken 18 hrs at 80° C. and then washed with DMF (3×5 ml), MeOH (3×5 ml) and DCM (3×5 ml). To the resin 5 ml of TFA 10% in DCM were added and the mixture was shaken 1 hr at room temperature, the organic phase was filtered off and the resin was washed with DCM (3×5 ml) and DMSO (2×5 ml). The organic fractions were collected and evaporated under reduced pressure and the residue was analyzed by HPLC-MS (area count 90%, 254 nm; M+1=318, 2M+1=365) without further purification.

1H-NMR (400 MHz, DMSO-d6) ppm 10.49 (s, 1H, NHCO), 7.6–7.3 (m, 9H, biphenyl), 6.09 (s, 1H, CH-pyrazole), 3.59 (s, 2H, COCH2), 1.82 (m, 1H, cyclopropyl-CH);

ESI (+) MS: m/z 318 (100, MH+);

N-(5-cyclopropyl-1H-pyrazol-3-yl)-2-(3'-ethoxy-[1,1'-biphenyl]-4-yl)acetamide

1H-NMR (400 MHz, DMSO-d6) ppm 10.48 (s, 1H, NHCO), 7.4–7.3 (m, 3H, o,m-Ph), 6.09 (s, 1H, CH-pyrazole), 4.03 (q, J=7 Hz, 2H, OCH2), 3.58 (s, 2H, COCH2), 1.82 (m, 1H, cyclopropyl-CH);

ESI (+) MS: m/z 362 (100, MH+);

N-(5-cyclopropyl-1H-pyrazol-3-yl)-2-(3'-acetamido-[1,1'-biphenyl]-4-yl)acetamide 1H-NMR (400 MHz, DMSO-d6) ppm 10.49 (s, 1H, NHCO), 7.8–7.2 (m, 8H, biphenyl), 6.09 (s, 1H, CH-pyrazole), 2.04 (s, 3H, COCH3), 1.82 (m, 1H, cyclopropyl-CH);

ESI (+) MS: m/z 375 (100, MH+);

N-(5-cyclopropyl-1H-pyrazol-3-yl)-2-(4'-tert-butyl-[1,1'-biphenyl]-4-yl)acetamide 1H-NMR (400 MHz, DMSO-d6) ppm 10.49 (s, 1H, NHCO), 7.6–7.3 (m, 8H, biphenyl), 6.09 (s, 1H, CH-pyrazole), 3.55 (s, 2H, COCH2), 1.29 (s, 9H, terbutyl), 1.82 (m, 1H, cyclopropyl-CH);

N-(5-cyclopropyl-1H-pyrazol-3-yl)-2-(3'-trifluoromethoxy)[1,1'-biphenyl]-4-yl)acetamide 1H-NMR (400 MHz, DMSO-d6) ppm 10.49 (s, 1H, NHCO), 7.7–7.3 (m, 8H, biphenyl), 6.09 (s, 1H, CH-pyrazole), 3.61 (s, 2H, COCH2), 1.82 (m, 1H, cyclopropyl-CH);

N-(5-cyclopropyl-1H-pyrazol-3-yl)-2-(2',3'-dimethyl-[1,1'-biphenyl]-4-yl)acetamide 1H-NMR (400 MHz, DMSO-d6) ppm 10.50 (s, 1H, NHCO), 7.4–6.9 (m, 7H, biphenyl), 6.10 (s, 1H, CH-pyrazole), 2.32 (s, 3H, CH3), 2.10 (s, 3H, CH3), 1.82 (m, 1H, cyclopropyl-CH);

N-(5-cyclopropyl-1H-pyrazol-3-yl)-2-(2',4'-dimethoxy-[1,1'-biphenyl]-4-yl)acetamide 1H-NMR (400 MHz, DMSO-d6) ppm 10.47 (s, 1H, NHCO), 7.65 (d, J=8 Hz, 2H, m-Ph), 7.16 (d, J=8.3 Hz, 1H, o-Ph) 6.09 (s, 1H, CH-pyrazole), 3.55 (s, 2H, COCH2), 1.82 (m, 1H, cyclopropyl-CH);

N-(5-cyclopropyl-1H-pyrazol-3-yl)-2-(3',5'-difluoro-[1,1'-biphenyl]-4-yl)acetamide 1H-NMR (400 MHz, DMSO-d6) ppm 10.49 (s, 1H, NHCO), 7.65 (d, J=8.3 Hz, 2H, m-Ph), 7.15 (m, 1H, p-Ph) 6.09 (s, 1H, CH-pyrazole), 3.60 (s, 2H, COCH2), 1.82 (m, 1H, cyclopropyl-CH);

N-(5-cyclopropyl-1H-pyrazol-3-yl)-2-(2'-ethoxy-[1,1'-biphenyl]-4-yl)acetamide

1H-NMR (400 MHz, DMSO-d6) ppm 10.48 (s, 1H, NHCO), 7.4–7.0 (m, 8H, biphenyl), 6.10 (s, 1H, CH-pyrazole), 4.03 (q, J=7 Hz, 2H, OCH2), 3.58 (s, 2H, COCH2), 1.82 (m, 1H, cyclopropyl-CH);

N-(5-cyclopropyl-1H-pyrazol-3-yl)-2-(3',4'-dimethoxy-[1,1'-biphenyl]-4-yl)acetamide 1H-NMR (400 MHz, DMSO-d6) ppm 10.46 (s, 1H, NHCO), 7.55 (d, J=8.3 Hz, 2H, m-Ph), 7.00 (d, J=8.4 Hz, 1H, m'-Ph) 6.08 (s, 1H, CH-pyrazole), 3.8–3.7 (2×s, 6H, 2×OCH3), 1.82 (m, 1H, cyclopropyl-CH);

N-(5-cyclopropyl-1H-pyrazol-3-yl)-2-(4'-ethyl-[1,1'-biphenyl]-4-yl)acetamide

1H-NMR (400 MHz, DMSO-d6) ppm 10.47 (s, 1H, NHCO), 7.6–7.2 (m, 8H, biphenyl), 6.09 (s, 1H, CH-pyrazole), 3.58 (s, 2H, COCH2), 2.61 (q, J=7 Hz, 2H, CH2CH3), 1.82 (m, 1H, cyclopropyl-CH);

N-(5-cyclopropyl-1H-pyrazol-3-yl)-2-(3'-chloro-4'-fluoro-[1,1'-biphenyl]-4-yl)acetamide 1H-NMR (400 MHz, DMSO-d6) ppm 10.48 (s, 1H, NHCO), 7.8–7.4 (m, 7H, biphenyl), 6.08 (s, 1H, CH-pyrazole), 1.82 (m, 1H, cyclopropyl-CH);

N-(5-cyclopropyl-1H-pyrazol-3-yl)-2-((4'-methylthio)-[1,1'-biphenyl]-4-yl)acetamide 1H-NMR (400 MHz, DMSO-d6) ppm 10.48 (s, 1H, NHCO), 7.56 (d, J=8.3 Hz, 2H, m-Ph), 6.96 (d, J=6.6 Hz, 2H, m'-Ph) 6.09 (s, 1H, CH-pyrazole), 3.59 (s, 3H, SCH3), 1.82 (m, 1H, cyclopropyl-CH);

N-(5-cyclopropyl-1H-pyrazol-3-yl)-2-(4'-ethoxy-[1,1'-biphenyl]-4-yl)acetamide

1H-NMR (400 MHz, DMSO-d6) ppm 10.50 (s, 1H, NHCO), 7.52 (d, J=8.3 Hz, 2H, m-Ph), 6.96 (d, J=6.7 Hz, 2H, m'-Ph) 6.09 (s, 1H, CH-pyrazole), 4.03 (q, J=7 Hz, 2H, OCH2CH3), 1.82 (m, 1H, cyclopropyl-CH);

N-(5-cyclopropyl-1H-pyrazol-3-yl)-2-(4'-acetyl-[1,1'-biphenyl]-4-yl)acetamide

1H-NMR (400 MHz, DMSO-d6) ppm 10.50 (s, 1H, NHCO), 8.00 (d, J=8.6 Hz, 2H, m'-Ph), 6.96 (d, J=8.3 Hz, 2H, m-Ph) 6.09 (s, 1H, CH-pyrazole), 2.59 (s, 3H, COCH3), 1.82 (m, 1H, cyclopropyl-CH);

N-(5-cyclopropyl-1H-pyrazol-3-yl)-2-(2',5'-dimethoxy[1,1'-biphenyl]-4-yl)acetamide 1H-NMR (400 MHz, DMSO-d6) ppm 10.48 (s, 1H, NHCO), 7.38 (d, J=8.3 Hz, 2H, m-Ph), 6.81 (d, J=3.1 Hz, 1H, o'-Ph) 6.10 (s, 1H, CH-pyrazole), 3.55 (s, 2H, COCH2), 1.82 (m, 1H, cyclopropyl-CH);

N-(5-cyclopropyl-1H-pyrazol-3-yl)-2-(2'-fluoro[1,1'-biphenyl]-4-yl)acetamide

1H-NMR (400 MHz, DMSO-d6) ppm 10.51 (s, 1H, NHCO), 7.5–7.3 (m, 8H, biphenyl), 6.10 (s, 1H, CH-pyrazole), 3.62 (s, 2H, COCH2), 1.82 (m, 1H, cyclopropyl-CH);

N-(5-cyclopropyl-1H-pyrazol-3-yl)-2-(3'-fluoro[1,1'-biphenyl]-4-yl)acetamide

1H-NMR (400 MHz, DMSO-d6) ppm 10.49 (s, 1H, NHCO), 7.63 (d, J=8.2 Hz, 2H, m-Ph), 7.38 (d, J=8.2 Hz, 2H, o-Ph) 6.09 (s, 1H, CH-pyrazole), 3.59 (s, 2H, COCH2), 1.82 (m, 1H, cyclopropyl-CH);

N-(5-cyclopropyl-1H-pyrazol-3-yl)-2-(3'-methoxy[1,1'-biphenyl]-4-yl)acetamide

1H-NMR (400 MHz, DMSO-d6) ppm 10.48 (s, 1H, NHCO), 7.57 (d, J=8.0 Hz, 2H, m-Ph), 6.09 (s, 1H, CH-pyrazole), 3.79 (s, 3H, OCH3), 3.59 (s, 2H, COCH2), 1.82 (m, 1H, cyclopropyl-CH);

N-(5-cyclopropyl-1H-pyrazol-3-yl)-2-(3'-formyl-4'-methoxy[1,1'-biphenyl]-4-yl)acetamide 1H-NMR (400 MHz, DMSO-d6) ppm 10.49 (s, 1H, NHCO), 8.0–7.9 (m, 2H, o'-Ph), 7.60 (d, J=8.3 Hz, 2H, m-Ph) 6.09 (s, 1H, CH-pyrazole), 3.60 (s, 2H, COCH2), 1.82 (m, 1H, cyclopropyl-CH);

N-(5-cyclopropyl-1H-pyrazol-3-yl)-2-(4'-fluoro-3'-methyl[1,1'-biphenyl]-4-yl)acetamide 1H-NMR (400 MHz, DMSO-d6) ppm 10.47 (s, 1H, NHCO), 7.55 (d, J=8.3 Hz, 2H, m-Ph), 6.09 (s, 1H, CH-pyrazole), 3.59 (s, 2H, COCH2), 2.28 (s, 3H, CH3), 1.82 (m, 1H, cyclopropyl-CH);

N-(5-cyclopropyl-1H-pyrazol-3-yl)-2-(5'-fluoro-2'-methoxy[1,1'-biphenyl]-4-yl)acetamide 1H-NMR (400 MHz, DMSO-d6) ppm 10.48 (s, 1H, NHCO), 7.8–7.7 (m, 3H, m,m'-Ph), 6.09 (s, 1H, CH-pyrazole), 3.63 (s, 2H, COCH2), 1.82 (m, 1H, cyclopropyl-CH);

N-(5-cyclopropyl-1H-pyrazol-3-yl)-2-(4'-methoxy[1,1'-biphenyl]-4-yl)acetamide

1H-NMR (400 MHz, DMSO-d6) ppm 10.46 (s, 1H, NHCO), 7.52 (d, J=8.3 Hz, 2H, m-Ph), 6.99 (d, J=8.9 Hz, 2H, m'-Ph), 6.09 (s, 1H, CH-pyrazole), 3.62 (s, 2H, COCH2), 1.82 (m, 1H, cyclopropyl-CH);

N-(5-cyclopropyl-1H-pyrazol-3-yl)-2-(2',5'-dimethyl[1,1'-biphenyl]-4-yl)acetamide 1H-NMR (400 MHz, DMSO-d6) ppm 10.50 (s, 1H, NHCO), 7.34 (d, J=8.2 Hz, 2H, m-Ph), 7.13 (d, J=7.8 Hz, 2H, m'-Ph) 6.11 (s, 1H, CH-pyrazole), 3.60 (s, 2H, COCH2), 1.82 (m, 1H, cyclopropyl-CH);

N-(5-cyclopropyl-1H-pyrazol-3-yl)-2-(2',5'-difluoro[1,1'-biphenyl]-4-yl)acetamide 1H-NMR (400 MHz, DMSO-d6) ppm 10.49 (s, 1H, NHCO), 7.5–7.2 (m, 7H, biphenyl), 6.09 (s, 1H, CH-pyrazole), 3.62 (s, 2H, COCH2), 1.82 (m, 1H, cyclopropyl-CH);

Analogously, the following compounds were prepared:

N-(5-cyclopropyl-1H-pyrazol-3-yl)-2-(pentafluoro[1,1'-biphenyl]-4-yl)acetamide

N-(5-cyclopropyl-1H-pyrazol-3-yl)-2-(4'-carboxy[1,1'-biphenyl]-4-yl)acetamide

N-(5-cyclopropyl-1H-pyrazol-3-yl)-2-(2',5'-dichloro[1,1'-biphenyl]-4-yl)acetamide N-(5-cyclopropyl-1H-pyrazol-3-yl)-2-(4'-formyl[1,1'-biphenyl]-4-yl)acetamide N-(5-cyclopropyl-1H-pyrazol-3-yl)-2-(2',6-difluoro[1,1'-biphenyl]-4-yl)acetamide N-(5-cyclopropyl-1H-pyrazol-3-yl)-2-(2',6-dimethyl[1,1'-biphenyl]-4-yl)acetamide N-(5-cyclopropyl-1H-pyrazol-3-yl)-2-(2',6-dimethoxy[1,1'-biphenyl]-4-yl)acetamide N-(5-cyclopropyl-1H-pyrazol-3-yl)-2-(2'-acetyl-[1,1'-biphenyl]-4-yl)acetamide N-(5-cyclopropyl-1H-pyrazol-3-yl)-2-(3',4'-difluoro-[1,1'-biphenyl]-4-yl)acetamide N-(5-cyclopropyl-1H-pyrazol-3-yl)-2-(3'-(hydroxymethyl)[1,1'-biphenyl]-4-yl)acetamide N-(5-cyclopropyl-1H-pyrazol-3-yl)-2-(3'-nitro-[1,1'-biphenyl]-4-yl)acetamide N-(5-cyclopropyl-1H-pyrazol-3-yl)-2-(2'-chloro-[1,1'-biphenyl]-4-yl)acetamide

Example 12

N-(5-cyclopropyl-1H-pyrazol-3-yl)-2-[4-(3-thienyl)phenyl] acetamide 330 mg (2.17 mmol) of CsF, 81 mg (0.63 mmol) of thienylboronic acid and 36 mg (0.031 mmol) of tetrakis triphenylphosphine palladium (Pd(PPh$_3$)$_4$) were added to 100 mg (0.31 mmol) of 2-(4-bromophenyl)-N-(5-cyclopropyl-1H-pyrazol-3-yl)acetamide) in 25 mL of DME and 2 mL of MeOH. The mixture was shaken 48 hrs at 80° C. under nitrogen. The reaction mixture is evaporated, redissolved in ethyl acetate and then washed with a saturated solution of NaHCO3. The organic layer was, after treatment with anhydrous sodium sulfate, evaporated under reduced pressure and the title compound was obtained by crystallization from acetone (48 mg, 48% yield).

1H-NMR (400 MHz, DMSO-d6) ppm 10.42 (s, 1H, NHCO), 7.79 (dd, J=3—1.4 Hz, 1H, CCHS), 6.11 (s, 1H, CH-pyrazole), 3.56 (s, 2H, COCH2), 1.82 (m, 1H, cyclopropyl-CH);

ESI (+) MS: m/z 324 (100, MH+);

Analogously, the following compounds were prepared:

N-(5-cyclopropyl-1H-pyrazol-3-yl)-2-(4'-fluoro[1,1'-biphenyl]-4-yl)acetamide;

1H-NMR (400 MHz, DMSO-d6) ppm 10.44 (s, 1H, NHCO), 6.11 (s, 1H, CH-pyrazole), 3.59 (s, 2H, COCH2); 1.81 (m, 1H, cyclopropyl-CH);

ESI (+) MS: m/z 336 (100, MH+);

2-(3'-acetyl[1,1'-biphenyl]-4-yl)-N-(3-cyclopropyl-1H-pyrazol-5-yl)acetamide

1H-NMR (400 MHz, DMSO-d6) ppm 10.49 (s, 1H, NHCO), 7.66 (d, J=8 Hz, 2H, m-Ph), 7.59 (t, J=7.8 Hz, 1H, m'-Ph), 6.10 (s, 1H, CH-pyrazole), 3.62 (s, 2H, COCH2), 2.63 (s, 3H, COCH3), 1.82 (m, 1H, cyclopropyl-CH);

ESI (+) MS: m/z 360 (100, MH+);

N-(5-cyclopropyl-1H-pyrazol-3-yl)-2-(4'-trifluoromethoxy [1,1'-biphenyl]-4-yl)acetamide;

1H-NMR (400 MHz, DMSO-d6) ppm 10.51 (s, 1H, NHCO), 7.74 (d, J=6.5 Hz, 2H, o'-Ph), 7.60 (d, J=7.3 Hz, 2H, m-Ph), 6.09 (s, 1H, CH-pyrazole), 3.61 (s, 2H, COCH2); 1.82 (m, 1H, cyclopropyl-CH);

ESI (+) MS: m/z 402 (100, MH+);

4'-{2-[(5-cyclopropyl-1H-pyrazol-3-yl)amino]-2-oxethyl} [1,1'-biphenyl]-4-carboxylic acid 1H-NMR (400 MHz, DMSO-d6) ppm 10.46 (s, 1H, NHCO), 6.09 (s, 1H, CH-pyrazole), 3.61 (s, 2H, COCH2); 1.81 (m, 1H, cyclopropyl-CH);

ESI (+) MS: m/z 362 (100, MH+);

N-(5-cyclopropyl-1H-pyrazol-3-yl)-2-(4'-formyl[1,1'-biphenyl]-4-yl)acetamide;

1H-NMR (400 MHz, DMSO-d6) ppm 10.47 (s, 1H, NHCO), 10.02 (s, 1H, CHO), 6.11 (s, 1H, CH-pyrazole), 3.62 (s, 2H, COCH2); 1.81 (m, 1H, cyclopropyl-CH);

ESI (+) MS: m/z 346 (100, MH+);

4'-{2-[(5-cyclopropyl-1H-pyrazol-3-yl)amino]-2-oxethyl} [1,1'-biphenyl]-4-carboxamide;

1H-NMR (400 MHz, DMSO-d6) ppm 10.46 (s, 1H, NHCO), 6.09 (s, 1H, CH-pyrazole), 3.61 (s, 2H, COCH2); 1.81 (m, 1H, cyclopropyl-CH);

ESI (+) MS: m/z 361 (100, MH+);

N-(5-cyclopropyl-1H-pyrazol-3-yl)-2-(4'-(hydroxymethyl) [1,1'-biphenyl]-4-yl)acetamide;

1H-NMR (400 MHz, DMSO-d6) ppm 7.7–7.4 (m, 8H, biphenyl), 6.10 (s, 1H, CH-pyrazole), 3.60 (s, 2H, COCH2); 1.81 (m, 1H, cyclopropyl-CH);

ESI (+) MS: m/z 348 (100, MH+);

N-(5-cyclopropyl-1H-pyrazol-3-yl)-2-[4-(2-thienyl)phenyl] acetamide;

1H-NMR (400 MHz, DMSO-d6) ppm 10.47 (s, 1H, NHCO), 7.6–7.1 (m, 7H, aromatic), 6.08 (s, 1H, CH-pyrazole), 1.82 (m, 1H, cyclopropyl-CH);

ESI (+) MS: m/z 324 (100, MH+);

N-(5-cyclopropyl-1H-pyrazol-3-yl)-2-[4-(5-methyl-2-thienyl)phenyl]acetamide;

1H-NMR (400 MHz, DMSO-d6) ppm 10.46 (s, 1H, NHCO), 7.48 (d, J=8.3 Hz, 2H, m-Ph), 3.55 (s, 2H, COCH2), 2.43 (s, 3H, CH3), 6.09 (s, 1H, CH-pyrazole), 1.82 (m, 1H, cyclopropyl-CH);

N-(5-cyclopropyl-1H-pyrazol-3-yl)-2-[4-naphthyl)phenyl] acetamide;

1H-NMR (400 MHz, DMSO-d6) ppm 10.50 (s, 1H, NHCO), 8.2–7.4 (m, 11H, aromatic), 6.10 (s, 1H, CH-pyrazole), 3.55 (s, 2H, COCH2), 1.82 (m, 1H, cyclopropyl-CH);

2-[4-(1,3-benzodioxol-5-yl)phenyl]-N-(5-cyclopropyl-1H-pyrazol-3-yl)acetamide;

1H-NMR (400 MHz, DMSO-d6) ppm 10.48 (s, 1H, NHCO), 7.50 (d, J=8.3 Hz, 2H, m-Ph), 6.96 (d, J=8.1 Hz, 1H, m'-Ph), 6.09 (s, 1H, CH-pyrazole), 6.02 (s, 2H, OCH2O), 1.82 (m, 1H, cyclopropyl-CH);

2-[4-(1-benzofuran-2-yl)phenyl]-N-(5-cyclopropyl-1H-pyrazol-3-yl)acetamide

1H-NMR (400 MHz, DMSO-d6) ppm 10.51 (s, 1H, NHCO), 7.8–7.2 (m, 9H, aromatic), 6.09 (s, 1H, CH-pyrazole), 1.82 (m, 1H, cyclopropyl-CH);

2-[4-(1-benzothien-2-yl)phenyl]-N-(5-cyclopropyl-1H-pyrazol-3-yl)acetamide;

1H-NMR (400 MHz, DMSO-d6) ppm 10.49 (s, 1H, NHCO), 7.70 (d, J=8.3 Hz, 2H, m-Ph), 6.10 (s, 1H, CH-pyrazole), 3.62 (s, 2H, COCH2), 1.82 (m, 1H, cyclopropyl-CH);

N-(5-cyclopropyl-1H-pyrazol-3-yl)-2-[4-(1-naphthyl)phenyl]acetamide;

N-(5-cyclopropyl-1H-pyrazol-3-yl)-2-[4-(2-furyl)phenyl] acetamide;

2-[4-(5-acetyl-2-thienyl)phenyl]-N-(5-cyclopropyl-1H-pyrazol-3-yl)acetamide;

2-[4-(5-chloro-2-thienyl)phenyl]-N-(5-cyclopropyl-1H-pyrazol-3-yl)acetamide;

N-(5-cyclopropyl-1H-pyrazol-3-yl)-2-[3'-({[5-(dimethylamino)-1-naphthyl]sulfonyl}amino)[1,1'-biphenyl]-4-yl) acetamide;

N-(5-cyclopropyl-1H-pyrazol-3-yl)-2-[4-(3-formyl-2-thienyl)phenyl]acetamide;

N-(5-cyclopropyl-1H-pyrazol-3-yl)-2-[4-(3-formyl-2-thienyl)phenyl]acetamide;

Example 13

N-(3-cyclopropyl-1H-pyrazol-5-yl)-2-[4'-(trifluoromethyl)[1,1'-biphenyl]-4-yl]acetamide The bis(pinacolato)diboron (102 mg, 0.4 mmol), potassium acetate (66 mg, 0.6 mmol) and PdCl$_2$(dppf) (1.6 mg, 0.018 mmol) were added sequentially to a degassed suspension of 2-(4-bromophenyl)-N-(5-cyclopropyl-1H-pyrazol-3-yl)acetamide resin linked (200 mg, 0.2 mmol) in anhydrous DMF (10 ml). The resultant mixture was heated at 80° C. under argon for 16 h., cooled down at room temperature and filtered. The resin was washed with DMF (3*3 ml), MeOH (3*3 ml) and CH$_2$Cl$_2$ (3*3 ml) and dried under vacuum.

1-bromo-4-(trifluoromethyl)benzene (225 mg, 1 mmol), tetrakise(triphenylphosphine)palladium (4.6 mg, 0.004 mmol) and 2M aqueous solution of K3PO4 (0.5 ml) we added to the N-(5-cyclopropyl-1H-pyrazol-3-yl)-2-[4-(4,4,5,5-tetramethyl-1,3,2-dioxaborolan-2-yl)phenyl]acetamide resin linked suspended in 10 ml of anhydrous DMF. The mixture was heated at 80° C. under argon for 20 h. and cooled at room temperature. The resin filtered, was washed with DMF (3*3 ml), MeOH (3*3 ml), and DCM (3*3 ml).

The cleavage of the final product was carried out in TFA 15% in DCM (5 ml, 1 h.).

1H-NMR (400 MHz, DMSO-d6) ppm 10.50 (s, 1H, NHCO), 7.8–7.4 (m, 8H, biphenyl), 6.09 (s, 1H, CH-pyrazole), 3.62 (s, 2H, COCH), 1.82 (m, 1H, cyclopropyl-CH);

ESI (+) MS: m/z 386 (100, MH+).

Analogously the following compounds were prepared:

5-(4-{2-[(5-cyclopropyl-1H-pyrazol-3-yl)amino]-2-oxoethyl}phenyl)-2-furoic acid

N-(5-cyclopropyl-1H-pyrazol-3-yl)-2-[4-(3-methyl-1H-pyrazol-4-yl)phenyl]acetamide N-(5-cyclopropyl-1H-pyrazol-3-yl)-2-[4-(3,5-dimethyl-1H-pyrazol-4-yl)phenyl]acetamide N-(5-cyclopropyl-1H-pyrazol-3-yl)-2-[4-(3-furyl)phenyl]acetamide N-(5-cyclopropyl-1H-pyrazol-3-yl)-2-[4-(5-formyl-3-thienyl)phenyl]acetamide

[5-(4-{2-[(5-cyclopropyl-1H-pyrazol-3-yl)amino]-2-oxoethyl}phenyl)-1H-indol-3-yl]acetic acid 5-(4-{2-[(5-cyclopropyl-1H-pyrazol-3-yl)amino]-2-oxoethyl}phenyl)tryptophan N-(5-cyclopropyl-1H-pyrazol-3-yl)-2-[4-(2-pyridinyl)phenyl]acetamide 1-acetyl-5-(4-{2-[(5-cyclopropyl-1H-pyrazol-3-yl)amino]-2-oxoethyl}phenyl)-1H-indol-3-yl acetate 2-[4-(2-amino-4-hydroxy-6-methyl-5-pyrimidinyl)phenyl]-N-(5-cyclopropyl-1H-pyrazol-3-yl)acetamide N-(5-cyclopropyl-1H-pyrazol-3-yl)-2-[4-(5-pyrimidinyl)phenyl]acetamide N-(5-cyclopropyl-1H-pyrazol-3-yl)-2-[4-(2-pyridinyl)phenyl]acetamide N-(5-cyclopropyl-1H-pyrazol-3-yl)-2-[4-(5-nitro-2-pyridinyl)phenyl]acetamide N-(5-cyclopropyl-1H-pyrazol-3-yl)-2-[4-(6-amino-3-pyridinyl)phenyl]acetamide N-(5-cyclopropyl-1H-pyrazol-3-yl)-2-[4-(3-pyridinyl)phenyl]acetamide N-(5-cyclopropyl-1H-pyrazol-3-yl)-2-[4-(3-quinolinyl)phenyl]acetamide N-(5-cyclopropyl-1H-pyrazol-3-yl)-2-[4-(4-isoquinolinyl)phenyl]acetamide 5-(4-{2-[(5-cyclopropyl-1H-pyrazol-3-yl)amino]-2-oxoethyl}phenyl)nicotinic acid N-(5-cyclopropyl-1H-pyrazol-3-yl)-2-[4-(2-amino-5-pyrimidinyl)phenyl]acetamide N-(5-cyclopropyl-1H-pyrazol-3-yl)-2-[4-(4-pyridinyl)phenyl]acetamide N-(5-cyclopropyl-1H-pyrazol-3-yl)-2-[4-(5-acetyl-2-thienyl)phenyl]acetamide N-(5-cyclopropyl-1H-pyrazol-3-yl)-2-[4-(9H-purin-6-yl)phenyl]acetamide 2-[4-(1-benzothien-3-yl)phenyl]-N-(5-cyclopropyl-1H-pyrazol-3-yl)acetamide

[5-(4-{2-[(5-cyclopropyl-1H-pyrazol-3-yl)amino]-2-oxoethyl}phenyl)-1H-indol-3-yl acetate N-(5-cyclopropyl-1H-pyrazol-3-yl)-2-[4-(2,4-dimethoxy-5-pyrimidinyl)phenyl]acetamide N-(5-cyclopropyl-1H-pyrazol-3-yl)-2-[4-(2-chloro-3-thienyl)phenyl]acetamide N-(5-cyclopropyl-1H-pyrazol-3-yl)-2-[4-(6-methyl-2-pyridinyl)phenyl]acetamide N-(5-cyclopropyl-1H-pyrazol-3-yl)-2-[4-(1H-imidazol-5-yl)phenyl]acetamide 2-[4-(6-amino-5-nitro-3-pyridinyl)phenyl]-N-(5-cyclopropyl-1H-pyrazol-3-yl)acetamide N-(5-cyclopropyl-1H-pyrazol-3-yl)-2-[4-(2,3,5,6-tetrafluoro-4-pyridinyl)phenyl]acetamide N-(5-cyclopropyl-1H-pyrazol-3-yl)-2-[4-(4-methyl-2-pyridinyl)phenyl]acetamide N-(5-cyclopropyl-1H-pyrazol-3-yl)-2-[4-(1H-pyrazol-4-yl)phenyl]acetamide 5-(4-{2-[(5-cyclopropyl-1H-pyrazol-3-yl)amino]-2-oxoethyl}phenyl)-2-thiophene acid N-(5-cyclopropyl-1H-pyrazol-3-yl)-2-[4-(6-methoxy-2-pyridinyl)phenyl]acetamide 6-(4-{2-[(5-cyclopropyl-1H-pyrazol-3-yl)amino]-2-oxoethyl}phenyl)-2-pyridinecarboxylic acid N-(5-cyclopropyl-1H-pyrazol-3-yl)-2-[4-(2,4-dichloro-5-pyrimidinyl)phenyl]acetamide N-(5-cyclopropyl-1H-pyrazol-3-yl)-2-[4-(4-methyl-3-thienyl)phenyl]acetamide N-(5-cyclopropyl-1H-pyrazol-3-yl)-2-[4-(5-formyl-2-furyl)phenyl]acetamide N-(5-cyclopropyl-1H-pyrazol-3-yl)-2-[4-(6-nitro-3-pyridinyl)phenyl]acetamide N-(5-cyclopropyl-1H-pyrazol-3-yl)-2-[4-(8-quinolinyl)phenyl]acetamide N-(5-cyclopropyl-1H-pyrazol-3-yl)-2-[4-(5-methyl-2-pyridinyl)phenyl]acetamide N-(5-cyclopropyl-1H-pyrazol-3-yl)-2-[4-(3-methyl-2-pyridinyl)phenyl]acetamide N-(5-cyclopropyl-1H-pyrazol-3-yl)-2-[4-(1H-indol-7-yl)phenyl]acetamide N-(5-cyclopropyl-1H-pyrazol-3-yl)-2-[4-(6-methoxy-3-pyridinyl)phenyl]acetamide N-(5-cyclopropyl-1H-pyrazol-3-yl)-2-[4-(2-amino-9H-purin-6-yl)phenyl]acetamide N-(5-cyclopropyl-1H-pyrazol-3-yl)-2-[4-(2-methyl-1H-indol-5-yl)phenyl]acetamide N-(5-cyclopropyl-1H-pyrazol-3-yl)-2-[4-(6-fluoro-3-pyridinyl)phenyl]acetamide N-(5-cyclopropyl-1H-pyrazol-3-yl)-2-[4'-(ethylsulfanyl)[1,1'-biphenyl]-4-yl]acetamide;

N-(5-cyclopropyl-1H-pyrazol-3-yl)-2-(3',4'-dimethyl[1,1'-biphenyl]-4-yl)acetamide;

N-(5-cyclopropyl-1H-pyrazol-3-yl)-2-(4'-hydroxy[1,1'-biphenyl]-4-yl)acetamide;

(2E)-3-(4'-{2-[(5-cyclopropyl-1H-pyrazol-3-yl)amino]-2-oxoethyl}[1,1'-biphenyl]-3-yl)-2-propenoic acid;

N-(5-cyclopropyl-1H-pyrazol-3-yl)-2-[3'-(trifluoromethyl)[1,1'-biphenyl]-4-yl]acetamide;

N-(5-cyclopropyl-1H-pyrazol-3-yl)-2-(4'-methyl[1,1'-biphenyl]-4-yl)acetamide;

N-(5-cyclopropyl-1H-pyrazol-3-yl)-2-[2'-(methylsulfanyl)[1,1'-biphenyl]-4-yl]acetamide;

4'-{2-[(cyclopropyl-1H-pyrazol-3-yl)amino]-2-oxoethyl}[1,1'-biphenyl]-2-carboxylic acid;

3-(4'-{2-[(5-cyclopropyl-1H-pyrazol-3-yl)amino]-2-oxoethyl}[1,1'-biphenyl]-4-yl)propanoic acid;

2-[4'-(benzyloxy)[1,1'-biphenyl]-4-yl]-N-(5-cyclopropyl-1H-pyrazol-3-yl)acetamide;

N-(5-cyclopropyl-1H-pyrazol-3-yl)-2-(2',3'-dichloro[1,1'-biphenyl]-4-yl)acetamide;

N-(5-cyclopropyl-1H-pyrazol-3-yl)-2-(3'-isopropyl[1,1'-biphenyl]-4-yl)acetamide;

N-(5-cyclopropyl-1H-pyrazol-3-yl)-2-[4-(3-formyl-2-furyl)phenyl]acetamide;

(2E)-3-(4'-{2-[(5-cyclopropyl-1H-pyrazol-3-yl)amino]-2-oxoethyl}[1,1'-biphenyl]-4-yl)-2-propenoic acid;

N-(5-cyclopropyl-1H-pyrazol-3-yl)-2-{4'-[(E)-2-nitroethenyl][1,1'-biphenyl]-4-yl}acetamide;

2-(4'-chloro[1,1'-biphenyl]-4-yl)-N-(5-cyclopropyl-1H-pyrazol-3-yl)acetamide;

N-(5-cyclopropyl-1H-pyrazol-3-yl)-2-(3'-methyl[1,1'-biphenyl]-4-yl)acetamide;

2-(4'-phenyl[1,1'-biphenyl]-4-yl)-N-(5-cyclopropyl-1H-pyrazol-3-yl)acetamide;

N-(5-cyclopropyl-1H-pyrazol-3-yl)-2-(4'-phenoxy[1,1'-biphenyl]-4-yl)acetamide;

N-(5-cyclopropyl-1H-pyrazol-3-yl)-2-(2'-formyl[1,1'-biphenyl]-4-yl)acetamide;

2-(3'-chloro-[1,1'-biphenyl]-4-yl)-N-(5-cyclopropyl-1H-pyrazol-3-yl)acetamide;

N-(5-cyclopropyl-1H-pyrazol-3-yl)-2-(3'-formyl[1,1'-biphenyl]-4-yl)acetamide;

tert-butyl 2-(4-{2-[(5-cyclopropyl-1H-pyrazol-3-yl)amino]-2-oxoethyl}phenyl)-1H-pyrrole-1-carboxylate;

2-(3'-cyano[1,1'-biphenyl]-4-yl)-N-(5-cyclopropyl-1H-pyrazol-3-yl)acetamide;

N-(5-cyclopropyl-1H-pyrazol-3-yl)-2-(4-dibenzo[b,d]furan-4-ylphenyl)acetamide;

Obviously, numerous modifications and variations of the present invention are possible in the light of the above teachings. It is therefore to be understood that within the scope of the appended claims, the invention may be practiced otherwise than as specifically described herein.

What is claimed is:

1. A 3-amino-pyrazole derivative represented by formula (I):

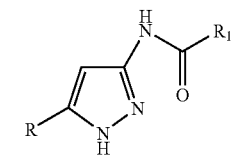

wherein
R is a $C_3$–$C_6$ cycloalkyl group optionally substituted by a straight or branched $C_1$–$C_6$ alkyl or arylalkyl group;
$R_1$ is a phenylalkyl which may be optionally further substituted;
or a pharmaceutically acceptable salt thereof.

2. The 3-amino-pyrazole derivative of claim 1, wherein R is a $C_3$–$C_6$ cycloalkyl group optionally substituted by a straight or branched $C_1$–$C_6$ alkyl group;
$R_1$ is phenylalkyl, which is optionally substituted with one or more groups selected from the group consisting of cycloalkyl, hydroxy, alkylthio, alkoxy, amino, alkylamino, dialkylamino, alkoxycarbonylamino, alkoxycarbonylalkylamino, alkylcarbonyl, alkylsulphonyl, alkoxycarbonyl, carboxy, halogen, nitro, aryloxy, arylthio, arylsulphonyl, N-alkyl-piperazinyl, piperidinyl, 4-morpholinyl, arylamino, cyano, alkyl, aryl, oxo, haloaryl, haloarylalkyl, haloaryloxy, haloarylsulphonyl, aminosulphonyl, aminocarbonyl, arylcarbonyl, perfluorinated alkyl, and perfluorinated alkoxy groups;
or a pharmaceutically acceptable salt thereof.

3. The 3-amino-pyrazole of claim 1, wherein R is an unsubstituted $C_3$–$C_6$ cycloalkyl group.

4. The 3-amino-pyrazole of claim 1, wherein R is cycloalkyl and $R_1$ is phenyl $C_1$–$C_6$ alkyl.

5. The 3-amino-pyrazole of claim 3 or 4, wherein R is cyclopropyl.

6. The 3-amino-pyrazole of claim 1, wherein $R_1$ is optionally substituted in any of the free positions by one or more groups independently selected from: halogen, nitro, oxo groups (C=O), cyano, alkyl, perfluorinated alkyl, hydroxyalkyl, aryl, arylalkyl, heterocyclyl, cycloalkyl, hydroxy, alkoxy, perfluorinated alkoxy, aryloxy, heterocyclyloxy, methylenedioxy, alkylcarbonyloxy, arylcarbonyloxy, carboxy, alkoxycarbonyl, aryloxycarbonyl, cycloalkyloxycarbonyl, amino, ureido, alkylamino, dialkylamino, arylamino, diarylamino, formylamino, alkylcarbonylamino, arylcarbonylamino, heterocyclylcarbonylamino, alkoxycarbonylamino, alkoxyimino, alkylsulfonylamino, arylsulfonylamino, formyl, alkylcarbonyl, arylcarbonyl, cycloalkylcarbonyl, heterocyclylcarbonyl, aminocarbonyl, alkylaminocarbonyl, dialkylaminocarbonyl, alkylsulfonyl, arylsulfonyl, aminosulfonyl, alkylaminosulfonyl, dialkylaminosulfonyl, arylthio and alkylthio.

7. The 3-amino-pyrazole derivative of claim 1, which is selected from the group consisting of:
- N-(5-cyclopropyl-1H-pyrazol-3-yl)-2,2-diphenylacetamide;
- N-(3-cyclopropyl-1H-pyrazol-5-yl)-2-(4-nitrophenyl)acetamide;
- N-(3-cyclopropyl-1H-pyrazol-5-yl)-4-methoxybenzamide;
- N-(3-cyclopropyl-1H-pyrazol-5-yl)-2-(3-methoxyphenyl)acetamide;
- N-(3-cyclopropyl-1H-pyrazol-5-yl)-2-[4-(dimethylamino)phenyl]acetamide;
- N-(3-cyclopropyl-1H-pyrazol-5-yl)-1-phenylcyclopropancarboxamide;
- 2-(1,3-benzodioxol-5-yl-N-(3-cyclopropyl-1H-pyrazol-5-yl)acetamide;
- N-(3-cyclopropyl-1H-pyrazol-5-yl)-2-(4-methoxyphenyl)acetamide;
- N-(3-cyclopropyl-1H-pyrazol-5-yl)-2-phenylpropanamide;
- N-(3-cyclopropyl-1H-pyrazol-5-yl)-2-(3,4-dimethoxyphenyl)acetamide;
- 2-(4-chlorophenyl)-N-(3-cyclopropyl-1H-pyrazol-5-yl)acetamide;
- N-(3-cyclopropyl-1H-pyrazol-5-yl)-4-oxo-4-phenylbutanamide;
- N-(3-cyclopropyl-1H-pyrazol-5-yl)-2-oxo-2-phenylacetamide;
- N-(3-cyclopropyl-1H-pyrazol-5-yl)-2-(4-methylphenyl)acetamide;
- 2-[1,1'-biphenyl]-4-yl-N-(3-cyclopropyl-1H-pyrazol-5-yl)acetamide;
- N-(3-cyclopropyl-1H-pyrazol-5-yl)-2-(3-chlorophenyl)acetamide;
- N-(3-cyclopropyl-1H-pyrazol-5-yl)-2-(2-fluorophenyl)acetamide;
- N-(3-cyclopropyl-1H-pyrazol-5-yl)-2-(2-chlorophenyl)acetamide;
- N-(3-cyclopropyl-1H-pyrazol-5-yl)-2-(4-fluorophenyl)acetamide;
- N-(3-cyclopropyl-1H-pyrazol-5-yl)-2-(4-trifluoromethylphenyl)acetamide;
- N-(3-cyclopropyl-1H-pyrazol-5-yl)-2-methoxy-2-phenylacetamide;
- N-(5-cyclopropyl-1H-pyrazol-3-yl)-2-phenylacetamide;
- N-(5-cyclopropyl-1H-pyrazol-3-yl)-2-(2,5-dimethoxyphenyl)acetamide;
- N-(3-cyclopropyl-1H-pyrazol-5-yl)-3-phenylpropanamide;
- N-(3-cyclopropyl-1H-pyrazol-5-yl)-2-[5-(2,6-difluorobenzyl)-2-methoxyphenyl]acetamide;
- 2-(4-bromophenyl)-N-(5-cyclopropyl-1H-pyrazol-3-yl)-acetamide;
- N-(5-cyclopropyl-1H-pyrazol-3-yl)-2-[4-(1-pyrrolidinyl)phenyl]acetamide;
- N-(5-cyclopropyl-1H-pyrazol-3-yl)-2-(4$^1$-(hydroxymethyl)[1,1$^1$-biphenyl]-4-yl)acetamide;
- N-5-cyclopropyl-1H-pyrazol-3-yl)-2-[4-(3-thienyl)phenyl]acetamide;
- N-(5-cyclopropyl-1H-pyrazol-3-yl)-2-(4$^1$-fluoro[1,1,$^1$-biphenyl]-4-yl)acetamide;
- 4$^1$-{2-[(5-cyclopropyl-1H-pyrazol-3-yl)amino]-2-oxoethyl}[1.1$^1$-biphenyl]-4-carboxylic acid;
- 4$^1$-{2-[(5-cyclopropyl-1H-pyrazol-3-yl)amino]-2-oxethyl}[1,1$^1$-biphenyl]-4-carboxamide;
- N-(5-cyclopropyl-1H-pyrazol-3-yl)-2-(4$^1$-formyl[1,1$^1$-biphenyl]-4-yl)acetamide;
- N-(5-cyclopropyl-1H-pyrazol-3-yl)-2-{4$^1$-[(dimethylamino)methyl)[1,1$^1$-biphenyl]-4-yl}acetamide;
- 2-amino-N-(4-{2-[(5-cyclopropyl-1H-pyrazol-3-yl)amino]-2-oxethyl}phenyl)acetamide;
- 2-[4-aminomethyl)phenyl]-N-(5-cyclopropyl-1H-pyrazol-3-yl)acetamide;
- 2-[4'-(aminomethyl)[1,1'-biphenyl]-4-yl]-N-(5-cyclopropyl-1H-pyrazol-3-yl)acetamide;
- N-(5-cyclopropyl-1H-pyrazol-3-yl)-2-{4'-[(methylamino)methyl][1,1'-biphenyl]-4-yl}acetamide;
- N-(5-cyclopropyl-1H-pyrazol-3-yl)-2-[4'-(1-pyrrolidinylmethyl)[1,1'-biphenyl]-4-yl]acetamide;
- N-(5-cyclopropyl-1H-pyrazol-3-yl)-2-[4'-(1-piperidinylmethyl)[1,1'-biphenyl]-4-yl]acetamide;
- N-(5-cyclopropyl-1H-pyrazol-3-yl)-2-[4'-(4-morpholinylmethyl)[1,1'-biphenyl]-4-yl]acetamide;
- N-(5-cyclopropyl-1H-pyrazol-3-yl)-2-{4'-[(4-methyl-1-piperazinyl)methyl][1,1'-biphenyl]-4-yl}acetamide;
- N-(5-cyclopropyl-1H-pyrazol-3-yl)-2-[4'-(1H-imidazol-2-yl)[1,1'-biphenyl]-4-yl]acetamide;
- N-(5-cyclopropyl-1H-pyrazol-3-yl)-2-(4-{[dimethylamino)carbonyl]amino}phenyl)acetamide;
- N-(5-cyclopropyl-1H-pyrazol-3-yl)-2-{4-[(methylsulfonyl)amino]phenyl}acetamide;
- 2-[4-(aminomethyl)phenyl]-N-(5-cyclopropyl-1H-pyrazol-3-yl)acetamide;
- 2-{4-[(acetylamino)methyl]phenyl}-N-(5-cyclopropyl-1H-pyrazol-3-yl)acetamide;
- 2-[4-(aminosulfonyl)phenyl]-N-(5-cyclopropyl-1H-pyrazol-3-yl)acetamide;
- N-(5-cyclopropyl-1H-pyrazol-3-yl)-2-[4-(2-oxo-1-pyrrolidinyl)phenyl]acetamide;
- 2-[1,1'-biphenyl]-4-yl-N-(3-cyclopropyl-1H-pyrazol-5-yl)propanamide;
- N-(3-cyclopropyl-1H-pyrazol-5-yl)-2-(4-phenoxyphenyl)acetamide;
- 2-[4-(acetylamino)phenyl]-N-(3-cyclopropyl-1H-pyrazol-5-yl)acetamide;
- N-(4-{2-[(3-cyclopropyl-1H-pyrazol-5-yl)amino]-2-oxoethyl}phenyl)-1-pyrrolidinecarboxamide;
- N-(4-{2-[(3-cyclopropyl-1H-pyrazol-5-yl)amino]-2-oxoethyl}phenyl)-1-piperidinecarboxamide;
- N-(4-{2-[(3-cyclopropyl-1H-pyrazol-5-yl)amino]-2-oxoethyl}phenyl)-4-morpholinecarboxamide;
- N-(4-{2-[(3-cyclopropyl-1H-pyrazol-5-yl)amino]-2-oxoethyl}phenyl)-4-methyl-1-piperazinecarboxamide;
- N-(5-cyclopropyl-1H-pyrazol-3-yl)-2-(4'-ethyl[1,1'-biphenyl]-4-yl)acetamide;
- N-(5-cyclopropyl-1H-pyrazol-3-yl)-2-(4'-propyl[1,1'-biphenyl]-4-yl)acetamide;
- N-(5-cyclopropyl-1H-pyrazol-3-yl)-2-(4'-hydroxy[1,1'-biphenyl]-4-yl)acetamide;
- 2-(4'-cyano[1,1'-biphenyl]-4-yl)-N-(5-cyclopropyl-1H-pyrazol-3-yl)acetamide;
- 2-(4'-bromo[1,1'-biphenyl]-4-yl)-N-(5-cyclopropyl-1H-pyrazol-3-yl)acetamide;
- N-(5-cyclopropyl-1H-pyrazol-3-yl)-2-(4'-propoxy[1,1'-biphenyl]-4-yl)acetamide;
- N-(5-cyclopropyl-1H-pyrazol-3-yl)-2-(4'-butoxy[1,1'-biphenyl]-4-yl)acetamide;

N-(5-cyclopropyl-1H-pyrazol-3-yl)-2-(4'-pentoxy[1,1'-biphenyl]-4-yl)acetamide;
4'-{2-[(5-cyclopropyl-1H-pyrazol-3-yl)amino]-2-oxoethyl}[1,1'-biphenyl]-4-yl acetate;
2-(4'-tert-butyl[1,1'-biphenyl]-4-yl)-N-(5-cyclopropyl-1H-pyrazol-3-yl)acetamide;
N-(5-cyclopropyl-1H-pyrazol-3-yl)-2-(3',4'-dichloro[1,1'-biphenyl]-4-yl)acetamide;
N-(5-cyclopropyl-1H-pyrazol-3-yl)-2-(3'-hydroxy[1,1'-biphenyl]-4-yl)acetamide;
2-(3'-bromo[1,1'-biphenyl]-4-yl)-N-(5-cyclopropyl-1H-pyrazol-3-yl)acetamide;
2-(3'-amino[1,1'-biphenyl]-4-yl)-N-(5-cyclopropyl-1H-pyrazol-3-yl)acetamide;
2-(4'-amino[1,1'-biphenyl]-4-yl)-N-(5-cyclopropyl-1H-pyrazol-3-yl)acetamide;
4'-{2-[(5-cyclopropyl-1H-pyrazol-3-yl)amino]-2-oxoethyl}-N-[2-(1-pyrrolidinyl)ethyl][1,1'-biphenyl]-4-carboxamide;
4'-{2-[(5-cyclopropyl-1H-pyrazol-3-yl)amino]-2-oxoethyl}-N-[2-(1-pyrrolidinyl)propyl][1,1'-biphenyl]-4-carboxamide;
4'-{2-[(5-cyclopropyl-1H-pyrazol-3-yl)amino]-2-oxoethyl}-N-[2-(1-piperidinyl)ethyl][1,1'-biphenyl]-4-carboxamide;
4'-{2-[(5-cyclopropyl-1H-pyrazol-3-yl)amino]-2-oxoethyl}-N-[2-(1-piperidinyl)propyl][1,1'-biphenyl]-4-carboxamide;
4'-{2-[(5-cyclopropyl-1H-pyrazol-3-yl)amino]-2-oxoethyl}-N-[2-(4-morpholinyl)ethyl][1,1'-biphenyl]-4-carboxamide;
4'-{2-[(5-cyclopropyl-1H-pyrazol-3-yl)amino]-2-oxoethyl}-N-[2-(4-morpholinyl)propyl][1,1'-biphenyl]-4-carboxamide;
4'-{2-[(5-cyclopropyl-1H-pyrazol-3-yl)amino]-2-oxoethyl}-N-[2-(4-methyl-1-piperazinyl)ethyl][1,1'-biphenyl]-4-carboxamide;
4'-{2-[(5-cyclopropyl-1H-pyrazol-3-yl)amino]-2-oxoethyl}-N-[2-(4-methyl-1-piperazinyl)propyl][1,1'-biphenyl]-4-carboxamide;
(2S)-N-(3-cyclopropyl-1H-pyrazol-5-yl)-3,3,3-trifluoro-2-methoxy-2-phenylpropanamide;
(2S)-N-(3-cyclopropyl-1H-pyrazol-5-yl)-2-methoxy-2-phenylethanamide;
N-(5-cyclopropyl-1H-pyrazol-3-yl)-2-(2,5-difluorophenyl)acetamide;
N-(5-cyclopropyl-1H-pyrazol-3-yl)-2-(3-methylphenyl)acetamide;
N-(5-cyclopropyl-1H-pyrazol-3-yl)-2-(3-hydroxyphenyl)acetamide;
(2S)-2-amino-N-(3-cyclopropyl-1H-pyrazol-5-yl)-2-phenylethanamide;
N-(5-cyclopropyl-1H-pyrazol-3-yl)-2-(4-nitrophenyl)propanamide;
N-(5-cyclopropyl-1H-pyrazol-3-yl)-2-(4-hydroxy-3-methoxyphenyl)acetamide;
N-(5-cyclopropyl-1H-pyrazol-3-yl)-2-[3,5-bis(trifluoromethyl)phenyl]acetamide;
N-(5-cyclopropyl-1H-pyrazol-3-yl)-2-(2-chloro-6-fluorophenyl)acetamide;
N-(5-cyclopropyl-1H-pyrazol-3-yl)-2-hydroxy-2-(4-hydroxy-3-methoxyphenyl)acetamide;
N-(5-cyclopropyl-1H-pyrazol-3-yl)-2-{4-[(2S)-2-aminopropanoyloxymethyl]phenyl}acetamide;
N-(5-cyclopropyl-1H-pyrazol-3-yl)-2-(4-bromomethylphenyl)acetamide;
N-(5-cyclopropyl-1H-pyrazol-3-yl)-2-(4-methylsulphonylphenyl)acetamide;
(2R)-N-(3-cyclopropyl-1H-pyrazol-5-yl)-2-methoxy-2-phenylethanamide;
N-(5-cyclopropyl-1H-pyrazol-3-yl)-2-(2-methylphenyl)acetamide;
N-(5-cyclopropyl-1H-pyrazol-3-yl)-2-(3,5-dimethoxyphenyl)acetamide;
N-(5-cyclopropyl-1H-pyrazol-3-yl)-2-(3,4-difluorophenyl)acetamide;
N-(5-cyclopropyl-1H-pyrazol-3-yl)-2-(3,4-dichlorophenyl)acetamide;
N-(5-cyclopropyl-1H-pyrazol-3-yl)-2-(3-bromophenyl)acetamide;
2-cyclohexyl-N-(3-cyclopropyl-1H-pyrazol-5-yl)-2-phenylacetamide;
(1R)-2-[(3-cyclopropyl-1H-pyrazol-5-yl)amino]-2-oxo-1-phenylethyl acetate;
N-(5-cyclopropyl-1H-pyrazol-3-yl)-2-(2-hydroxy-2-diphenyl)acetamide;
N-(5-cyclopropyl-1H-pyrazol-3-yl)-2-(4-methylsulfanylphenyl)acetamide;
N-(5-cyclopropyl-1H-pyrazol-3-yl)-2-(2-bromophenyl)acetamide;
N-(5-cyclopropyl-1H-pyrazol-3-yl)-2-(4-hydroxy-3-nitrophenyl)acetamide;
N-(5-cyclopropyl-1H-pyrazol-3-yl)-2-(3-chloro-4-hydroxyphenyl)acetamide;
N-(5-cyclopropyl-1H-pyrazol-3-yl)-2-(2-acetylamino-2-phenyl)acetamide;
N-(5-cyclopropyl-1H-pyrazol-3-yl)-2-(3-nitrophenyl)acetamide;
N-(5-cyclopropyl-1H-pyrazol-3-yl)-2-(2-bromo-2-phenyl)acetamide;
N-(5-cyclopropyl-1H-pyrazol-3-yl)-2-(4-benzyloxy-3-methoxyphenyl)acetamide;
(2S)-N-(5-cyclopropyl-1H-pyrazol-3-yl)-2-hydroxy-2-phenylethanamide;
N-(5-cyclopropyl-1H-pyrazol-3-yl)-2-(3-trifluoromethylphenyl)acetamide;
N-(5-cyclopropyl-1H-pyrazol-3-yl)-2-(2,4-dichlorophenyl)acetamide;
N-(5-cyclopropyl-1H-pyrazol-3-yl)-2-(3,4-dihydroxyphenyl)acetamide;
N-(5-cyclopropyl-1H-pyrazol-3-yl)-2-(3,5-di-tert-butyl-4-hydroxyphenyl)acetamide;
N-(5-cyclopropyl-1H-pyrazol-3-yl)-2-(3,5-difluorophenyl)acetamide;
N-(5-cyclopropyl-1H-pyrazol-3-yl)-2-benzyloxycarbonyl-2-phenylacetamide;
N-(5-cyclopropyl-1H-pyrazol-3-yl)-2-(4-butoxyphenyl)acetamide;
N-(5-cyclopropyl-1H-pyrazol-3-yl)-2-(3-fluorophenyl)acetamide;
5-cyclohexyl 1-(4-{2-[(5-cyclopropyl-1H-pyrazol-3-yl)amino]-2-oxoethyl}benzyl) 2-aminopentanedioate;
N-(5-cyclopropyl-1H-pyrazol-3-yl)-2-(4-isobutylphenyl)propanamide;
N-(5-cyclopropyl-1H-pyrazol-3-yl)-2-(4-hydroxyphenyl)acetamide;
2-cyclopentyl-N-(5-cyclopropyl-1H-pyrazol-3-yl)-2-phenylacetamide;
(1S)-2-[(3-cyclopropyl-1H-pyrazol-5-yl)amino]-2-oxo-1-phenylethyl acetate;
N-(3-cyclopropyl-1H-pyrazol-5-yl)-2-fluoro-2-phenylacetamide;

N-(5-cyclopropyl-1H-pyrazol-3-yl)-2-(2-trifluoromethylphenyl)acetamide;
N-(5-cyclopropyl-1H-pyrazol-3-yl)-2-(2-methoxyphenyl)acetamide;
N-(5-cyclopropyl-1H-pyrazol-3-yl)-2-(3,4,5-trimethoxyphenyl)acetamide;
2-chloro-2,2-bis(2-chlorophenyl)-N-(5-cyclopropyl-1H-pyrazol-3-yl)acetamide;
N-(5-cyclopropyl-1H-pyrazol-3-yl)-2-hydroxy-2-(3-hydroxy-4-methoxyphenyl)acetamide;
N-(5-cyclopropyl-1H-pyrazol-3-yl)-2-(pentafluorophenyl)acetamide;
N-(3-cyclopropyl-1H-pyrazol-5-yl)-3-methyl-2-phenylpentamide;
N-(5-cyclopropyl-1H-pyrazol-3-yl)-2-(2-nitrophenyl)acetamide;
N-(5-cyclopropyl-1H-pyrazol-3-yl)-2-(4-trifluoromethoxyphenyl)acetamide;
N-(5-cyclopropyl-1H-pyrazol-3-yl)-2-(4-ethoxyphenyl)acetamide;
N-(5-cyclopropyl-1H-pyrazol-3-yl)-2-(2-fluorophenyl)acetamide;
N-(5-cyclopropyl-1H-pyrazol-3-yl)-2-(2-nitro-4-trifluoromethylphenyl)acetamide;
N-(5-cyclopropyl-1H-pyrazol-3-yl)-2-(2,6-dichlorophenyl)acetamide;
N-(5-cyclopropyl-1H-pyrazol-3-yl)-2-(2,4-dinitrophenyl)acetamide;
N-(5-cyclopropyl-1H-pyrazol-3-yl)-2,4-difluorophenylacetamide;
N-(5-cyclopropyl-1H-pyrazol-3-yl)-2-(3-bromo-4-methoxyphenyl)acetamide;
N-(5-cyclopropyl-1H-pyrazol-3-yl)-3-hydroxy-2-phenylpropanamide;
N-(5-cyclopropyl-1H-pyrazol-3-yl)-2-(3-fluoro-4-hydroxyphenyl)acetamide;
N-(5-cyclopropyl-1H-pyrazol-3-yl)-1-phenylcyclopropanecarboxamide;
N-(5-cyclopropyl-1H-pyrazol-3-yl)-2-(2,6-difluorophenyl)acetamide;
N-(5-cyclopropyl-1H-pyrazol-3-yl)-2-(2,5-dihydroxyphenyl)acetamide;
N-(5-cyclopropyl-1H-pyrazol-3-yl)-2-(2,4,6-trimethylphenyl)acetamide;
N-(5-cyclopropyl-1H-pyrazol-3-yl)-2-[2,5-bis(trifluoromethyl)phenyl]acetamide;
N-(5-cyclopropyl-1H-pyrazol-3-yl)-2-(5-methoxy-3-hydroxy-2-propylphenyl)acetamide;
N-(3-cyclopropyl-1H-pyrazol-5-yl)-2-(2-fluoro-[1,1'-biphenyl]-4-yl)propanamide;
(2R)-N-(3-cyclopropyl-1H-pyrazol-5-yl)-2-(2-fluoro[1,1'-biphenyl]-4-yl)propanamide;;
2-{4-[(aminocarbonyl)amino]phenyl}-N-(5-cyclopropyl-1H-pyrazol-3-yl)acetamide;
2-{4-[(2-amino-2-oxoethyl)amino]phenyl}-N-(5-cyclopropyl-1H-pyrazol-3-yl)acetamide;
4-bromo-N-(4-{2-[(5-cyclopropyl-1H-pyrazol-3-yl)amino]-2-oxoethyl}-1,3-thiazol-2-yl)benzamide
N-(5-cyclopropyl-1H-pyrazol-3-yl)-2-(2-iodophenyl)acetamide;
N-(4-{2-[(5-cyclopropyl-1H-pyrazol-3-yl)amino]-2-oxoethyl}-1,3-thiazol-2-yl)benzamide;
N-(5-cyclopropyl-1H-pyrazol-3-yl)-2-(2-hydroxyphenyl)acetamide;
N-(5-cyclopropyl-1H-pyrazol-3-yl)-2-(3-methylsulfonaylaminophenyl)acetamide;
N-(5-cyclopropyl-1H-pyrazol-3-yl)-2-(4-methylsulfonaylaminophenyl)acetamide;
N-(5-cyclopropyl-1H-pyrazol-3-yl)-2-{4-[2-(4-methyl-1-piperazinyl)ethoxy]phenyl}acetamide;
N-(5-cyclopropyl-1H-pyrazol-3-yl)-2-{4-[2-(1-pyrrolidinyl)ethoxy]phenyl}acetamide;
N-(5-cyclopropyl-1H-pyrazol-3-yl)-2-{4-(2-amino-2-oxoethoxy)phenyl}acetamide;
N-(5-cyclopropyl-1H-pyrazol-3-yl)-2-{4-[2-oxo-2-(1-pyrrolidinyl)ethoxy]phenyl}acetamide;
N-(5-cyclopropyl-1H-pyrazol-3-yl)-2-[3-(2-amino-2-oxoethoxy)phenyl]acetamide;
N-(5-cyclopropyl-1H-pyrazol-3-yl)-2-(3-methoxyphenyl)acetamide;
N-(5-cyclopropyl-1H-pyrazol-3-yl)-2-[4-(1-oxo-1,3-dihydro-2H-isoindol-2-yl)phenyl]hexanamide;
2-[1,1'-biphenyl]-4-yl-N-(5-cyclopropyl-1H-pyrazol-3-yl)butanamide;
N-(5-cyclopropyl-1H-pyrazol-3-yl)-2-[4-(1,3-dihydro-2H-isoindol-2-yl)phenyl]propanamide;
N-(5-cyclopropyl-1H-pyrazol-3-yl)-2-[4-(1-oxo-1,3-dihydro-2H-isoindol-2-yl)phenyl]butanamide;
N-(5-cyclopropyl-1H-pyrazol-3-yl)-(2S)-2-[4-(1-oxo-1,3-dihydro-2H-isoindol-2-yl)phenyl]propanamide;
N-(5-cyclopropyl-1H-pyrazol-3-yl)-2-[4-(5-amino-4-phenyl-1H-1,2,3-triazol-1-yl)phenyl]acetamide;
N-(5-cyclopropyl-1H-pyrazol-3-yl)-2-[4-(1-oxo-1,3-dihydro-2H-isoindol-2-yl)phenyl]pentanamide;
N-(5-cyclopropyl-1H-pyrazol-3-yl)-2-(4-benzyloxyphenyl)acetamide;
N-(5-cyclopropyl-1H-pyrazol-3-yl)-2-{4-[(3,3-diethyl-4-oxo-2-azetidinyl)oxy]phenyl}acetamide;
2-[1,1'-biphenyl]-4-yl-N-(5-cyclopropyl-1H-pyrazol-3-yl)-2-hydroxyacetamide;
N-(5-cyclopropyl-1H-pyrazol-3-yl)-3-bromo-2,2-diphenylpropanamide;
N-(5-cyclopropyl-1H-pyrazol-3-yl)-2-(4-hydroxy-5-isopropyl-2-methylphenyl)acetamide;
N-(5-cyclopropyl-1H-pyrazol-3-yl)-2-(2,3,6-trifluorophenyl)acetamide;
N-(5-cyclopropyl-1H-pyrazol-3-yl)-2-(4'-fluoro[1,1'-biphenyl]-4-yl)acetamide
N-(5-cyclopropyl-1H-pyrazol-3-yl)-2-(2'-fluoro[1,1'-biphenyl]-4-yl)acetamide
N-(5-cyclopropyl-1H-pyrazol-3-yl)-2-(3'-fluoro[1,1'-biphenyl]-4-yl)acetamide
N-(5-cyclopropyl-1H-pyrazol-3-yl)-2-(3'-methoxy[1,1'-biphenyl]-4-yl)acetamide
N-(5-cyclopropyl-1H-pyrazol-3-yl)-2-(pentafluoro[1,1'-biphenyl]-4-yl)acetamide
N-(5-cyclopropyl-1H-pyrazol-3-yl)-2-(4'-(trifluoromethoxy)[1,1'-biphenyl]-4-yl)acetamide
N-(5-cyclopropyl-1H-pyrazol-3-yl)-2-(4'-carboxy[1,1'-biphenyl]-4-yl)acetamide
N-(5-cyclopropyl-1H-pyrazol-3-yl)-2-(3'-formyl-4'-methoxy[1,1'-biphenyl]-4-yl)acetamide
N-(5-cyclopropyl-1H-pyrazol-3-yl)-2-(4'-fluoro-3'-methyl[1,1'-biphenyl]-4-yl)acetamide
N-(5-cyclopropyl-1H-pyrazol-3-yl)-2-(2',5'-dichloro[1,1'-biphenyl]-4-yl)acetamide
N-(5-cyclopropyl-1H-pyrazol-3-yl)-2-(3'-acetyl[1,1'-biphenyl]-4-yl)acetamide
N-(5-cyclopropyl-1H-pyrazol-3-yl)-2-(4'-formyl[1,1'-biphenyl]-4-yl)acetamide
N-(5-cyclopropyl-1H-pyrazol-3-yl)-2-(2',5' difluoro[1,1'-biphenyl]-4-yl)acetamide N-(5-cyclopropyl-1H-pyrazol-3-yl)-2-(2',5'-dimethyl[1,1'-biphenyl]-4-yl)acetamide
N-(5-cyclopropyl-1H-pyrazol-3-yl)-2-(2',6-difluoro[1,1'-biphenyl]-4-yl)acetamide
N-(5-cyclopropyl-1H-pyrazol-3-yl)-2-(4'-methoxy[1,1'-biphenyl]-4-yl)acetamide
N-(5-cyclopropyl-1H-pyrazol-3-yl)-2-(2',6-dimethyl[1,1'-biphenyl]-4-yl)acetamide
N-(5-cyclopropyl-1H-pyrazol-3-yl)-2-(5'-fluoro-2'-methoxy[1,1'-biphenyl]-4-yl)acetamide
N-(5-cyclopropyl-1H-pyrazol-3-yl)-2-(2',5'-dimethoxy[1,1'-biphenyl]-4-yl)acetamide
N-(5-cyclopropyl-1H-pyrazol-3-yl)-2-(2',6-dimethoxy[1,1'-biphenyl]-4-yl)acetamide
N-(5-cyclopropyl-1H-pyrazol-3-yl)-2-(4'-acetyl-[1,1'-biphenyl]-4-yl)acetamide
N-(5-cyclopropyl-1H-pyrazol-3-yl)-2-(4'-ethoxy-[1,1'-biphenyl]-4-yl)acetamide
N-(5-cyclopropyl-1H-pyrazol-3-yl)-2-((4'-methylthio)-[1,1'-biphenyl]-4-yl)acetamide
N-(5-cyclopropyl-1H-pyrazol-3-yl)-2-(3'-chloro-4'-fluoro-[1,1'-biphenyl]-4-yl)acetamide
N-(5-cyclopropyl-1H-pyrazol-3-yl)-2-(2'-acetyl-[1,1'-biphenyl]-4-yl)acetamide
N-(5-cyclopropyl-1H-pyrazol-3-yl)-2-(4'-ethyl-[1,1'-biphenyl]-4-yl)acetamide
N-(5-cyclopropyl-1H-pyrazol-3-yl)-2-(3'-ethoxy-[1,1'-biphenyl]-4-yl)acetamide
N-(5-cyclopropyl-1H-pyrazol-3-yl)-2-(3',4'-dimethoxy-[1,1'-biphenyl]-4-yl)acetamide
N-(5-cyclopropyl-1H-pyrazol-3-yl)-2-(2'-ethoxy-[1,1'-biphenyl]-4-yl)acetamide
N-(5-cyclopropyl-1H-pyrazol-3-yl)-2-(3',5'-difluoro-[1,1'-biphenyl]-4-yl)acetamide
N-(5-cyclopropyl-1H-pyrazol-3-yl)-2-(2',4'-dimethoxy-[1,1'-biphenyl]-4-yl)acetamide
N-(5-cyclopropyl-1H-pyrazol-3-yl)-2-(2',3'-dimethyl-[1,1'-biphenyl]-4-yl)acetamide
N-(5-cyclopropyl-1H-pyrazol-3-yl)-2-(3'-(trifluoromethoxy)[1,1'-biphenyl]-4-yl)acetamide
N-(5-cyclopropyl-1H-pyrazol-3-yl)-2-(3',4'-difluoro-[1,1'-biphenyl]-4-yl)acetamide
N-(5-cyclopropyl-1H-pyrazol-3-yl)-2-(4'-tert-butyl-[1,1'-biphenyl]-4-yl)acetamide
N-(5-cyclopropyl-1H-pyrazol-3-yl)-2-(3'-acetamido[1,1'-biphenyl]-4-yl)acetamide
N-(5-cyclopropyl-1H-pyrazol-3-yl)-2-(4'-trifluoromethyl-[1,1'-biphenyl]-4-yl)acetamide
N-(5-cyclopropyl-1H-pyrazol-3-yl)-2-(3'-(hydroxymethyl)[1,1'-biphenyl]-4-yl)acetamide
N-(5-cyclopropyl-1H-pyrazol-3-yl)-2-(3'-nitro[1,1'-biphenyl]-4-yl)acetamide
N-(5-cyclopropyl-1H-pyrazol-3-yl)-2-(4'-(hydroxymethyl)[1,1'-biphenyl]-4-yl)acetamide
N-(5-cyclopropyl-1H-pyrazol-3-yl)-2-(2'-chloro-[1,1'-biphenyl]-4-yl)acetamide
2-[4-(1,3-benzodioxol-5-yl)phenyl]-N-(5-cyclopropyl-1H-pyrazol-3-yl)acetamide;
N-(5-cyclopropyl-1H-pyrazol-3-yl)-2-[4-(1-naphthyl)phenyl]acetamide;
N-(5-cyclopropyl-1H-pyrazol-3-yl)-2-[4-(2-naphthyl)phenyl]acetamide;
N-(5-cyclopropyl-1H-pyrazol-3-yl)-2-[4-(2-furyl)phenyl]acetamide;
2-[4-(5-acetyl-2-thienyl)phenyl]-N-(5-cyclopropyl-1H-pyrazol-3-yl)acetamide;
2-[4-(5-chloro-2-thienyl)phenyl]-N-(5-cyclopropyl-1H-pyrazol-3-yl)acetamide;
N-(5-cyclopropyl-1H-pyrazol-3-yl)-2-[4-(5-methyl-2-thienyl)phenyl]acetamide;
2-[4-(1-benzofuran-2-yl)phenyl]-N-(5-cyclopropyl-1H-pyrazol-3-yl)acetamide;
N-(5-cyclopropyl-1H-pyrazol-3-yl)-2-[4-(2-thienyl)phenyl]acetamide;
N-(5-cyclopropyl-1H-pyrazol-3-yl)-2-[3'-({[5-(dimethylamino)-1-naphthyl]sulfonyl}amino)[1,1'-biphenyl]-4-yl]acetamide;
2-[4-(1-benzothien-2-yl)phenyl]-N-(5-cyclopropyl-1H-pyrazol-3-yl)acetamide;
N-(5-cyclopropyl-1H-pyrazol-3-yl)-2-[4-(3-formyl-2-thienyl)phenyl]acetamide;
N-(5-cyclopropyl-1H-pyrazol-3-yl)-2-[4-(3-formyl-2-thienyl)phenyl]acetamide;
5-(4-{2-[(5-cyclopropyl-1H-pyrazol-3-yl)amino]-2-oxoethyl}phenyl)-2-furoic acid;
N-(5-cyclopropyl-1H-pyrazol-3-yl)-2-[4-(3-methyl-1H-pyrazol-4-yl)phenyl]acetamide;
N-(5-cyclopropyl-1H-pyrazol-3-yl)-2-[4-(3,5-dimethyl-1H-pyrazol-4-yl)phenyl]acetamide;
N-(5-cyclopropyl-1H-pyrazol-3-yl)-2-[4-(3-furyl)phenyl]acetamide;
N-(5-cyclopropyl-1H-pyrazol-3-yl)-2-[4-(5-formyl-3-thienyl)phenyl]acetamide;
[5-(4-{2-[(5-cyclopropyl-1H-pyrazol-3-yl)amino]-2-oxoethyl}phenyl)-1H-indol-3-yl]acetic acid;
5-(4-{2-[(5-cyclopropyl-1H-pyrazol-3-yl)amino]-2-oxoethyl}phenyl)tryptophan;
N-(5-cyclopropyl-1H-pyrazol-3-yl)-2-[4-(2-pyridinyl)phenyl]acetamide;
1-acetyl-5-(4-{2-[(5-cyclopropyl-1H-pyrazol-3-yl)amino]-2-oxoethyl}phenyl)-1H-indol-3-yl acetate;
2-[4-(2-amino-4-hydroxy-6-methyl-5-pyrimidinyl)phenyl]-N-(5-cyclopropyl-1H-pyrazol-3-yl)acetamide;
N-(5-cyclopropyl-1H-pyrazol-3-yl)-2-[4-(5-pyrimidinyl)phenyl]acetamide;
N-(5-cyclopropyl-1H-pyrazol-3-yl)-2-[4-(2-pyridinyl)phenyl]acetamide;
N-(5-cyclopropyl-1H-pyrazol-3-yl)-2-[4-(5-nitro-2-pyridinyl)phenyl]acetamide;
N-(5-cyclopropyl-1H-pyrazol-3-yl)-2-[4-(6-amino-3-pyridinyl)phenyl]acetamide;
N-(5-cyclopropyl-1H-pyrazol-3-yl)-2-[4-(3-pyridinyl)phenyl]acetamide;
N-(5-cyclopropyl-1H-pyrazol-3-yl)-2-[4-(3-quinolinyl)phenyl]acetamide;
N-(5-cyclopropyl-1H-pyrazol-3-yl)-2-[4-(4-isoquinolinyl)phenyl]acetamide;
5-(4-{2-[(5-cyclopropyl-1H-pyrazol-3-yl)amino]-2-oxoethyl}phenyl)nicotinic acid;
N-(5-cyclopropyl-1H-pyrazol-3-yl)-2-[4-(2-amino-5-pyrimidinyl)phenyl]acetamide;
N-(5-cyclopropyl-1H-pyrazol-3-yl)-2-[4-(4-pyridinyl)phenyl]acetamide;
N-(5-cyclopropyl-1H-pyrazol-3-yl)-2-[4-(5-acetyl-2-thienyl)phenyl]acetamide;
N-(5-cyclopropyl-1H-pyrazol-3-yl)-2-[4-(9H-purin-6-yl)phenyl]acetamide;
2-[4-(1-benzothien-3-yl)phenyl]-N-(5-cyclopropyl-1H-pyrazol-3-yl)acetamide;
5-(4-{2-[(5-cyclopropyl-1H-pyrazol-3-yl)amino]-2-oxoethyl}phenyl)-1H-indol-3-yl acetate;
N-(5-cyclopropyl-1H-pyrazol-3-yl)-2-[4-(2,4-dimethoxy-5-pyrimidinyl)phenyl]acetamide;

N-(5-cyclopropyl-1H-pyrazol-3-yl)-2-[4-(2-chloro-3-thienyl)phenyl]acetamide;
N-(5-cyclopropyl-1H-pyrazol-3-yl)-2-[4-(6-methyl-2-pyridinyl)phenyl]acetamide;
N-(5-cyclopropyl-1H-pyrazol-3-yl)-2-[4-(1H-imidazol-5-yl)phenyl]acetamide;
2-[4-(6-amino-5-nitro-3-pyridinyl)phenyl]-N-(5-cyclopropyl-1H-pyrazol-3-yl)acetamide;
N-(5-cyclopropyl-1H-pyrazol-3-yl)-2-[4-(2,3,5,6-tetrafluoro-4-pyridinyl)phenyl]acetamide;
N-(5-cyclopropyl-1H-pyrazol-3-yl)-2-[4-(4-methyl-2-pyridinyl)phenyl]acetamide;
N-(5-cyclopropyl-1H-pyrazol-3-yl)-2-[4-(1H-pyrazol-4-yl)phenyl]acetamide;
5-(4-{2-[(5-cyclopropyl-1H-pyrazol-3-yl)amino]-2-oxoethyl}phenyl)-2-thiophene acid;
N-(5-cyclopropyl-1H-pyrazol-3-yl)-2-[4-(6-methoxy-2-pyridinyl)phenyl]acetamide;
6-(4-{2-[(5-cyclopropyl-1H-pyrazol-3-yl)amino]-2-oxoethyl}phenyl)-2-pyridinecarboxylic acid;
N-(5-cyclopropyl-1H-pyrazol-3-yl)-2-[4-(2,4-dichloro-5-pyrimidinyl)phenyl]acetamide;
N-(5-cyclopropyl-1H-pyrazol-3-yl)-2-[4-(4-methyl-3-thienyl)phenyl]acetamide;
N-(5-cyclopropyl-1H-pyrazol-3-yl)-2-[4-(5-formyl-2-furyl)phenyl]acetamide;
N-(5-cyclopropyl-1H-pyrazol-3-yl)-2-[4-(6-nitro-3-pyridinyl)phenyl]acetamide;
N-(5-cyclopropyl-1H-pyrazol-3-yl)-2-[4-(8-quinolinyl)phenyl]acetamide;
N-(5-cyclopropyl-1H-pyrazol-3-yl)-2-[4-(5-methyl-2-pyridinyl)phenyl]acetamide;
N-(5-cyclopropyl-1H-pyrazol-3-yl)-2-[4-(3-methyl-2-pyridinyl)phenyl]acetamide;
N-(5-cyclopropyl-1H-pyrazol-3-yl)-2-[4-(1H-indol-7-yl)phenyl]acetamide;
N-(5-cyclopropyl-1H-pyrazol-3-yl)-2-[4-(6-methoxy-3-pyridinyl)phenyl]acetamide;
N-(5-cyclopropyl-1H-pyrazol-3-yl)-2-[4-(2-amino-9H-purin-6-yl)phenyl]acetamide;
N-(5-cyclopropyl-1H-pyrazol-3-yl)-2-[4-(2-methyl-1H-indol-5-yl)phenyl]acetamide;
N-(5-cyclopropyl-1H-pyrazol-3-yl)-2-[4-(6-fluoro-3-pyridinyl)phenyl]acetamide;
N-(5-cyclopropyl-1H-pyrazol-3-yl)-2-[4'-(ethylsulfanyl)[1,1'-biphenyl]-4-yl]acetamide;
N-(5-cyclopropyl-1H-pyrazol-3-yl)-2-(3',4'-dimethyl[1,1'-biphenyl]-4-yl)acetamide;
N-(5-cyclopropyl-1H-pyrazol-3-yl)-2-(4'-hydroxy[1,1'-biphenyl]-4-yl)acetamide;
(2E)-3-(4'-{2-[(5-cyclopropyl-1H-pyrazol-3-yl)amino]-2-oxoethyl}[1,1'-biphenyl]-3-yl)-2-propenoic acid;
N-(5-cyclopropyl-1H-pyrazol-3-yl)-2-[3'-(trifluoromethyl)[1,1'-biphenyl]-4-yl]acetamide;
N-(5-cyclopropyl-1H-pyrazol-3-yl)-2-(4'-methyl[1,1'-biphenyl]-4-yl)acetamide;
N-(5-cyclopropyl-1H-pyrazol-3-yl)-2-[2'-(methylsulfanyl)[1,1'-biphenyl]-4-yl]acetamide;
4'-{2-[(5-cyclopropyl-1H-pyrazol-3-yl)amino]-2-oxoethyl}[1,1'-biphenyl]-2-carboxylic acid;
3-(4'-{2-[(5-cyclopropyl-1H-pyrazol-3-yl)amino]-2-oxoethyl}[1,1'-biphenyl]-4-yl)propanoic acid;
2-[4'-(benzyloxy)[1,1'-biphenyl]-4-yl]-N-(5-cyclopropyl-1H-pyrazol-3-yl)acetamide;
N-(5-cyclopropyl-1H-pyrazol-3-yl)-2-(2',3'-dichloro[1,1'-biphenyl]-4-yl)acetamide;
N-(5-cyclopropyl-1H-pyrazol-3-yl)-2-(3'-isopropyl[1,1'-biphenyl]-4-yl)acetamide;
N-(5-cyclopropyl-1H-pyrazol-3-yl)-2-[4-(3-formyl-2-furyl)phenyl]acetamide;
(2E)-3-(4'-{2-[(5-cyclopropyl-1H-pyrazol-3-yl)amino]-2-oxoethyl}[1,1'-biphenyl]-4-yl)-2-propenoic acid;
N-(5-cyclopropyl-1H-pyrazol-3-yl)-2-{4'-[(E)-2-nitroethenyl][1,1'-biphenyl]-4-yl}acetamide;
2-(4'-chloro[1,1'-biphenyl]-4-yl)-N-(5-cyclopropyl-1H-pyrazol-3-yl)acetamide;
N-(5-cyclopropyl-1H-pyrazol-3-yl)-2-(3'-methyl[1,1'-biphenyl]-4-yl)acetamide;
2-(4'-phenyl[1,1'-biphenyl]-4-yl)-N-(5-cyclopropyl-1H-pyrazol-3-yl)acetamide;
N-(5-cyclopropyl-1H-pyrazol-3-yl)-2-(4'-phenoxy[1,1'-biphenyl]-4-yl)acetamide;
N-(5-cyclopropyl-1H-pyrazol-3-yl)-2-(2'-formyl[1,1'-biphenyl]-4-yl)acetamide;
2-(3'-chloro-[1,1'-biphenyl]-4-yl)-N-(5-cyclopropyl-1H-pyrazol-3-yl)acetamide;
N-(5-cyclopropyl-1H-pyrazol-3-yl)-2-(3'-formyl[1,1'-biphenyl]-4-yl)acetamide;
tert-butyl 2-(4-{2-[(5-cyclopropyl-1H-pyrazol-3-yl)amino]-2-oxoethyl}phenyl)-1H-pyrrole-1-carboxylate;
2-(3'-cyano[1,1'-biphenyl]-4-yl)-N-(5-cyclopropyl-1H-pyrazol-3-yl)acetamide;
N-(5-cyclopropyl-1H-pyrazol-3-yl)-2-(4-dibenzo[b,d]furan-4-ylphenyl)acetamide;
or a pharmaceutically acceptable salt thereof.

8. A pharmaceutical composition, comprising the 3-amino-pyrazole derivative of claim 1 and at least one pharmaceutically acceptable carrier and/or diluent.

9. A pharmaceutical composition according to claim 8 further comprising one or more chemotherapeutic agents.

10. A pharmaceutical composition comprising a compound of claim 1; one or more chemotherapeutic agents; and at least one pharmaceutically acceptable carrier and/or diluent.

11. A compound as defined in claim 1 for use as a medicament.

* * * * *